United States Patent
Wilson et al.

(10) Patent No.: US 6,326,165 B1
(45) Date of Patent: Dec. 4, 2001

(54) RECOMBINANT BHLH-PAS/JHR POLYPEPTIDE AND ITS USE TO SCREEN POTENTIAL INSECTICIDES

(75) Inventors: Thomas G. Wilson, Fort Collins, CO (US); Julia N. Heinrich, Princeton, NJ (US)

(73) Assignees: Colorado State University Research Foundation, Fort Collins, CO (US); American Cyanamid Company, Princeton, NJ (US)

(*) Notice: Subject to any disclaimer, the term of this patent is extended or adjusted under 35 U.S.C. 154(b) by 0 days.

(21) Appl. No.: 08/971,188

(22) Filed: Nov. 17, 1997

Related U.S. Application Data

(63) Continuation-in-part of application No. 08/843,205, filed on Apr. 14, 1997, now abandoned.

(51) Int. Cl.$^7$ ............ C12P 21/00; C12P 21/02; C12N 15/63; C12N 5/10
(52) U.S. Cl. ............ 435/69.1; 435/320.1; 435/455; 435/325; 435/348; 435/254.11; 435/254.2; 435/252.3; 536/23.1; 536/23.5
(58) Field of Search .................... 435/320.1, 69.1, 435/455, 325, 348, 366, 254.11, 254.2, 282.3; 536/23.1, 23.5

(56) References Cited

PUBLICATIONS

Harvey et al., "HL01770, 5 prime HL *Drosophila melanogaster* head BlueScript EST clone." Database EST; Genbank Accession AA 567788. dbEST entry: Aug. 21, 1997, updated Dec. 18, 1997.

Mak et al., "Expression of functional chicken oviduct progesterone receptors in yeast (saccharomyces cerevisiae," J.Biol.Chem. 264(36):21613–21618 (1989).

Mak et al., "Retinoid X receptor homodimers function as transcriptional activators in yeast," Gene 145:129–133 (1994).

McDonnell et al., "Reconstitution of the Vitamin D–Responsive osteocalcin transcription unit in saccharomyces cerevisiae," Molecular and Cellular Biology 9(8): 3517–3523 (1989).

Rowlands et al., "Aryl hydrocarbon receptor–mediated signal transduction," Critical Reviews in Toxicology 27(2): 109–134 (1997).

Rowlands et al., "Human Dioxin Receptor Chimera Transactivation in a yeast model system and studies on receptor agonists and antagonists," Pharmacology & Toxicology 76:328–333 (1995).

Shemshedini et al., "Evidence for a Juvenile Hormone Receptor Involved in Protein Synthesis in Drosophila Melanogaster," J.Biol.Chem. 265(4): 1913–1918 (1990).

Turner et al., "Molecular analysis of the methoprene–tolerant gene region of drosophila melanogaster," Archives of Insect Biochemistry and Physiology 30:133–147 (1995).

Whitelaw et al., "Identification of transactivation and repression functions of the Dioxin receptor and its basic helix–loop–helix/PAS partner factor arnt: inducible versus constitutive modes of regulation," Molecular and Cellular Biology 14(12): 8343–8355 1994.

Wilson et al., "A drosophila melanogaster mutant resistant to a chemical analog of juvenile hormone," Developmental Biology 118:190–201 (1986).

Yamaguchi et al., "Functional analysis of aryl hydrocarbon receptor nuclear translocator interactions with aryl hydrocarbon receptor in the yeast two–hybrid system," Biochemical 50 Pharmacology, 50(8): 1295–1302 (1995).

Zelzer et al., "The PAS domain confers target gene specificity of Drosophila bHLH/PAS proteins," Genes & Development 11:2079–2089 (1997).

Yao et al., "*Drosophila ultraspiracle* Modulates Ecdysone Receptor Function via Heterodimer Formation," *Cell*. Oct. 2, 1992, vol. 71, pp. 63–72.

Shemshedini et al., "Resistance to juvenile hormone and an insect growth regulator in Drosophila is associated with an altered cytosolic juvenile hormone–binding protein," Proc. Natl. Acad. Sci. USA, Mar. 1990, vol. 87, pp. 2072–2076.

Kelley et al., "Restriction of P–Element insertions at the Notch Locus of *Drosophila melanogaster*," *Molecular and Cellular Biology*, Apr. 1987, vol. 7, No. 4, pp. 1545–1548.

*Primary Examiner*—David Guzo
(74) *Attorney, Agent, or Firm*—Sutherland Asbill & Brennan LLP

(57) ABSTRACT

Promising groups of environmentally-safe insecticides consist of analogues of insect hormones, such as juvenile hormone, and antagonists of such hormones. The traditional bioassay approach for screening potential juvenile hormone analogs and antagonists is slow, expensive and inefficient. A recombinant bHLH-PAS-juvenile hormone receptor, isolated from methoprene-tolerant locus on Drosophila, provides the basis of in vitro and in vivo binding assays that can be used to discover new juvenile hormone-type targeted insecticides. Moreover, the nucleotide sequence of the Drosophila bHLH-PAS/JHR polypeptide provides tools for isolating juvenile hormone receptor genes from other insect species.

24 Claims, 16 Drawing Sheets

6.234kbGENOMIC

```
   1 AGGCCTTGACATTGTTAATCAGGTGGCTCAATCCATTATAGCCATCCTTATCGAAGTCGATGTTCTCGCCGCCAAACTCGATGACCTGCAAATGAATAGT
 101 GGGCAAATGGTTTGGGATCATTGAAATAAATGACTCCATGGATTGAGTGCACCCACCTCCTTGGCCCTGAAGGTGTCCGCACCATGGGGCACTCCAATGA
 201 ACTCGAACCAGGCCCCTTCGGGGGGGCCCAGCTCACCGGCAGATTGATCTTTAGCTTGTGGTTGTCTGTGGAACTGGCCAGCAAAGTGGATCCCGCGACG
 301 CTCTCCACGCGAACCATTATGCTCACGGTTTGGCCGGAAAACTGCTTCAGCATGCCGCCGTTGATAATCGAGCGTGGATCAAAGGCATCCATAATAACTC
 401 CTCAGTTAATAACGTTCAAAAAACAGCCAATTTCAGCAGAAAATGAAATGCCGTAAACAAGAAAGAGCGCCAATAGTTATCGAGCGTGCTAATCGATAAT
 501 AAAAATTGCATGACGTCTGCTATCGAAATTATTCGAATTTTGTAGCAAAAATATTTATGGGATTTATTGTAACATCAAAAGTTATTACATTATTACTGTGG
 601 ACTTATGTATTATAATAAGAATTAATAAAAATAATTTATAATAGAATTATAAAAAGACCTGATAGATTACATGTATTACAACAATGTTATCGACAGCGAA
 701 CAAGATGTTCGAATCTTTCTGATATTTTGTCCGGTGTGAACGTGCGAATTTTAGTACGACAACCAGTTACATCGATGTATCGATAGTTTTTAGACTGGCC
 801 AATGTTTATTGTTATAAAATAAATGTTAAAAATAAACAATTAATCACTTAGTATAAACAAAAATAAGTGCAAGCAGCAAGTGCGTTGTTAAAACGACCGC
 901 CGCCCTCCGAATTTCCTTATTGCGGGCATTAAATCGCAACAACAACAACGCCACCAGCAACAGCAACAACAATAAGCAGGAGATTCAGATTCGAACGCA
1001 ATCAAAACGTAAAAAAAAACGAAAAATAAAAAACTACAAGGCGAAACGCATAAATAAATAGGGAAGCAAATAATAGTAATAATAAGACTAAAAGCAAGT
1101 GGAAAAGTACGAAAGCGAAAAGAGAAAACATATGTACGTTGCGTGAGAGTGACGTGTGTGTGTGTGTGTCAGTGAGCGAAGGAGAGTGAGCGAGAGAGGG
1201 GAGGCGAGCAAAAACAAAAACAACAGCACAGCACACAGCATAAGCGAGACCTTGAAAACTTTAAAAGCAGCAAAAAAAAACAAGACAACAGCCAAAAATAA
1301 GAAACTAAAAGCTGCAAAAGTAATAAAAAATATATTTTAGCCGAAAAATTTCCATAATAACAATTCTAGAAGTGCGGAGCGTACACCCTGTTATGGAGAG
1401 TGACGATTTTCATTTACCGCAAGGCGCCAATTAAAGGGGAAAATCCATAAATCGAGGATTACAAGTGGAAAACAAGGAGGCAGTAACTCCAGAAAACGCC
1501 CAAAAAGTCCAAAATGGCAGCACCAGAGACGGGCAACACGGGCTCCACAGGATCCGCTGGCTCGACAGGATCGGGATCGGGATCGGGAAGTGGG
1601 AGCTCCTCAGATCCAGCGAATGGACGGGAGGCCCGTAACCTTGCCGAAAAACAGCGACGGGATAAGCTTAATGCCAGCATCCAGGAGCTGGCCACCATGG
1701 TACCACATGCAGCCGAATCCTCCCGTCGCCTGGACAAAACCGCCGTCCTTAGATTCGCCACCCATGGCCTGAGACTTCAGTATGTCTTTGGCAAGTCCGC
1801 TTCCAGACGTCGCAAGAAAACCGGCCTCAAGGGAACGGGTATGTCTGCCTCACCTGTCGGAGATCTACCCAATCCCAGTCTGCATCTAACGGACACTCTA
1901 ATGCAACTGCTGGACTGCTGCTTCCTCACCCTAACCTGCAGTGGCCAAATCGTTTTGGTATCCACCAGCGTGGAGCAGCTATTGGGTCACTGTCAGTCCG
2001 ATTTGTATGGCCAGAATCTACTGCAGATCACGCATCCCGATGATCAGGATCTGTTAAGACAGCAGCTAATACCCAGGGATATAGAGACCCTGTTCTATCA
2101 GCATCAGCACCACCAGCAGCAGGGGCACAATCCCCAGCAGCACCTTCCACGTCGGCCTCAGCTTCGGGACAGTGATCTGGAGGAGGAGGAAATGGAG
2201 ACGGAGGAACACCGTCTGGGTCGGCAGCAGGGAGAGGCGGACGATGACGAGGATCACCCGTACAACGGACGAACACCCAGCCGCGGAGAATGGCCCATT
2301 TGGCGACCATTGATGACCGACTACGCATGCATGGATCGGCGCTGCTTTACCGTCCGCTTGGCTAGGGCTTCCACGCGAGCGGAGGCCACGCGTCATTACGAGCG
2401 GGTTAAGATCGATGGCTGCTTTCGTCGCAGTGACTCTCCTTAACCGGAGGTGCCGCTGCCAACTATCCGATTGTCTCCCAGCTGATACGACGCTCGAGA
2501 AACAACAATATGCTGGCTGCCGCTGCAGCAGTGGCAGCAGAAGCGGCGACGGTGCCACCCCAGCACGATGCCATTGCCCAGGCGGCGCTGCACGGGATTA
2601 GCGGCAATGATATTGTCCTGGTGGCCATGGCCAGGGTGCTGCGAGAGGAACGGCCGCCTGAGGAGACGGAGGGTACAGTGGGCTTGACCATTTACAGACA
2701 GCCAGAACCCTATCAGCTGGAGTACCATCACGAGGCATCTAATCGACGGCACGCATCATCGACTGTGATCAAAGGATTGGTCTGGTGGCGGGATATATGAAG
2801 GATGAGGTgggtatattaacatcatctctctgaactgcttacgacaactaatcgtgtactctccactcgaaacaggtgCGCAACCTTAGTCCCTTCTGTT
2901 TCATGCACCTGGACGACGTTCGCTGGGTGATTGTGGCCCTTCGACAAATGTACGATTGCAACAGTGACTATGGCGAGAGCTGCTACCGTCTGCTGTCCCG
3001 CAACGGGCGCTTCATTTACCTGCACACCAAGGGATTTCTGGAGGTCGACCGTGGCAGTAATAAGGTGCATTCCTTTCTGTGCGTCAACACGCTGCTCGAT
3101 GAGGAGGCGGGCCGGCAAAAGGTGCAGGAGATGAAGGAGAAATTCTCGACAATCATCAAGGCGGAGATGCCCACGCAGAGCAGCAGTCCCGATTTGCCCG
3201 CCTCGCAGGCACCGCAGCAACTTGAGAGAATTGTCCTCTATCTAATAGAGAACCTACAGAAGAGTGTGGATTCAGCAGAGACGGTTGGCGGCAGGGCAT
3301 GGAAAGCCTAATGACGATGGCTACAGTTCGCCAGCAAATACCTTAACTCTCGAGGAGTTAGCTCCCTCGCCCACGCCCGCCTTGGCCTTGGTGCCGCCG
3401 GCTCCCTCATCGGTCAAGAGCTCCATCTCCAAGTCGGTGAGTCGGTCAATGTGACGGCGGCCAGAAAGTTTCAGCAGGAGCATCAGAAGCAGCGTGAAC
3501 GTGACCGTGAGCAGCTTAAGGAGCGCCACCAACTCCACGCAGGGCGTGATCCGGCAACTGAGCAGCTGCCTAAGCGAGGCGGAAACGGCATCCTGTATCCT
3601 ATCACCAGCCAGTAGTCTGAGTGCCAGCGAAGCACCGGACACGCCCGATCCGCACAGCAACACATCACCGCCACCGTCGCTCCACACACGTCCCAGTGTC
3701 CTGCATCGAACCCTGACCAGCACGCTGCGATGACGGGCTGATGGAACCTGGTTTGCCTTCTAATTGGGTGTGTGGAAATGGACGTAATTGGTAGCTCACG
3801 TGCCCACAAACGAATTAGTATCGGTAATATAATCCTGGCCAATCGCAATGTGAAAAACCCAAAATGTATCAGAAAAAAAAACGAGCATTATTCAAATAGTTT
3901 AAAAAATTCAGCCAAAAAACTTAAATACGAAAAAAAAGAGCGTGGGTTGAAGAACCTTTTGTTTTCATATTCACATTTCCAAGCTTTGAGCAATCAAACAA
4001 TTTTAATTTTCAGTATACACATATGTATAATGAGTTGGCTTTACAAAAACGTATTAACAAATCAAGCAATTGTGTAATTTAATATGAGACTTTCCGTGATT
4101 TTTGCTTTCTACGTACTTTTCGACTTCAATTGATCTATAGGGTTTCCGTATTAAAAACGAAATTAACGTGGTTTCATTTGATGAAAATGCAATATGAGCT
4201 CGCATTTATTTTGATATTTATGACAGTAATAATGATCTGATCACGATAATCGTTTTCTCAAAACATAAGCGATACATTTTGGGTACATTTGGCCATTACTG
4301 TTTCTGTGTGTGATTTCGGTATAAAATAGTAGTTTGATTACATGTTATATTGATGAATGGCGATCGGTGGGTGCTGCTAAATGCGTTCCATTATCAATAA
4401 TTTTCGTTATGTAATTACGTTTAATTTGTAAATATGATGCGAGCGTGAGTGAGTTGTGATCGTGTCAGCATGGGTGTGAATGAACATTAGATCA
4501 GTGCTCGGATTTGGTTTTAGTTGAAATTTAAACCCCATTTCCCGATTTCCCAGTTATCACCTTCCGCCCCAAAACACCATTGTAAAAAGAGTACAAAAA
4601 AAAAAARAAAAGAAAATAGAAAAACAAACAAACAATTATATATTTATTTTCGCCCTAAGTCTAGAACGTGCTAAACACAACTCATTAATAGTTAAACAAAC
4701 GGATGTTGCAATCGATGGAAATTAAACGCTCGCTTTTAGTTTTGCCGTCTCGCTCGAAGAAAGAAAGAGGACTACTACATATGTACAGTCAAACTAATCC
4801 AAGTCAAACTCTTCAGTCTCAGAATTGGAGACTTTATTAAAGGTTTTTTATTTTATGAAGAATAGCATATTATTTTTTATATATATATATTTATGTATATA
4901 TATTTATATCACAAATCTCCTTCGATATCCCTTTGTAATCTATAAAAACACTTCCAGGCGCAGCTTTATTTTTCAACAGTTTTAATTTTGGGAACTTTAC
5001 AAAGCATATAAGCATACCCCAAATCCATATCCTTATAAACTTTGTAGTTATTACAAAATGTGTTCAAAATTAAAAAAAAAAAAGTTTGTCATCCAAAATCC
5101 AATCCGCTAAATCAATATAATCATTTTAATTGATCTATGTTACACTTCTATAATGTCTACTGGACAAAATATGATTAAGTTGAAATTTCAAAGTGTTTT
5201 TGAAGTTTGTACTAACGAAGTTTGGCTGTAGTTCAATACTCACAGAAAGGGAGCGAGACATATTCCCATCTCGCTCCGACCTGTTATCAAAGCCTTTGCC
5301 ATTGTCCTTGGCGTTGCGTTCTTATCACCGGCGTATCGGAGGGAATATATGATTTTTTTTTCGGCCAAGTGGTTCTAGTGGTAAATATGAAGCGGTGGGT
5401 GGTTTCCGGGGGTTTGGGGGAACCGCGGTTGGTGATGGGCGCAGAGAAGGCGGGAAGCGGGGGGGAACACGTTTCGTTATTTTTTGTTTATAGCGAAAT
5501 TCCTCTAGCTATAAATGTATGCATACATATATGCTATTAACTTTTCGTTTAGCTCAATTTTTTGTTTGTATTTTAATTATAACTCGGTTTGTCTAGTGT
5601 GTAATTAAATTAAAAGTCCAATGCTAATTCCCCAGCGAATCGTTCAGTGTTTGTTCAAACGAGTTGTGCTCTTTAAACACTTTTGGCTTATCCTTTCATT
5701 TAATTTTTGTTTGTTTTCCTTGCGTTGATTAAAAATAGTCCAAATAAAAATGAAAGTTTGAATTGTTTTTTTTAGTAATTTAGTTTTAACTGTAATGTCAAAT
5801 GTCGAGAGGTATACTCTGTATAAGAATAATAATGTGTAATGTAATTTTTAGAACTTGCTAATCTCTAGCAATTAAAACATAGCCTGTAATTAACAATAAT
5901 TAATTATAATAACCAGTAACAGTTCATGCAAATGAAACCTTAATAAATAATAAATTATATAAAAGAAGATGAAGTGTTTTCAATCAATGAAGTTACTTC
6001 CTATTTTCAGGAGTTGGAATGTTACACTTTTTTATAAGCTGATTTGAAATGCGCGCCACATTATATCTGCCTTGCGCGCACGCATTGCAGCCGAATAACG
6101 GCGAATTAACTCCCCTCAGAGGTGAGTTTGAACTATCGATTATAATCGATTGCATTCGGAAACAAAAAACACCTTGAGTTTGGTCAGATCGGTTTTGCGC
6201 GGGATAAATAATAAAATATTTAAATGTTTTCTTTG
```

```
1   M A A P E T G N T G S T G S A G S T G S G S G S G S G S G S S S D P A N G R E A     AA Genomic
1   M A A P E T G N T G S T G S A G S T G S G S G S G S G S G S S S D P A N G R E A        cDNA 41  R N L A E K Q R R D K L N A S I Q E L A T M V P H A A E S S R R L D K T A V L R     AA Genomic
41  R N L A E K Q R R D K L N A S I Q E L A T M V P H A A E S S R R L D K T A V L R        cDNA 81  F A T H G L R L Q Y V F G K S A S R R R K K T G L K G T G M S A S P V G D L P N     AA Genomic
81  F A T H G L R L Q Y V F G K S A S R R R K K [X] G L K G T G M S A S P V G D L P N      cDNA 121 P S L H L T D T L M Q L L D C C F L T L T C S G Q I V L V S T S V E Q L L G H C     AA Genomic
121 P S L H L T D T L M Q L L D C C F L T L T C S G Q I V L V S T S V E Q L L G H C        cDNA 161 Q S D L Y G Q N L L Q I T H P D D Q D L L R Q Q L I P R D I E T L F Y Q H Q H H     AA Genomic
161 Q S D L Y G Q N L L Q I T H P D D Q D L L R Q Q L I P R D I E T L F Y Q H Q H H        cDNA 201 Q Q Q G H N P Q Q H S T S T S A S [X] S G S D L E E E E M E T E E H R L G R Q Q G   AA Genomic
201 Q Q Q G H N P Q Q H S T S T S A S [A] S G S D L E E E E M E T E E H R L G R Q Q G      cDNA 241 E A D D D E D H P Y N R R T P S P R R M A H L A T I D D R L R M D R R C F T V R     AA Genomic
241 E A D D D E D H P Y N R R T P S P R R M A H L A T I D D R L R M D [W] R C F T V R      cDNA 281 L A R A S T R A E A T R H Y E R V K I D G C F R R S D S S L T G G A A A N Y P I     AA Genomic
281 L A R A S T R A E A T R H Y E R V K I D G C F R R S D S S L T G G A A A N Y P I        cDNA 321 V S Q L I R R S R N N N M L A A A A A V A A E A A T V P P Q H D A I A Q A A L H     AA Genomic
321 V S Q L I R R S R N N N M L A A A A A V A A E A A T V P P Q H D A I A Q A A L H        cDNA 361 G I S G N D I V L V A M A R V L R E E R P P E E T E G T V G L T I Y R Q P E P Y     AA Genomic
361 G I S G N D I V L V A M A R V L R E E R P P E E T E G T V G L T I Y R Q P E P Y        cDNA 401 Q L E Y H T R H L I D G S I I D C D Q R I G L V A G Y M K D E V G I L T S S L .     AA Genomic
401 Q L E Y H T R H L I D G S I I D C D Q R I G L V A G Y M K D E V - - - - - - - -        cDNA 441 T A Y D N . S C T L H S K Q V R N L S P F C F M H L D D V R W V I V A L R Q M Y     AA Genomic
433 - - - - - - - - - - - - - - - R N L S P F C F M H L D D V R W V I V A L R Q M Y        cDNA 481 D C N S D Y G E S C Y R L L S R N G R F I Y L H T K G F L E V D R G S N K V H S     AA Genomic
458 D C N S D Y G E S C Y R L L S R N G R F I Y L H T K G F L E V D R G S N K V H S        cDNA 521 F L C V N T L L D E E A G R Q K V Q E M K E K F S T I I K A E M P T Q S S S P D     AA Genomic
498 F L C V N T L L D E E A G R Q K V Q E M K E K F S T I I K A E M P T Q S S S P D        cDNA 561 L P A S Q A P Q Q L E R I V L Y L I E N L Q K S V D S A E T V G G Q G M E S L M     AA Genomic
538 L P A S Q A P Q Q L E R I V L Y L I E N L Q K S V D S A E T V G G Q G M E S L M        cDNA 601 D D G Y S S P A N T L T L E E L A P S P T P A L A L V P P A P S S V K S S I S K     AA Genomic
578 D D G Y S S P A N T L T L E E L A P S P T P A L A L V P P A P S S V K S S I S K        cDNA 641 S V S V V N V T A A R K F Q Q E H Q K Q R E R D R E Q L K E R T N S T Q G V I R     AA Genomic
618 S V S V V N V T A A R K F Q Q E H Q K Q R E R D R E Q L K E R T N S T Q G V I R        cDNA 681 Q L S S C L S E A E T A S C I L S P A S S L S A S E A P D T P D P H S N T S P P     AA Genomic
658 Q L S S C L S E A E T A S C I L S P A S S L S A S E A P D T P D P H S N T S P P        cDNA 721 P S L H T R P S V L H R T L T S T L R .                                             AA Genomic
698 P S L H T R P S V L H R T L T S T L R .                                                cDNA
```

FIGURE 4

```
  1  ATGGCAGCACCAGAGACGGGCAACACGGGCTCCACAGGATCCGCTGGCTCGACAGGATCGGGATCGGGAAGTGGGAGC  A
  1     CAGCAGACGCGGCAACACGGGCACCACAGGATCAGCTGGGTCCACA------GGATCGGGATCGGGAACTGGGACG  B
 91  TCCTCAGATCCAGCGAATGGACGGGAGGCCCGTAACCTTGCCGAAAAACAGCGACGGGATAAGCTTAATGCCAGCATCCAGGAGCT  A
 72  TCCGCAGATCCAGCGAATGGACGGGAGGCCCGCAATCTTGCCGAGAAACAGCGACGGGATAAGCTTAATGCCAGCATCCAGGAGCT  B
181  GGCTACCATGGTACCACATG-CAGCCGAATCCTCCCGTGCCTGGACAAAACCGCCGTCCTTAGATTCGCCACCC  A
158  GGCTACCATGGTACCACATGTCAGCCGAATCCTCCCGACGCCTGGACAAAACCGCCGTCCTCAGATTCGCCACCC  B
```

Match Line to Fig. 6B

Match Line to Fig. 6E

Match Line to Fig. 6A     Match Line to Fig. 6C

```
R L K Q R N S L G P S R D G - T N Y A V V H C T G Y I K N
R N R C R N G L G S V K D G E P H F V V V H C T G Y I K A
S K K - - - - - - - K A D R K S F C T I H S T G Y L K S
D G C F R R S D S S L T G G A A A N Y P I V S Q C I R R S
. . . . . . . . . . . L L D N S S G F L A M N F Q G K L K Y
```

――――――― PAS B ―――――――

```
. . . . . . . D . . . . . . . . . T . . . E . . . . . . .
A M D G K F T F V D Q R V L N I L G Y T P T E L L G K - I
N I E G I F T F V D H R C V A T V G Y Q P Q E L L G K - N
A I D G K F V F V D Q R A T A I L A Y L P Q E L L G T - S
L I D G S I I D C D Q R I G L V A G Y N K O E V R N L - S
K L D F T P I G C D A K G R I V L G Y T E A E L C T R G S
```

Match Line to Fig. 6F

Match Line to Fig. 6B

Match Line to Fig. 6D

Match Line to Fig. 6G

Fig. 6D

```
                                                            Consensus
. . . . . . . . . . . . . . . . . . . . . . .

E R F A S R E N H C E I E R R R N K M T A Y I               Darnt
E R L A - R E N H S E I E R R R N K M T A Y I               Harnt
- - - - A R E A H S Q I E K R R R D K M N S F I             Bmal1
- - - - - R E A R N L A E K Q R R D K L N A S I             Met_Orf
K P I P A - E G I K S N P S K R H R D R L N T E             Ahr_Human
─────────── PAS A ───────────

. . . . . . . . . . S . S . . . . . L . . . Q              Consensus #1

V S C D S G R V I Y V S D S V T P V - L N Y T Q             Darnt
V S C E T G R V V Y V S D S V T P V - L N Q P Q             Harnt
V G C D R G K I L F V S E S V F K I - L N Y S Q             Bmal1
L T C - S G Q I V L V S T S V E Q L - L G H C Q             Met_Orf
V T T D - A L V F Y A S - S T I Q D Y L G F Q Q             Ahr_Human . . . . . . . . . . . . . . . . . . . . . . .              Consensus #1

H - - - - - - Q S S M R L S M G A - - - - - - -             Darnt
Q - - - - - - Q S S M R M C M G S - - - - - - -             Harnt
T - - - - - - P G P S R L C S G A - - - - - - -             Bmal1
H P Y N R R T P S P R R M A H L A T I D D R L R             Met_Orf
- - - - - - - - - - - - - - - - - - - - - - -              Ahr_Human . . . . . . . . . . L . A . . . . . L . . . . .            Consensus #1

- - - D M S S H - C C L V A I G - R - L Q V T S             Darnt
- - - G Q G S K - F C L V A I G - R - L Q V T S             Harnt
- - - N E G C N L S C L V A I G - R - L H S H V             Bmal1
A L H G I S G N D I V L V A M A - R V L R E E R             Met_Orf
- - - - - - - - L A L F M I A T P - L Q P P S               Ahr_Human . . . . . . . . . . . . . . . . . . . . . . .              Consensus L L Y R A R A K N S E Y Y V W L R T Q A Y A F L             Darnt
V M F R F R S K N Q E - W L W M R T S S F T F Q             Harnt
N C Y K F K I K D G S - F I T L R S R W F S F M             Bmal1
S C Y R L L S R N G R - F I Y L N T K O F L E V             Met_Orf
I V F R L L T K N N R W T W V Q S N A R L L Y K             Ahr_Human
─────────── Match Line to Fig. 6H ───────────
```

Match Line to Fig. 6C

Match Line to Fig. 6A

```
370  N P Y T D E V E Y I V C T N S S G K - - - - - - - - -
448  N P Y S D E I E Y I I C T N T N V K N S S Q E P R P T L
425  N P W T K E V E Y I V S T N T V V - - - - - - - - - - -
489  D R G S N K V H S F L C V N T L L - D E E A G R Q - - K
477  N - - - G R P D Y I I V T Q R P L T D E E G T E H L R K

463  A P T P Q Q Q Q Q Q Q R P G S A Q T T P V - - - - - -
558  R F S E I Y H N I N A D Q S K G I S S S T V P A T Q Q L
500  A E E I M E I H R I G S S P S S - - - - - - - - - - C
673  - - - - - M E S L M D D G Y S S P A N T L T L E E - - -
477  S T A P F E N N F F N E S M N E C R N W Q D N T A P M G

636  T S - - - - - - - - - - - - - P A R S P S G P T Y T Q
668  G V G S F Q T P S S F S S M S L P G A P T A S P G A A A
593  P S N D E A A M A V I M S L L E A D A G L G G P V D F S
870  S C I L S P A S S L S A S E A P D T P D P H S N T S P P
587  D S L S K S P F I P S D Y Q Q Q Q S L A L N S S C M V Q

621  A A D V G S H A D H V
700  L G D Q S N S Y N N E E F P D L T M F P P F S E
620
716
696  Y T Q N F I S C N Q P V L P Q H S K C T E L D Y P M G S 631
789
626
718
906  V K F
```

Consensus *Consensus #1*: When all match the residue of Met_Orf show the residue of Met_Orf. otherwise show * *

Fig. 6E

Match Line to Fig. 6F

Match Line to Fig. 6B

```
- - T M H G A P L D A A A A H T P E - - - - Q V Q Q Q Q Q
S N T I Q R P Q L G P T - - A N L P L E M G S G Q L A P R
- - - - - - - - - - L A N V L E G G D P T F P Q L T A
V Q E M K E K F S T I I K A E M P T Q S S S P D L P A S Q
R N T K L P F M F T T G E A V L Y E A T N P F P A I M D P

- G Y T Y D T T H S P - - - Y S A G G T S P L A K I P K S
F S Q G N T F P P T P R P A E N F R N S G L A P P V T I V
G S S P L N I T S T P P P D A S S P G G K K I L N G G T P
- - - - - L A P S P T P A L A L V P P A P S S V K S S I S
N D T I L K H E Q I D Q P Q D V N S F A G G H P G L F Q D

- - - - - - - - - L S A G N G N R Q Q A Q P G A Y Q A G
Y P S - - - - - - - - L T N R G S N F - - A P E T G Q T A
D - - - - - - - - - L P W P L
- P S - - - - - - - - L H T R P S V L H R T L T S T L R
E H L H L E Q Q Q Q H - H Q K Q V V V E P Q Q Q L C Q K M

F E P S P Y P T T S S L E D F V T C L Q L P E N Q K H G L
```

Decoration *Decoration #1*: box residues that match Met_Orf exactly

Fig. 6F

Match Line to Fig. 6C

```
Q Q Q E Q H V Y V Q A A P G V D - Y A R R E L T P V G S A
Q Q Q Q Q T E L D M V P G R D G L A S Y N H S Q V V Q P V
S P H S M D S M L P S G E G G P K R T H P T V P G I P G G
A P Q Q L E R I V L Y L I E N L Q K S V D S A E T V G G Q
L P L R T K N - - - G T S G K D S A T T S T L S K D S L N

G T S P T P V - - - - - - - - - - - - - - - - - A P N S
Q P S A S A G Q M L A Q I S R H S N P T Q G A T P T W T P
D I P S S G L L S G Q A Q E N - - - - - - P G Y P Y S D
K S V S V V N V T A A R K F Q Q E H Q K Q R E R D R E Q L
S K N S D L Y S I M K N L G I D F E D I R H M Q N E K F F

P P P P P N A P G M W D W Q Q A G G H P H P P H P T A H P
G Q F Q T R T A E G V G V W P Q W Q G Q Q P H H R S S S S

K H M Q V N G M F E N W S N Q F V P F N C P Q Q D P Q Q

N P Q S A I I T P Q T C Y A G A V S M Y Q C Q P E P Q H T
```

Match Line to Fig. 6F
Match Line to Fig. 6H

Fig. 6G

Match Line to Fig. 6D

| | | | | | | | | | | | | | | | | | | |
|---|---|---|---|---|---|---|---|---|---|---|---|---|---|---|---|---|---|---|
| . | . | . | . | . | . | . | . | . | . | . | . | . | . | . | . | . | . | Consensus |
| T | N | . | . | . | . | . | . | . | . | . | D | G | M | Y | Q | T | H | M | L | A | M | Q | Darnt |
| T | T | T | G | P | E | H | S | K | P | L | E | K | S | D | G | L | F | A | Q | D | R | D | P | Harnt |
| T | R | A | G | . | . | . | . | . | . | . | . | . | . | . | A | G | K | I | G | R | M | I | Bmal 1 |
| G | . | . | . | . | . | . | . | . | . | . | . | . | . | . | . | . | . | . | . | . | . | . | . | Met_Orf |
| P | S | S | L | L | A | A | M | M | Q | Q | D | E | S | I | Y | L | Y | P | A | S | S | T | S | Ahr_Human |
| . | . | . | . | . | . | . | . | . | . | . | . | . | . | . | . | . | . | . | . | . | . | . | . | Consensus |
| W | A | A | L | R | P | Q | Q | Q | Q | Q | Q | Q | P | V | T | E | G | Y | Q | Y | Q | Q | Darnt |
| T | T | R | S | G | F | S | A | Q | Q | V | A | T | Q | A | T | A | K | T | R | T | S | Q | F | Harnt |
| S | S | S | I | L | G | E | N | P | H | I | G | I | D | M | I | D | N | D | Q | G | S | S | S | Bmal 1 |
| K | E | R | T | N | S | T | Q | G | V | I | R | Q | L | S | S | C | L | S | E | A | E | T | A | Met_Orf |
| R | N | D | F | S | G | E | V | D | F | R | D | I | D | L | T | D | E | I | L | T | Y | V | Q | Ahr_Human |
| . | . | . | . | . | . | . | . | . | . | . | . | . | . | . | . | . | . | . | . | . | . | . | . | Consensus |
| H | H | P | H | A | H | P | G | G | P | A | G | A | G | Q | P | Q | G | Q | G | V | L | R | Y | Darnt |
| E | Q | H | V | Q | Q | P | P | A | Q | Q | P | G | Q | P | E | V | F | Q | E | M | L | S | M | Harnt |
| | | | | | | | | | | | | | | | | | | | | | | | | Bmal 1 |
| | | | | | | | | | | | | | | | | | | | | | | | | Met_Orf |
| Y | N | V | F | T | D | L | H | G | I | S | Q | E | F | P | Y | K | S | E | M | D | S | M | P | Ahr_Human |
| . | . | . | . | . | . | . | . | . | . | . | . | . | . | . | . | . | . | . | . | . | . | . | . | Consensus |
| | | | | | | | | | | | | | | | | | | | | | | | | Darnt |
| | | | | | | | | | | | | | | | | | | | | | | | | Harnt |
| | | | | | | | | | | | | | | | | | | | | | | | | Bmal 1 |
| | | | | | | | | | | | | | | | | | | | | | | | | Met_Orf |
| H | V | G | Q | M | Q | Y | N | P | V | L | P | G | Q | Q | A | F | L | N | K | F | Q | N | G | Ahr_Human |
| . | . | . | . | . | . | . | . | . | . | . | . | . | . | . | . | . | . | . | . | . | . | . | . | Consensus |
| | | | | | | | | | | | | | | | | | | | | | | | | Darnt |
| | | | | | | | | | | | | | | | | | | | | | | | | Harnt |
| | | | | | | | | | | | | | | | | | | | | | | | | Bmal 1 |
| | | | | | | | | | | | | | | | | | | | | | | | | Met_Orf |
| | | | | | | | | | | | | | | | | | | | | | | | | Ahr_Human |

Match Line to Fig. 6G

SEQUENCE LISTING

<160> NUMBER OF SEQ ID NOS: 14

<210> SEQ ID NO 1
<211> LENGTH: 6234
<212> TYPE: DNA
<213> ORGANISM: St-H segment

<400> SEQUENCE: 1

| | | | | | |
|---|---|---|---|---|---|
| aggccttgac | attgttaatc | aggtggctca | atccattata | gccatcctta | tcgaagtcga | 60 |
| tgttctcgcc | gccaaactcg | atgacctgca | aatgaatagt | gggcaaatgg | tttgggatca | 120 |
| ttgaaataaa | tgactccatg | gattgagtgc | acccacctcc | ttggccctga | aggtgtccgc | 180 |
| accatggggc | actccaatga | actcgaacca | ggccccttcg | gggggccca | gctcaccggc | 240 |
| agattgatct | ttagcttgtg | gttgtctgtg | gaactggcca | gcaaagtgga | tcccgcgacg | 300 |
| ctctccacgc | gaaccattat | gctcacggtt | tggccggaaa | actgcttcag | catgccgccg | 360 |
| ttgataatcg | agcgtggatc | aaaggcatcc | ataataactc | ctcagttaat | aacgttcaaa | 420 |
| aaacagccaa | tttcagcaga | aaatgaaatg | ccgtaaacaa | gaaagagcgc | caatagttat | 480 |
| cgagcgtgct | aatcgataat | aaaattgcat | gacgtctgct | atcgaaatta | ttcgaatttt | 540 |
| gtagcaaaaa | tatttatggg | atttattgta | acatcaaaag | ttattacatt | attactgtgg | 600 |
| acttatgtat | tataataaga | attaataaaa | ataatttata | atagaattat | aaaaagacct | 660 |
| gatagattac | atgtattaca | acaatgttat | cgacagcgaa | caagatgttc | gaatctttct | 720 |

-continued

```
gatattttgt ccggtgtgaa cgtgcgaatt ttagtacgac aaccagttac atcgatgtat      780
cgatagtttt tagactggcc aatgtttatt gttataaaat aaatgttaaa aataaacaat      840
taatcactta gtataaacaa aaataagtgc aagcagcaag tgcgttgtta aaacgaccgc      900
cgccctccga atttccttat tgcgggcatt aaatcgcaac aacaacaacg ccaccagcaa      960
cagcaacaac aataagcagg agattcagat tcgcaacgca atcaaaacgt aaaaaaaaaa     1020
cgaaaaataa aaaactacaa ggcgaaacgc ataaataaat agggaagcaa ataatagtaa     1080
taataagact aaaagcaagt ggaaaagtac gaaagcgaaa agagaaaaca tatgtacgtt     1140
gcgtgagagt gacgtgtgtg tgtgtgtgtc agtgagcgaa ggagagtgag cgagagaggg     1200
gaggcgagca aaaacaaaaa caacagcaca gcacacagca taagcgagac cttgaaaact     1260
ttaaaagcag caaaaaaaac aagacaacag ccaaaaataa gaaactaaaa gctgcaaaag     1320
taataaaaaa tatattttag ccgaaaaatt tccataataa caattctaga agtgcggagc     1380
gtacaccctg ttatggagag tgacgatttt catttaccgc aaggcgccaa ttaaagggga     1440
aaatccataa atcgaggatt acaagtggaa acaaggagg cagtaactcc agaaaacgcc      1500
caaaaagtcc aaaatggcag caccagagac gggcaacacg ggctccacag gatccgctgg     1560
ctcgacagga tcgggatcgg atcgggatc gggaagtggg agctcctcag atccagcgaa      1620
tggacgggag gcccgtaacc ttgccgaaaa acagcgacgg gataagctta atgccagcat     1680
ccaggagctg gccaccatgg taccacatgc agccgaatcc tcccgtcgcc tggacaaaac     1740
cgccgtcctt agattcgcca cccatggcct gagacttcag tatgtctttg gcaagtccgc     1800
ttccagacgt cgcaagaaaa ccggcctcaa gggaacgggt atgtctgcct cacctgtcgg     1860
agatctaccc aatcccagtc tgcatctaac ggacactcta atgcaactgc tggactgctg     1920
cttcctcacc ctaacctgca gtggccaaat cgttttggta tccaccagcg tggagcagct     1980
attgggtcac tgtcagtccg atttgtatgg ccagaatcta ctgcagatca cgcatcccga     2040
tgatcaggat ctgttaagac agcagctaat acccagggat atagagaccc tgttctatca     2100
gcatcagcac caccagcagc aggggcacaa tccccagcag cactccactt ccacgtcggc     2160
ctcagcttcg ggcagtgatc tggaggagga ggaaatggag acggaggaac accgtctggg     2220
tcggcagcag ggagaggcgg acgatgacga ggatcacccg tacaacggac gaacacccag     2280
cccgcggaga atgggcccatt tggcgaccat tgatgaccga ctacgcatgg atcggcgctg     2340
ctttaccgtc cgcttggcta gggcttccac gcgagcggag gccacgcgtc attacgagcg     2400
ggttaagatc gatggctgct ttcgtcgcag tgactcctcc ttaaccggag gtgccgctgc     2460
caactatccg attgtctccc agctgatacg acgctcgaga aacaacaata tgctggctgc     2520
cgctgcagca gtggcagcag aagcggcgac ggtgccaccc cagcacgatg ccattgccca     2580
ggcggcgctg cacgggatta gcggcaatga tattgtcctg gtggccatgg ccagggtgct     2640
gcgagaggaa cggccgcctg aggagacgga gggtacagtg ggcttgacca tttacagaca     2700
gccagaaccc tatcagctgg agtaccatac gaggcatcta atcgacggca gcatcatcga     2760
ctgtgatcaa aggattggtc tggtggcggg atatatgaag gatgaggtgg gtatattaac     2820
atcatctctc tgaactgctt acgacaacta atcgtgtact ctccactcga aacaggtgcg     2880
caaccttagt cccttctgtt tcatgcacct ggacgacgtt cgctgggtga ttgtggccct     2940
tcgacaaatg tacgattgca acagtgacta tggcgagagc tgctaccgtc tgctgtcccg     3000
caacgggcgc ttcatttacc tgcacaccaa gggatttctg gaggtcgacc gtggcagtaa     3060
```

-continued

| | | |
|---|---|---|
| taaggtgcat tcctttctgt gcgtcaacac gctgctcgat gaggaggcgg gccggcaaaa | 3120 |
| ggtgcaggag atgaaggaga aattctcgac aatcatcaag gcggagatgc ccacgcagag | 3180 |
| cagcagtccc gatttgcccg cctcgcaggc accgcagcaa cttgagagaa ttgtcctcta | 3240 |
| tctaatagag aacctacaga agagtgtgga ttcagcagag acggttggcg gccagggcat | 3300 |
| ggaaagccta atggacgatg ctacagttcc gccagcaaat accttaactc tcgaggagtt | 3360 |
| agctccctcg cccacgcccg ccttggcctt ggtgccgccg gctccctcat cggtcaagag | 3420 |
| ctccatctcc aagtcggtga gtgtggtcaa tgtgacggcg gccagaaagt ttcagcagga | 3480 |
| gcatcagaag cagcgtgaac gtgaccgtga gcagcttaag gagcgcacca actccacgca | 3540 |
| gggcgtgatc cggcaactga gcagctgcct aagcgaggcg gaaacggcat cctgtatcct | 3600 |
| atcaccagcc agtagcttga gtgccagcga agcaccggac acgcccgatc cgcacagcaa | 3660 |
| cacatcaccg ccaccgtcgc tccacacacg tcccagtgtc ctgcatcgaa ccctgaccag | 3720 |
| cacgctgcga tgacgggctg atggaacctg gtttgccttc taattgggtg tgtggaaatg | 3780 |
| gacgtaattg gtagctcacg tgcccacaaa cgaattagta tcggtaatat aatcctggcc | 3840 |
| aatcgcaatg tgaaaaccca aaatgtatca gaaaaaaaac gagcattatt caaatagttt | 3900 |
| aaaaattcag ccaaaaaact taaatacgaa aaaaagagc gtgggttgaa gaaccttttg | 3960 |
| ttttcatatt cacatttcca agctttgagc aatcaaacaa ttttaatttt cagtatacac | 4020 |
| atatgtataa tgagttggct ttacaaaagc tattaacaaa tcaagcaatt gtgtaattta | 4080 |
| atatgagact ttccgtgatt tttgctttct acgtactttt cgacttcaat tgatctatag | 4140 |
| ggtttccgta ttaaaaacga aattaacgtg gtttcatttg atgaaaatgc aatatgagct | 4200 |
| cgcatttatt ttgatattat gacagtaata atgatctgat cacgataatc gttttctcaa | 4260 |
| aacataagcg atacattttg ggtacatttg gccattactg tttctgtgtg tgatttcggt | 4320 |
| ataaaatagt agtttgatta catgttatat tgatgaatgg cgatcggtgg gtgctgctaa | 4380 |
| atgcgttcca ttatcaataa ttttcgttat gtaattacgt ttaatttgta aatatgtatg | 4440 |
| agtgcgagcg tgagtgagtt tgtgatcgtg tcagcatggg tgtgaatgaa cattagatca | 4500 |
| gtgctcggat ttggttttag ttgaaattta accccatttt ccccgatttc ccagttatca | 4560 |
| ccttccgccc caaacacca ttgtaaaaag agtacaaaaa aaaaaaraaa agaaaataga | 4620 |
| aaaacaaaca aacaattata tatttatttc gccctaagtc tagaacgtgc taaacacaac | 4680 |
| tcattaatag ttaaacaaac ggatgttgca atcgatggaa attaaacgct cgcttttagt | 4740 |
| tttgccgtct cgctcgaaga aagaaagagg actactacat atgtacagtc aaactaatcc | 4800 |
| aagtcaaact cttcagtctc agaattggag actttattaa aggttttta ttttatgaag | 4860 |
| aatagcatat tattttata tatatatatt tatgtatata tatttatatc acaaatctcc | 4920 |
| ttcgatatcc ctttgtaatc tataaaaaca cttccaggcg cagctttatt tttcaacagt | 4980 |
| tttaattttg ggaactttac aaagcatata agcatacccc aaatccatat ccttataaac | 5040 |
| tttgtagtta ttacaaatgt gttcaaaatt aaaaaaaaaa aagtttgtca tccaaaatcc | 5100 |
| aatccgctaa atacaatata atcattttaa ttgatctatg ttacacttct ataatgtcta | 5160 |
| ctggacaaaa tatgattaag ttgaaatttc aaagtgtttt tgaagtttgt actaacgaag | 5220 |
| tttggctgta gttcaatact cacagaaagg gagcgagaca tattcccatc tcgctccgac | 5280 |
| ctgttatcaa agcctttgcc attgtccttg gcgttgcgtt cttatcaccg gcgtatcgga | 5340 |
| gggaatatat gatttttttt tcggccaagt ggttctagtg gtaaatatga agcggtgggt | 5400 |
| ggtttccggg ggtttggggg aaccgcggtt ggtgatgggc gcagagaagg cgggaagcgg | 5460 |

-continued

```
ggggggaacac gtttcgttat tttttgtttt atagcgaaat tcctctagct ataaatgtat    5520
gcatacatat atgctattaa cttttcgttt agctcaattt tttgtttgta ttttaatta      5580 taactcggtt tgtctagtgt gtaattaaat taaaagtcca atgctaattc cccagcgaat    5640
cgttcagtgt ttgttcaaac gagttgtgct ctttaaacac ttttggctta tcctttcatt    5700
taatttttgt ttgttttcct tgcgttgtta tatgtccaaa taaaaatgaa agtttgaatt    5760
gttttttttt agtaatttag ttttaactgt aatgtcaaat gtcgagaggt atactctgta    5820
taagaataat aatgtgtaat gtaattttta gaacttgcta atctctagca attaaaacat    5880
agcctgtaat taacaataat taattataat aaccagtaac agttcatgca aatgaaacct    5940
taataaataa taaattatat aaaagaagat ggaagtgttt tcaatcaatg aagttacttc    6000 ctatttcag gagttggaat gttacacttt tttataagct gatttgaaat gcgcgccaca     6060
ttatatctgc cttgcgcgca cgcattgcag ccgaataacg gcgaattaac tcccctcaga    6120
ggtgagtttg aactatcgat tataatcgat tgcattcgga aacaaaaaac accttgagtt    6180
tggtcagatc ggttttgcgc gggataaata ataaatatt aaatgttttc tttg           6234
```

<210> SEQ ID NO 2
<211> LENGTH: 3011
<212> TYPE: DNA
<213> ORGANISM: Met-JHR genomic DNA

<400> SEQUENCE: 2

```
ccaaaaataa gaaactaaaa gctgcaaaag taataaaaa tatattttag ccgaaaaatt      60
tccataataa caattctaga agtgcggagc gtacaccctg ttatggagag tgacgatttt    120
catttaccgc aaggcgccaa ttaaagggga aaatccataa atcgaggatt acaagtggaa    180
aacaaggagg cagtaactcc agaaaacgcc caaaaagtcc aaaatggcag caccagagac    240
gggcaacacg ggctccacag gatccgctgg ctcgacagga tcgggatcgg gatcgggatc    300
gggaagtggg agctcctcag atccagcgaa tggacgggag gcccgtaacc ttgccgaaaa    360
acagcgacgg gataagctta atgccagcat ccaggagctg gccaccatgg taccacatgc    420
agccgaatcc tcccgtcgcc tggacaaaac cgccgtcctt agattcgcca cccatggcct    480
gagacttcag tatgtctttg gcaagtccgc ttccagacgt cgcaagaaaa ccggcctcaa    540
gggaacgggt atgtctgcct cacctgtcgg agatctaccc aatcccagtc tgcatctaac    600
ggacactcta atgcaactgc tggactgctg cttcctcacc ctaacctgca gtggccaaat    660
cgttttggta tccaccagcg tggagcagct attgggtcac tgtcagtccg atttgtatgg    720
ccagaatcta ctgcagatca cgcatcccga tgatcaggat ctgttaagac agcagctaat    780
acccagggat atagagaccc tgttctatca gcatcagcac caccagcagc aggggcacaa    840
tccccagcag cactccactt ccacgtcggc ctcacttcg gcagtgatc tggaggagga     900 ggaaatggag acggaggaac accgtctggg tcggcagcag ggagaggcgg acgatgacga    960
ggatcacccg tacaaccgac gaacacccag cccgcggaga atggcccatt tggcgaccat    1020
tgatgaccga ctacgcatgg atcggcgctg ctttaccgtc cgcttggcta gggcttccac    1080
gcgagcggag gccacgcgtc attacgagcg ggttaagatc gatggctgct ttcgtcgcag    1140
tgactcctcc ttaaccggag gtgccgctgc caactatccg attgtctccc agctgatacg    1200
acgctcgaga acaacaaata tgctggctgc tgctgcagca gtggcagcag aagcggcgac    1260
ggtgccgccc cagcacgatg ccattgccca ggcggcgctg cacgggatta gcggcaatga    1320
```

-continued

```
tattgtcctg gtggccatgg ccagggtgct gcgagaggaa cggccgcctg aggagacgga      1380
gggtacagtg ggcttgacca tttacagaca gccagaaccc tatcagttgg agtaccatac      1440
gaggcatcta atcgacggca gcatcatcga ctgtgatcaa aggattggtc tggtggcggg      1500
atatatgaag gatgaggtgg gtatattaac atcatctctc tgaactgctt acgacaacta      1560
atcgtgtact ctccactcga aacaggtgcg caaccttagt cccttctgtt tcatgcacct      1620
ggacgacgtt cgctgggtga ttgtggccct tcgacaaatg tacgattgca acagtgacta      1680
cggcgagagc tgctaccgtc tgctgtcccg caacgggcgc ttcatttacc tgcacaccaa      1740
gggatttctg gaggtcgacc gtggcagtaa taaggtgcat tcctttctgt gcgtcaacac      1800
gctgctcgat gaggaggcgg gccggcaaaa ggtgcaggag atgaaggaga aattctcgac      1860
aatcatcaag gcggagatgc ccacgcagag cagcagtccc gatttgcccg cctcgcaggc      1920
accgcagcaa cttgagagaa ttgtcctcta tctaatagag aacctacaga agagtgtgga      1980
ttcagcagag acggttggcg gccagggcat ggaaagccta atggacgatg ctacagttc       2040 gccagcaaat accttaactc tcgaggagtt agctccctcg cccacgcccg ccttggcctt      2100
ggtgccgccg gctccctcat cggtcaagag ctccatctcc aagtcggtga gtgtggtcaa      2160
tgtgacggcg gccagaaagt ttcagcagga gcatcagaag cagcgtgaac gtgaccgtga      2220
gcagcttaag gagcgcacca actccacgca gggcgtgatc cggcaactga gcagctgcct      2280
aagcgaggcg gaaacggcat cctgtatcct atcaccagcc agtagcttga gtgccagcga      2340
agcaccggac acgcccgatc cgcacagcaa cacatcaccc ccaccgtcgc tccacacacg      2400
tcccagtgtc ctgcatcgaa ccctgaccag cacgctgcga tgacgggctg atggaacctg      2460
gtttgccttc taattgggtg tgtggaaatg gacgtaattg gtagctcacg tgcccacaaa      2520
cgaattagta tcggtaatat aatcctggcc aatcgcaatg tgaaacccca aaatgtatca      2580
gaaaaaaaac gagcattatt caaatagttt aaaaattcag ccaaaaaact aaaaacgaa       2640 aaaaagagc gtgggttgaa gaaccttttg ttttcatatt cacatttcca agctttgagc       2700
aatcaaacaa ttttaatttt cagtatacac atatgtataa tgagttggct ttacaaaagc      2760
tattaacaaa tcaagcaatt gtgtaattta atatgagact ttccgtgatt tttgctttct      2820
acgtactttt cgacttcaat tgatctatag ggtttccgta ttaaaaacga aattaacgtg      2880
gtttcatttg atgaaaatgc aatatgagct cgcatttatt ttgatattat gacagtaata      2940
atgatctgat cacgataatc gttttctcaa aacataagcg atacattttg ggtacatttg      3000
gccattactg t                                                           3011
```

<210> SEQ ID NO 3
<211> LENGTH: 3282
<212> TYPE: DNA
<213> ORGANISM: Met-JHR cDNA

<400> SEQUENCE: 3

```
aaataagaaa ctaaaagctg caaaagtaat aaaaaatata ttttagccga aaatttcca        60 taataacaat tctagaagtg cggagcgtac accctgttat ggagagtgac gattttcatt      120
taccgcaagg cgccaattaa agggaaaat ccataaatcg aggattacaa gtggaaaaca       180
aggaggcagt aactccagaa aacgcccaaa aagtccaaaa tggcagcacc agagacgggc     240
aacacgggct ccacaggatc cgctggctcg acaggatcgg gatcgggatc gggatcggga    300
agtgggagct cctcagatcc agcgaatgga cgggaggccc gtaaccttgc cgaaaaacag    360
cgacgggata agcttaatgc cagcatccag gagctggcta ccatggtacc acatgcagcc    420
```

```
gaatcctccc gtcgcctgga caaaaccgcc gtcctcagat ttgccaccca tggcctgaga    480
cttcagtatg tctttggcaa gtccgcttcc agacgtcgca agaaamccgg cctcaaggga    540
acgggtatgt ctgcctcacc tgtcggagat ctacccaatc ccagtctgca tctaacggac    600
actctaatgc aactgctgga ctgctgcttc ctcaccctaa cctgcagtgg ccaaatcgtt    660
ttggtatcca ccagcgtgga gcagctattg ggtcactgtc agtccgattt gtatggccag    720
aatctactgc agatcacgca tcccgatgat caggatctgt taagacagca gctaataccc    780
agggatatag agaccctgtt ctatcagcat cagcaccacc agcagcaggg gcacaatccc    840
cagcagcact ccacttccac gtcggcctca gcttcgggca gtgatctgga ggaggaggaa    900
atggagacgg aggaacaccg tctgggtcgg cagcaggag aggcggacga tgacgaggat    960
cacccgtaca accgacgaac acccagcccg cggagaatgg cccatttggc gaccattgat   1020
gaccgactac gcatggattg cgctgctttt accgtccgct ggctagggc ttccacgcga   1080 gcggaggcca cgcgtcatta cgagcgggtt aagatcgatg gctgctttcg tcgcagtgac   1140
tcctccttaa ccggaggtgc cgctgccaac tatccgattg tctcccagct gatacgacgc   1200
tcgagaaaca acaatatgct ggctgccgct gcagcagtgg cagcagaagc ggcgacggtg   1260
ccaccccagc acgatgccat tgcccaggcg gcgctgcacg ggattagcgg caatgatatt   1320
gtcctggtgg ccatggccag ggtgctgcga gaggaacggc cgcctgagga gacggagggt   1380
acagtgggct tgaccattta cagacagcca gaacctatc agctggagta ccatacgagg   1440
catctaatcg acggcagcat catcgactgt gatcaaagga ttggtctggt ggcgggatat   1500 atgaaggat gaggtgcgcaa ccttagtccc ttctgtttca tgcacctgga cgacgttcgc   1560
tgggtgattg tggcccttcg acaaatgtac gattgcaaca gtgactatgg cgagagctgc   1620
taccgtctgc tgtcccgcaa cgggcgcttc atttacctgc acaccaaggg atttctggag   1680
gtcgaccgtg gcagtaataa ggtgcattcc tttctgtgcg tcaacacgct gctcgatgag   1740
gaggcgggcc ggcaaaaggt gcaggagatg aaggagaaat tctcgacaat catcaaggcg   1800
gagatgccca cgcagagcag cagtcccgat ttgcccgcct cgcaggcacc gcagcaactt   1860
gagagaattg tcctctatct aatagagaac ctacagaaga gtgtggattc agcagagacg   1920
gttggcggcc agggcatgga aagcctaatg gacgatggct acagttcgcc agcaaatacc   1980
ttaactctcg aggagttagc tccctcgccc acgcccgcct tggccttggt gccgccggct   2040
ccctcatcgg tcaagagctc catctccaag tcggtgagtg tggtcaatgt gacggcggcc   2100
agaaagtttc agcaggagca tcagaagcag cgtgaacgtg accgtgagca gcttaaggag   2160
cgcaccaact ccacgcaggg cgtgatccgg caactgagca gctgcctaag cgaggcggaa   2220
acggcatcct gtatcctatc accagccagt agcttgagtg ccagcgaagc accggacacg   2280
cccgatccgc acagcaacac atcaccgcca ccgtcgctcc acacacgtcc cagtgtcctg   2340
catcgaaccc tgaccagcac gctgcgatga cgggctgatg gaacctggtt tgccttctaa   2400
ttgggtgtgt ggaaatggac gtaattggta gctcacgtgc ccacaaacga attagtatcg   2460
gtaatataat cctggccaat cgcaatgtga aacccaaaa tgtatcagaa aaaaacgag   2520 cattattcaa atagtttaaa aattcagcca aaaaacttaa aaacgaaaaa aagagcgtg   2580 ggttgaagaa ccttttgttt tcatattcac atttccaagc tttgagcaat caaacaattt   2640
taattttcag tatacacata tgtataatga gttggcttta caaagctat taacaaatca   2700 agcaattgtg taatttaata tgagactttc cgtgattttt gctttctacg tacttttcga   2760
```

-continued

```
cttcaattga tctatagggt ttccgtatta aaaacgaaat taacgtggtt tcatttgatg    2820
aaaatgcaat atgagctcgc atttattttg atattatgac agtaataatg atctgatcac    2880
gataatcgtt ttctcaaaac ataagcgata cattttgggt acatttggcc attactgttt    2940
ctgtgtgtga tttcggtata aaatagtagt ttgattacat gttatattga tgaatggcga    3000
tcggtgggtg ctgctaaatg cgttccatta tcaataattt tcgttatgta attacgttta    3060
atttgtaaat atgtatgagt gcgagcgtga gtgagtttgt gatcgtgtca gcatgggtgt    3120
gaatgaacat tagatcagtg ctcggatttg gttttagttg aaatttaaac cccatttccc    3180
cgatttccca gttatcacct tccgccccaa aacaccattg taaaagagt acaaaaaaaa    3240 aaagaaaaga aaatagaaaa acaaaaaaaa aaaaaaaaa aa                        3282
```

<210> SEQ ID NO 4
<211> LENGTH: 737
<212> TYPE: PRT
<213> ORGANISM: Met-JHR
<220> FEATURE:
<223> OTHER INFORMATION: Xaa at position 218 may be Thr or Pro

<400> SEQUENCE: 4

```
Met Ala Ala Pro Glu Thr Gly Asn Thr Gly Ser Thr Gly Ser Ala Gly
 1               5                  10                  15

Ser Thr Gly Ser Gly Ser Gly Ser Gly Ser Gly Ser Ser Ser
                20                  25                  30

Asp Pro Ala Asn Gly Arg Glu Ala Arg Asn Leu Ala Glu Lys Gln Arg
            35                  40                  45

Arg Asp Lys Leu Asn Ala Ser Ile Gln Glu Leu Ala Thr Met Val Pro
        50                  55                  60

His Ala Ala Glu Ser Ser Arg Arg Leu Asp Lys Thr Ala Val Leu Arg
    65                  70                  75                  80

Phe Ala Thr His Gly Leu Arg Leu Gln Tyr Val Phe Gly Lys Ser Ala
                85                  90                  95

Ser Arg Arg Arg Lys Lys Thr Gly Leu Lys Gly Thr Gly Met Ser Ala
            100                 105                 110

Ser Pro Val Gly Asp Leu Pro Asn Pro Ser Leu His Leu Thr Asp Thr
        115                 120                 125

Leu Met Gln Leu Leu Asp Cys Cys Phe Leu Thr Leu Thr Cys Ser Gly
    130                 135                 140

Gln Ile Val Leu Val Ser Thr Ser Val Glu Gln Leu Leu Gly His Cys
145                 150                 155                 160

Gln Ser Asp Leu Tyr Gly Gln Asn Leu Leu Gln Ile Thr His Pro Asp
                165                 170                 175

Asp Gln Asp Leu Leu Arg Gln Gln Leu Ile Pro Arg Asp Ile Glu Thr
            180                 185                 190

Leu Phe Tyr Gln His Gln His His Gln Gln Gln Gly His Asn Pro Gln
        195                 200                 205

Gln His Ser Thr Ser Thr Ser Ala Ser Xaa Ser Gly Ser Asp Leu Glu
    210                 215                 220

Glu Glu Glu Met Glu Thr Glu Glu His Arg Leu Gly Arg Gln Gln Gly
225                 230                 235                 240

Glu Ala Asp Asp Asp Glu Asp His Pro Tyr Asn Arg Arg Thr Pro Ser
                245                 250                 255

Pro Arg Arg Met Ala His Leu Ala Thr Ile Asp Asp Arg Leu Arg Met
            260                 265                 270
```

```
Asp Arg Arg Cys Phe Thr Val Arg Leu Ala Arg Ala Ser Thr Arg Ala
            275                 280                 285

Glu Ala Thr Arg His Tyr Glu Arg Val Lys Ile Asp Gly Cys Phe Arg
            290                 295                 300

Arg Ser Asp Ser Ser Leu Thr Gly Gly Ala Ala Ala Asn Tyr Pro Ile
305                 310                 315                 320

Val Ser Gln Leu Ile Arg Arg Ser Arg Asn Asn Asn Met Leu Ala Ala
                325                 330                 335

Ala Ala Ala Val Ala Ala Glu Ala Ala Thr Val Pro Pro Gln His Asp
            340                 345                 350

Ala Ile Ala Gln Ala Ala Leu His Gly Ile Ser Gly Asn Asp Ile Val
            355                 360                 365

Leu Val Ala Met Ala Arg Val Leu Arg Glu Glu Arg Pro Pro Glu Glu
    370                 375                 380

Thr Glu Gly Thr Val Gly Leu Thr Ile Tyr Arg Gln Pro Glu Pro Tyr
385                 390                 395                 400

Gln Leu Glu Tyr His Thr Arg His Leu Ile Asp Gly Ser Ile Ile Asp
                405                 410                 415

Cys Asp Gln Arg Ile Gly Leu Val Ala Gly Tyr Met Lys Asp Glu Val
                420                 425                 430

Gly Ile Leu Thr Ser Ser Leu Thr Ala Tyr Asp Asn Ser Cys Thr Leu
            435                 440                 445

His Ser Lys Gln Val Arg Asn Leu Ser Pro Phe Cys Phe Met His Leu
    450                 455                 460

Asp Asp Val Arg Trp Val Ile Val Ala Leu Arg Gln Met Tyr Asp Cys
465                 470                 475                 480

Asn Ser Asp Tyr Gly Glu Ser Cys Tyr Arg Leu Leu Ser Arg Asn Gly
                485                 490                 495

Arg Phe Ile Tyr Leu His Thr Lys Gly Phe Leu Glu Val Asp Arg Gly
                500                 505                 510

Ser Asn Lys Val His Ser Phe Leu Cys Val Asn Thr Leu Leu Asp Glu
            515                 520                 525

Glu Ala Gly Arg Gln Lys Val Gln Glu Met Lys Glu Lys Phe Ser Thr
    530                 535                 540

Ile Ile Lys Ala Glu Met Pro Thr Gln Ser Ser Pro Asp Leu Pro
545                 550                 555                 560

Ala Ser Gln Ala Pro Gln Gln Leu Glu Arg Ile Val Leu Tyr Leu Ile
                565                 570                 575

Glu Asn Leu Gln Lys Ser Val Asp Ser Ala Glu Thr Val Gly Gly Gln
            580                 585                 590

Gly Met Glu Ser Leu Met Asp Asp Gly Tyr Ser Ser Pro Ala Asn Thr
    595                 600                 605

Leu Thr Leu Glu Glu Leu Ala Pro Ser Pro Thr Pro Ala Leu Ala Leu
    610                 615                 620

Val Pro Pro Ala Pro Ser Ser Val Lys Ser Ser Ile Ser Lys Ser Val
625                 630                 635                 640

Ser Val Val Asn Val Thr Ala Ala Arg Lys Phe Gln Gln Glu His Gln
                645                 650                 655

Lys Gln Arg Glu Arg Asp Arg Glu Gln Leu Lys Glu Arg Thr Asn Ser
                660                 665                 670

Thr Gln Gly Val Ile Arg Gln Leu Ser Ser Cys Leu Ser Glu Ala Glu
            675                 680                 685

Thr Ala Ser Cys Ile Leu Ser Pro Ala Ser Ser Leu Ser Ala Ser Glu
```

```
              690                 695                 700
Ala Pro Asp Thr Pro Asp Pro His Ser Asn Thr Ser Pro Pro Ser
705                 710                 715                 720

Leu His Thr Arg Pro Ser Val Leu His Arg Thr Leu Thr Ser Thr Leu
                725                 730                 735

Arg

<210> SEQ ID NO 5
<211> LENGTH: 716
<212> TYPE: PRT
<213> ORGANISM: Met-JHR
<220> FEATURE:
<223> OTHER INFORMATION: Xaa at position 103 may be Gly or Arg

<400> SEQUENCE: 5

Met Ala Ala Pro Glu Thr Gly Asn Thr Gly Ser Thr Gly Ser Ala Gly
  1               5                  10                  15

Ser Thr Gly Ser Gly Ser Gly Ser Gly Ser Gly Ser Gly Ser Ser Ser
                 20                  25                  30

Asp Pro Ala Asn Gly Arg Glu Ala Arg Asn Leu Ala Glu Lys Gln Arg
             35                  40                  45

Arg Asp Lys Leu Asn Ala Ser Ile Gln Glu Leu Ala Thr Met Val Pro
     50                  55                  60

His Ala Ala Glu Ser Ser Arg Arg Leu Asp Lys Thr Ala Val Leu Arg
 65                  70                  75                  80

Phe Ala Thr His Gly Leu Arg Leu Gln Tyr Val Phe Gly Lys Ser Ala
                 85                  90                  95

Ser Arg Arg Arg Lys Lys Xaa Gly Leu Lys Gly Thr Gly Met Ser Ala
            100                 105                 110

Ser Pro Val Gly Asp Leu Pro Asn Pro Ser Leu His Leu Thr Asp Thr
        115                 120                 125

Leu Met Gln Leu Leu Asp Cys Cys Phe Leu Thr Leu Thr Cys Ser Gly
130                 135                 140

Gln Ile Val Leu Val Ser Thr Ser Val Glu Gln Leu Leu Gly His Cys
145                 150                 155                 160

Gln Ser Asp Leu Tyr Gly Gln Asn Leu Leu Gln Ile Thr His Pro Asp
                165                 170                 175

Asp Gln Asp Leu Leu Arg Gln Gln Leu Ile Pro Arg Asp Ile Glu Thr
            180                 185                 190

Leu Phe Tyr Gln His Gln His His Gln Gln Gln Gly His Asn Pro Gln
        195                 200                 205

Gln His Ser Thr Ser Thr Ser Ala Ser Ala Ser Gly Ser Asp Leu Glu
210                 215                 220

Glu Glu Glu Met Glu Thr Glu Glu His Arg Leu Gly Arg Gln Gln Gly
225                 230                 235                 240

Glu Ala Asp Asp Asp Glu Asp His Pro Tyr Asn Arg Arg Thr Pro Ser
                245                 250                 255

Pro Arg Arg Met Ala His Leu Ala Thr Ile Asp Asp Arg Leu Arg Met
            260                 265                 270

Asp Trp Arg Cys Phe Thr Val Arg Leu Ala Arg Ala Ser Thr Arg Ala
        275                 280                 285

Glu Ala Thr Arg His Tyr Glu Arg Val Lys Ile Asp Gly Cys Phe Arg
290                 295                 300

Arg Ser Asp Ser Ser Leu Thr Gly Gly Ala Ala Ala Asn Tyr Pro Ile
305                 310                 315                 320
```

-continued

```
Val Ser Gln Leu Ile Arg Arg Ser Arg Asn Asn Asn Met Leu Ala Ala
            325                 330                 335

Ala Ala Ala Val Ala Ala Glu Ala Ala Thr Val Pro Pro Gln His Asp
            340                 345                 350

Ala Ile Ala Gln Ala Ala Leu His Gly Ile Ser Gly Asn Asp Ile Val
            355                 360                 365

Leu Val Ala Met Ala Arg Val Leu Arg Glu Glu Arg Pro Pro Glu Glu
        370                 375                 380

Thr Glu Gly Thr Val Gly Leu Thr Ile Tyr Arg Gln Pro Glu Pro Tyr
385                 390                 395                 400

Gln Leu Glu Tyr His Thr Arg His Leu Ile Asp Gly Ser Ile Ile Asp
            405                 410                 415

Cys Asp Gln Arg Ile Gly Leu Val Ala Gly Tyr Met Lys Asp Glu Val
            420                 425                 430

Arg Asn Leu Ser Pro Phe Cys Phe Met His Leu Asp Asp Val Arg Trp
            435                 440                 445

Val Ile Val Ala Leu Arg Gln Met Tyr Asp Cys Asn Ser Asp Tyr Gly
        450                 455                 460

Glu Ser Cys Tyr Arg Leu Leu Ser Arg Asn Gly Arg Phe Ile Tyr Leu
465                 470                 475                 480

His Thr Lys Gly Phe Leu Glu Val Asp Arg Gly Ser Asn Lys Val His
            485                 490                 495

Ser Phe Leu Cys Val Asn Thr Leu Leu Asp Glu Ala Gly Arg Gln
            500                 505                 510

Lys Val Gln Glu Met Lys Glu Lys Phe Ser Thr Ile Ile Lys Ala Glu
            515                 520                 525

Met Pro Thr Gln Ser Ser Pro Asp Leu Pro Ala Ser Gln Ala Pro
        530                 535                 540

Gln Gln Leu Glu Arg Ile Val Leu Tyr Leu Ile Glu Asn Leu Gln Lys
545                 550                 555                 560

Ser Val Asp Ser Ala Glu Thr Val Gly Gly Gln Gly Met Glu Ser Leu
            565                 570                 575

Met Asp Asp Gly Tyr Ser Ser Pro Ala Asn Thr Leu Thr Leu Glu Glu
            580                 585                 590

Leu Ala Pro Ser Pro Thr Pro Ala Leu Ala Leu Val Pro Pro Ala Pro
            595                 600                 605

Ser Ser Val Lys Ser Ser Ile Ser Lys Ser Val Ser Val Asn Val
            610                 615                 620

Thr Ala Ala Arg Lys Phe Gln Gln Glu His Gln Lys Gln Arg Glu Arg
625                 630                 635                 640

Asp Arg Glu Gln Leu Lys Glu Arg Thr Asn Ser Thr Gln Gly Val Ile
            645                 650                 655

Arg Gln Leu Ser Ser Cys Leu Ser Glu Ala Glu Thr Ala Ser Cys Ile
            660                 665                 670

Leu Ser Pro Ala Ser Ser Leu Ser Ala Ser Glu Ala Pro Asp Thr Pro
            675                 680                 685

Asp Pro His Ser Asn Thr Ser Pro Pro Ser Leu His Thr Arg Pro
            690                 695                 700

Ser Val Leu His Arg Thr Leu Thr Ser Thr Leu Arg
705                 710                 715
```

<210> SEQ ID NO 6
<211> LENGTH: 250

```
<212> TYPE: DNA
<213> ORGANISM: D. melanogaster

<400> SEQUENCE: 6
atggcagcac cagagacggg caacacgggc tccacaggat ccgctggctc gacaggatcg      60
ggatcgggat cgggatcggg aagtgggagc tcctcagatc cagcgaatgg acggaggcc     120 cgtaaccttg ccgaaaaaca gcgacgggat aagcttaatg ccagcatcca ggagctggct    180
accatggtac cacatgcagc cgaatcctcc cgtcgcctgg acaaaaccgc cgtccttaga    240
ttcgccaccc                                                           250

<210> SEQ ID NO 7
<211> LENGTH: 232
<212> TYPE: DNA
<213> ORGANISM: D. erecta

<400> SEQUENCE: 7
cagcagacgc gggcaacacg ggcaccacag gatcagctgg gtccacagga tcgggatcgg      60
gaactgggac gtccgcagat ccagcgaatg acgggaggc ccgcaatctt gccgagaaac     120
agcgacggga taagcttaat gccagcatcc aggagctggc taccatggta ccacatgtca    180
gccgaatcct cccgacgcct ggacaaaacc gccgtcctca gattcgccac cc            232

<210> SEQ ID NO 8
<211> LENGTH: 631
<212> TYPE: PRT
<213> ORGANISM: Drosophila

<400> SEQUENCE: 8

Met Asp Glu Ala Asn Ile Gln Asp Lys Glu Arg Phe Ala Ser Arg Glu
  1               5                  10                  15

Asn His Cys Glu Ile Glu Arg Arg Arg Asn Lys Met Thr Ala Tyr
             20                  25                  30

Ile Thr Glu Leu Ser Asp Met Val Pro Thr Cys Ser Ala Leu Ala Arg
         35                  40                  45

Lys Pro Asp Lys Leu Thr Ile Leu Arg Met Ala Val Ala His Met Lys
     50                  55                  60

Ala Leu Arg Gly Thr Gly Asn Thr Ser Ser Asp Gly Thr Tyr Lys Pro
 65                  70                  75                  80

Ser Phe Leu Thr Asp Gln Glu Leu Lys His Leu Ile Leu Glu Ala Ala
                 85                  90                  95

Asp Gly Phe Leu Phe Val Val Ser Cys Asp Ser Gly Arg Val Ile Tyr
            100                 105                 110

Val Ser Asp Ser Val Thr Pro Val Leu Asn Tyr Thr Gln Ser Asp Trp
        115                 120                 125

Tyr Gly Thr Ser Leu Tyr Glu His Ile His Pro Asp Asp Arg Glu Lys
    130                 135                 140

Ile Arg Glu Gln Leu Ser Thr Gln Glu Ser Gln Asn Ala Gly Arg Ile
145                 150                 155                 160

Leu Asp Leu Lys Ser Gly Thr Val Lys Lys Glu Gly His Gln Ser Ser
                165                 170                 175

Met Arg Leu Ser Met Gly Ala Arg Arg Gly Phe Ile Cys Met Arg Val
            180                 185                 190

Gly Asn Val Asn Pro Glu Ser Met Val Ser Gly His Leu Asn Arg Leu
        195                 200                 205

Lys Gln Arg Asn Ser Leu Gly Pro Ser Arg Asp Gly Thr Asn Tyr Ala
```

-continued

```
            210                 215                 220
Val Val His Cys Thr Gly Tyr Ile Lys Asn Trp Pro Thr Asp Met
225                 230                 235                 240

Phe Pro Asn Met His Met Glu Arg Asp Val Asp Met Ser Ser His
                245                 250                 255

Cys Cys Leu Val Ala Ile Gly Arg Leu Gln Val Thr Ser Thr Ala Ala
                260                 265                 270

Asn Asp Met Ser Gly Ser Asn Asn Gln Ser Glu Phe Ile Thr Arg His
                275                 280                 285

Ala Met Asp Gly Lys Phe Thr Phe Val Asp Gln Arg Val Leu Asn Ile
290                 295                 300

Leu Gly Tyr Thr Pro Thr Glu Leu Leu Gly Lys Ile Cys Tyr Asp Phe
305                 310                 315                 320

Phe His Pro Glu Asp Gln Ser His Met Lys Glu Ser Phe Asp Gln Val
                325                 330                 335

Leu Lys Gln Lys Gly Gln Met Phe Ser Leu Leu Tyr Arg Ala Arg Ala
                340                 345                 350

Lys Asn Ser Glu Tyr Tyr Val Trp Leu Arg Thr Gln Ala Tyr Ala Phe
                355                 360                 365

Leu Asn Pro Tyr Thr Asp Glu Val Glu Tyr Ile Val Cys Thr Asn Ser
370                 375                 380

Ser Gly Lys Thr Met His Gly Ala Pro Leu Asp Ala Ala Ala His
385                 390                 395                 400

Thr Pro Glu Gln Val Gln Gln Gln Gln Gln Gln Gln Glu Gln His
                405                 410                 415

Val Tyr Val Gln Ala Ala Pro Gly Val Asp Tyr Ala Arg Arg Glu Leu
                420                 425                 430

Thr Pro Val Gly Ser Ala Thr Asn Asp Gly Met Tyr Gln Thr His Met
                435                 440                 445

Leu Ala Met Gln Ala Pro Thr Pro Gln Gln Gln Gln Gln Gln Gln
                450                 455                 460

Arg Pro Gly Ser Ala Gln Thr Thr Pro Val Gly Tyr Thr Tyr Asp Thr
465                 470                 475                 480

Thr His Ser Pro Tyr Ser Ala Gly Gly Thr Ser Pro Leu Ala Lys Ile
                485                 490                 495

Pro Lys Ser Gly Thr Ser Pro Thr Pro Val Ala Pro Asn Ser Trp Ala
                500                 505                 510

Ala Leu Arg Pro Gln Gln Gln Gln Gln Gln Gln Pro Val Thr Glu
                515                 520                 525

Gly Tyr Gln Tyr Gln Gln Thr Ser Pro Ala Arg Ser Pro Ser Gly Pro
                530                 535                 540

Thr Tyr Thr Gln Leu Ser Ala Gly Asn Gly Asn Arg Gln Gln Ala Gln
545                 550                 555                 560

Pro Gly Ala Tyr Gln Ala Gly Pro Pro Pro Asn Ala Pro Gly
                565                 570                 575

Met Trp Asp Trp Gln Gln Ala Gly Gly His Pro His Pro Pro His Pro
                580                 585                 590

Thr Ala His Pro His His Pro His Ala His Pro Gly Gly Pro Ala Gly
                595                 600                 605

Ala Gly Gln Pro Gln Gly Gln Gly Val Leu Arg Tyr Ala Ala Asp Val
                610                 615                 620

Gly Ser His Ala Asp His Val
625                 630
```

```
<210> SEQ ID NO 9
<211> LENGTH: 789
<212> TYPE: PRT
<213> ORGANISM: human

<400> SEQUENCE: 9

Met Ala Ala Thr Thr Ala Asn Pro Glu Met Thr Ser Asp Val Pro Ser
 1               5                  10                  15

Leu Gly Pro Ala Ile Ala Ser Gly Asn Ser Gly Pro Gly Ile Gln Gly
                20                  25                  30

Gly Gly Ala Ile Val Gln Arg Ala Ile Lys Arg Arg Pro Gly Leu Asp
            35                  40                  45

Phe Asp Asp Asp Gly Glu Gly Asn Ser Lys Phe Leu Arg Cys Asp Asp
 50                  55                  60

Asp Gln Met Ser Asn Asp Lys Glu Arg Phe Ala Arg Ser Asp Asp Glu
 65                  70                  75                  80

Gln Ser Ser Ala Asp Lys Glu Arg Leu Ala Arg Glu Asn His Ser Glu
                85                  90                  95

Ile Glu Arg Arg Arg Arg Asn Lys Met Thr Ala Tyr Ile Thr Glu Leu
            100                 105                 110

Ser Asp Met Val Pro Thr Cys Ser Ala Leu Ala Arg Lys Pro Asp Lys
        115                 120                 125

Leu Thr Ile Leu Arg Met Ala Val Ser His Met Lys Ser Leu Arg Gly
130                 135                 140

Thr Gly Asn Thr Ser Thr Asp Gly Ser Tyr Lys Pro Ser Phe Leu Thr
145                 150                 155                 160

Asp Gln Glu Leu Lys His Leu Ile Leu Glu Ala Ala Asp Gly Phe Leu
                165                 170                 175

Phe Ile Val Ser Cys Glu Thr Gly Arg Val Val Tyr Val Ser Asp Ser
            180                 185                 190

Val Thr Pro Val Leu Asn Gln Pro Gln Ser Glu Trp Phe Gly Ser Thr
        195                 200                 205

Leu Tyr Asp Gln Val His Pro Asp Asp Val Asp Lys Leu Arg Glu Gln
210                 215                 220

Leu Ser Thr Ser Glu Asn Ala Leu Thr Gly Arg Ile Leu Asp Leu Lys
225                 230                 235                 240

Thr Gly Thr Val Lys Lys Glu Gly Gln Gln Ser Ser Met Arg Met Cys
                245                 250                 255

Met Gly Ser Arg Arg Ser Phe Ile Cys Arg Met Arg Cys Gly Ser Ser
            260                 265                 270

Ser Val Asp Pro Val Ser Val Asn Arg Leu Ser Phe Val Arg Asn Arg
        275                 280                 285

Cys Arg Asn Gly Leu Gly Ser Val Lys Asp Gly Glu Pro His Phe Val
290                 295                 300

Val Val His Cys Thr Gly Tyr Ile Lys Ala Trp Pro Pro Ala Gly Val
305                 310                 315                 320

Ser Leu Pro Asp Asp Asp Pro Glu Ala Gly Gln Gly Ser Lys Phe Cys
                325                 330                 335

Leu Val Ala Ile Gly Arg Leu Gln Val Thr Ser Ser Pro Asn Cys Thr
            340                 345                 350

Asp Met Ser Asn Val Cys Gln Pro Thr Glu Phe Ile Ser Arg His Asn
        355                 360                 365

Ile Glu Gly Ile Phe Thr Phe Val Asp His Arg Cys Val Ala Thr Val
```

```
              370                 375                 380
Gly Tyr Gln Pro Gln Glu Leu Leu Gly Lys Asn Ile Val Glu Phe Cys
385                 390                 395                 400

His Pro Glu Asp Gln Gln Leu Leu Arg Asp Ser Phe Gln Gln Val Val
                405                 410                 415

Lys Leu Lys Gly Gln Val Leu Ser Val Met Phe Arg Phe Arg Ser Lys
                420                 425                 430

Asn Gln Glu Trp Leu Trp Met Arg Thr Ser Ser Phe Thr Phe Gln Asn
                435                 440                 445

Pro Tyr Ser Asp Glu Ile Glu Tyr Ile Ile Cys Thr Asn Thr Asn Val
        450                 455                 460

Lys Asn Ser Ser Gln Glu Pro Arg Pro Thr Leu Ser Asn Thr Ile Gln
465                 470                 475                 480

Arg Pro Gln Leu Gly Pro Thr Ala Asn Leu Pro Leu Glu Met Gly Ser
                485                 490                 495

Gly Gln Leu Ala Pro Arg Gln Gln Gln Gln Thr Glu Leu Asp Met
                500                 505                 510

Val Pro Gly Arg Asp Gly Leu Ala Ser Tyr Asn His Ser Gln Val Val
        515                 520                 525

Gln Pro Val Thr Thr Thr Gly Pro Glu His Ser Lys Pro Leu Glu Lys
        530                 535                 540

Ser Asp Gly Leu Phe Ala Gln Asp Arg Asp Pro Arg Phe Ser Glu Ile
545                 550                 555                 560

Tyr His Asn Ile Asn Ala Asp Gln Ser Lys Gly Ile Ser Ser Thr
                565                 570                 575

Val Pro Ala Thr Gln Gln Leu Phe Ser Gln Gly Asn Thr Phe Pro Pro
                580                 585                 590

Thr Pro Arg Pro Ala Glu Asn Phe Arg Asn Ser Gly Leu Ala Pro Pro
        595                 600                 605

Val Thr Ile Val Gln Pro Ser Ala Ser Ala Gly Gln Met Leu Ala Gln
        610                 615                 620

Ile Ser Arg His Ser Asn Pro Thr Gln Gly Ala Thr Pro Thr Trp Thr
625                 630                 635                 640

Pro Thr Thr Arg Ser Gly Phe Ser Ala Gln Gln Val Ala Thr Gln Ala
                645                 650                 655

Thr Ala Lys Thr Arg Thr Ser Gln Phe Gly Val Gly Ser Phe Gln Thr
                660                 665                 670

Pro Ser Ser Phe Ser Ser Met Ser Leu Pro Gly Ala Pro Thr Ala Ser
                675                 680                 685

Pro Gly Ala Ala Ala Tyr Pro Ser Leu Thr Asn Arg Gly Ser Asn Phe
        690                 695                 700

Ala Pro Glu Thr Gly Gln Thr Ala Gly Gln Phe Gln Thr Arg Thr Ala
705                 710                 715                 720

Glu Gly Val Gly Val Trp Pro Gln Trp Gln Gly Gln Pro His His
                725                 730                 735

Arg Ser Ser Ser Glu Gln His Val Gln Gln Pro Ala Gln Gln
                740                 745                 750

Pro Gly Gln Pro Glu Val Phe Gln Glu Met Leu Ser Met Leu Gly Asp
                755                 760                 765

Gln Ser Asn Ser Tyr Asn Asn Glu Glu Phe Pro Asp Leu Thr Met Phe
        770                 775                 780

Pro Pro Phe Ser Glu
785
```

<210> SEQ ID NO 10
<211> LENGTH: 626
<212> TYPE: PRT
<213> ORGANISM: brain and muscle ARNT-like protein a

<400> SEQUENCE: 10

```
Met Ala Asp Gln Arg Met Asp Ile Ser Ser Thr Ile Ser Asp Phe Met
 1               5                  10                  15

Ser Pro Gly Pro Thr Asp Leu Leu Ser Ser Leu Gly Thr Ser Gly
                20                  25                  30

Val Asp Cys Asn Arg Lys Arg Lys Gly Ser Ser Thr Asp Tyr Gln Glu
            35                  40                  45

Ser Met Asp Thr Asp Lys Asp Pro His Gly Arg Leu Glu Tyr Thr
    50                  55                  60

Glu His Gln Gly Arg Ile Lys Asn Ala Arg Glu Ala His Ser Gln Ile
 65                  70                  75                  80

Glu Lys Arg Arg Arg Asp Lys Met Asn Ser Phe Ile Asp Glu Leu Ala
                85                  90                  95

Ser Leu Val Pro Thr Cys Asn Ala Met Ser Arg Lys Leu Asp Lys Leu
            100                 105                 110

Thr Val Leu Arg Met Ala Val Gln His Met Arg Thr Leu Arg Gly Ala
        115                 120                 125

Thr Asn Pro Tyr Thr Glu Ala Asn Tyr Lys Pro Thr Phe Leu Ser Asp
    130                 135                 140

Asp Glu Leu Lys His Leu Ile Leu Arg Ala Ala Asp Gly Phe Leu Phe
145                 150                 155                 160

Val Val Gly Cys Asp Arg Gly Lys Ile Leu Phe Val Ser Glu Ser Val
                165                 170                 175

Phe Lys Ile Leu Asn Tyr Ser Gln Asn Asp Leu Ile Gly Gln Ser Leu
            180                 185                 190

Phe Asp Tyr Leu His Pro Lys Asp Ile Ala Lys Val Lys Glu Gln Leu
        195                 200                 205

Ser Ser Ser Asp Thr Ala Pro Arg Glu Arg Leu Ile Asp Ala Lys Thr
    210                 215                 220

Gly Leu Pro Val Lys Thr Asp Ile Thr Pro Gly Pro Ser Arg Leu Cys
225                 230                 235                 240

Ser Gly Ala Arg Arg Ser Phe Phe Cys Arg Met Lys Cys Asn Arg Pro
                245                 250                 255

Ser Val Lys Val Glu Asp Lys Asp Phe Pro Ser Thr Cys Ser Lys Lys
            260                 265                 270

Lys Ala Asp Arg Lys Ser Phe Cys Thr Ile His Ser Thr Gly Tyr Leu
        275                 280                 285

Lys Ser Trp Pro Pro Thr Lys Met Gly Leu Asp Glu Asp Asn Glu Pro
    290                 295                 300

Asp Asn Glu Gly Cys Asn Leu Ser Cys Leu Val Ala Ile Gly Arg Leu
305                 310                 315                 320

His Ser His Val Val Pro Gln Pro Val Asn Gly Glu Ile Arg Val Lys
                325                 330                 335

Ser Met Glu Tyr Val Ser Arg His Ala Ile Asp Gly Lys Phe Val Phe
            340                 345                 350

Val Asp Gln Arg Ala Thr Ala Ile Leu Ala Tyr Leu Pro Gln Glu Leu
        355                 360                 365

Leu Gly Thr Ser Cys Tyr Glu Tyr Phe His Gln Asp Asp Ile Gly His
```

```
                370              375              380
Leu Ala Glu Cys His Arg Gln Val Leu Gln Thr Arg Glu Lys Ile Thr
385              390              395              400

Thr Asn Cys Tyr Lys Phe Lys Ile Lys Asp Gly Ser Phe Ile Thr Leu
                405              410              415

Arg Ser Arg Trp Phe Ser Phe Met Asn Pro Trp Thr Lys Glu Val Glu
            420              425              430

Tyr Ile Val Ser Thr Asn Thr Val Leu Ala Asn Val Leu Glu Gly
            435              440              445

Gly Asp Pro Thr Phe Pro Gln Leu Thr Ala Ser Pro His Ser Met Asp
        450              455              460

Ser Met Leu Pro Ser Gly Glu Gly Pro Lys Arg Thr His Pro Thr
465              470              475              480

Val Pro Gly Ile Pro Gly Gly Thr Arg Ala Gly Ala Gly Lys Ile Gly
                485              490              495

Arg Met Ile Ala Glu Glu Ile Met Glu Ile His Arg Ile Arg Gly Ser
            500              505              510

Ser Pro Ser Ser Cys Gly Ser Ser Pro Leu Asn Ile Thr Ser Thr Pro
        515              520              525

Pro Pro Asp Ala Ser Ser Pro Gly Gly Lys Lys Ile Leu Asn Gly Gly
        530              535              540

Thr Pro Asp Ile Pro Ser Ser Gly Leu Leu Ser Gly Gln Ala Gln Glu
545              550              555              560

Asn Pro Gly Tyr Pro Tyr Ser Asp Ser Ser Ile Leu Gly Glu Asn
            565              570              575

Pro His Ile Gly Ile Asp Met Ile Asp Asn Asp Gln Gly Ser Ser Ser
        580              585              590

Pro Ser Asn Asp Glu Ala Ala Met Ala Val Ile Met Ser Leu Leu Glu
        595              600              605

Ala Asp Ala Gly Leu Gly Gly Pro Val Asp Phe Ser Asp Leu Pro Trp
        610              615              620

Pro Leu
625

<210> SEQ ID NO 11
<211> LENGTH: 716
<212> TYPE: PRT
<213> ORGANISM: Met-JHR

<400> SEQUENCE: 11

Met Ala Ala Pro Glu Thr Gly Asn Thr Gly Ser Thr Gly Ser Ala Gly
1               5               10              15

Ser Thr Gly Ser Gly Ser Gly Ser Gly Ser Gly Ser Ser Ser
                20              25              30

Asp Pro Ala Asn Gly Arg Glu Ala Arg Asn Leu Ala Glu Lys Gln Arg
            35              40              45

Arg Asp Lys Leu Asn Ala Ser Ile Gln Glu Leu Ala Thr Met Val Pro
        50              55              60

His Ala Glu Ser Ser Arg Arg Leu Asp Lys Thr Ala Val Leu Arg
65              70              75              80

Phe Ala Thr His Gly Leu Arg Leu Gln Tyr Val Phe Gly Lys Ser Ala
            85              90              95

Ser Arg Arg Arg Lys Lys Pro Gly Leu Lys Gly Thr Gly Met Ser Ala
            100             105             110
```

```
Ser Pro Val Gly Asp Leu Pro Asn Pro Ser Leu His Leu Thr Asp Thr
        115                 120                 125

Leu Met Gln Leu Leu Asp Cys Cys Phe Leu Thr Leu Thr Cys Ser Gly
    130                 135                 140

Gln Ile Val Leu Val Ser Thr Ser Val Glu Gln Leu Leu Gly His Cys
145                 150                 155                 160

Gln Ser Asp Leu Tyr Gly Gln Asn Leu Leu Gln Ile Thr His Pro Asp
                165                 170                 175

Asp Gln Asp Leu Leu Arg Gln Gln Leu Ile Pro Arg Asp Ile Glu Thr
            180                 185                 190

Leu Phe Tyr Gln His Gln His His Gln Gln Gln Gly His Asn Pro Gln
            195                 200                 205

Gln His Ser Thr Ser Thr Ser Ala Ser Ala Ser Gly Ser Asp Leu Glu
    210                 215                 220

Glu Glu Glu Met Glu Thr Glu His Arg Leu Gly Arg Gln Gln Gly
225                 230                 235                 240

Glu Ala Asp Asp Asp Glu Asp His Pro Tyr Asn Arg Arg Thr Pro Ser
                245                 250                 255

Pro Arg Arg Met Ala His Leu Ala Thr Ile Asp Asp Arg Leu Arg Met
            260                 265                 270

Asp Trp Arg Cys Phe Thr Val Arg Leu Ala Arg Ala Ser Thr Arg Ala
    275                 280                 285

Glu Ala Thr Arg His Tyr Glu Arg Val Lys Ile Asp Gly Cys Phe Arg
    290                 295                 300

Arg Ser Asp Ser Ser Leu Thr Gly Gly Ala Ala Ala Asn Tyr Pro Ile
305                 310                 315                 320

Val Ser Gln Leu Ile Arg Arg Ser Arg Asn Asn Asn Met Leu Ala Ala
                325                 330                 335

Ala Ala Ala Val Ala Ala Glu Ala Ala Thr Val Pro Pro Gln His Asp
            340                 345                 350

Ala Ile Ala Gln Ala Ala Leu His Gly Ile Ser Gly Asn Asp Ile Val
    355                 360                 365

Leu Val Ala Met Ala Arg Val Leu Arg Glu Glu Arg Pro Pro Glu Glu
    370                 375                 380

Thr Glu Gly Thr Val Gly Leu Thr Ile Tyr Arg Gln Pro Glu Pro Tyr
385                 390                 395                 400

Gln Leu Glu Tyr His Thr Arg His Leu Ile Asp Gly Ser Ile Ile Asp
                405                 410                 415

Cys Asp Gln Arg Ile Gly Leu Val Ala Gly Tyr Met Lys Asp Glu Val
            420                 425                 430

Arg Asn Leu Ser Pro Phe Cys Phe Met His Leu Asp Asp Val Arg Trp
    435                 440                 445

Val Ile Val Ala Leu Arg Gln Met Tyr Asp Cys Asn Ser Asp Tyr Gly
    450                 455                 460

Glu Ser Cys Tyr Arg Leu Leu Ser Arg Asn Gly Arg Phe Ile Tyr Leu
465                 470                 475                 480

His Thr Lys Gly Phe Leu Glu Val Asp Arg Gly Ser Asn Lys Val His
                485                 490                 495

Ser Phe Leu Cys Val Asn Thr Leu Leu Asp Glu Glu Ala Gly Arg Gln
            500                 505                 510

Lys Val Gln Glu Met Lys Glu Lys Phe Ser Thr Ile Ile Lys Ala Glu
    515                 520                 525

Met Pro Thr Gln Ser Ser Ser Pro Asp Leu Pro Ala Ser Gln Ala Pro
```

-continued

```
            530                 535                 540
Gln Gln Leu Glu Arg Ile Val Leu Tyr Leu Ile Glu Asn Leu Gln Lys
545                 550                 555                 560

Ser Val Asp Ser Ala Glu Thr Val Gly Gly Gln Gly Met Glu Ser Leu
                565                 570                 575

Met Asp Asp Gly Tyr Ser Ser Pro Ala Asn Thr Leu Thr Leu Glu Glu
                580                 585                 590

Leu Ala Pro Ser Pro Thr Pro Ala Leu Ala Leu Val Pro Pro Ala Pro
                595                 600                 605

Ser Ser Val Lys Ser Ser Ile Ser Lys Ser Val Ser Val Val Asn Val
                610                 615                 620

Thr Ala Ala Arg Lys Phe Gln Gln Glu His Gln Lys Gln Arg Glu Arg
625                 630                 635                 640

Asp Arg Glu Gln Leu Lys Glu Arg Thr Asn Ser Thr Gln Gly Val Ile
                645                 650                 655

Arg Gln Leu Ser Ser Cys Leu Ser Glu Ala Glu Thr Ala Ser Cys Ile
                660                 665                 670

Leu Ser Pro Ala Ser Ser Leu Ser Ala Ser Glu Ala Pro Asp Thr Pro
                675                 680                 685

Asp Pro His Ser Asn Thr Ser Pro Pro Pro Ser Leu His Thr Arg Pro
                690                 695                 700

Ser Val Leu His Arg Thr Leu Thr Ser Thr Leu Arg
705                 710                 715

<210> SEQ ID NO 12
<211> LENGTH: 808
<212> TYPE: PRT
<213> ORGANISM: human

<400> SEQUENCE: 12

Met Asn Ser Ser Ser Ala Asn Ile Thr Tyr Ala Ser Arg Lys Arg Arg
1               5                   10                  15

Lys Pro Val Gln Lys Thr Val Lys Pro Ile Pro Ala Glu Gly Ile Lys
                20                  25                  30

Ser Asn Pro Ser Lys Arg His Arg Asp Arg Leu Asn Thr Glu Leu Asp
                35                  40                  45

Arg Leu Ala Ser Leu Leu Pro Phe Pro Gln Asp Val Ile Asn Lys Leu
        50                  55                  60

Asp Lys Leu Ser Val Leu Arg Leu Ser Val Ser Tyr Leu Arg Ala Lys
65                  70                  75                  80

Ser Phe Phe Asp Val Ala Leu Lys Ser Ser Pro Thr Glu Arg Asn Gly
                85                  90                  95

Gly Gln Asp Asn Cys Arg Ala Ala Asn Phe Arg Glu Gly Leu Asn Leu
                100                 105                 110

Gln Glu Gly Glu Phe Leu Leu Gln Ala Leu Asn Gly Phe Val Leu Val
        115                 120                 125

Val Thr Thr Asp Ala Leu Val Phe Tyr Ala Ser Ser Thr Ile Gln Asp
        130                 135                 140

Tyr Leu Gly Phe Gln Gln Ser Asp Val Ile His Gln Ser Val Tyr Glu
145                 150                 155                 160

Leu Ile His Thr Glu Asp Arg Ala Glu Phe Gln Arg Gln Leu His Trp
                165                 170                 175

Ala Leu Asn Pro Ser Gln Cys Thr Glu Ser Gly Gln Gly Ile Glu Glu
                180                 185                 190
```

-continued

```
Ala Thr Gly Leu Pro Gln Thr Val Val Cys Tyr Asn Pro Asp Gln Ile
        195                 200                 205

Pro Pro Glu Asn Ser Pro Leu Met Glu Arg Cys Phe Ile Cys Arg Leu
    210                 215                 220

Arg Cys Leu Leu Asp Asn Ser Ser Gly Phe Leu Ala Met Asn Phe Gln
225                 230                 235                 240

Gly Lys Leu Lys Tyr Leu His Gly Gln Lys Lys Gly Lys Asp Gly
                245                 250                 255

Ser Ile Leu Pro Pro Gln Leu Ala Leu Phe Ala Ile Ala Thr Pro Leu
            260                 265                 270

Gln Pro Pro Ser Ile Leu Glu Ile Arg Thr Lys Asn Phe Ile Phe Arg
        275                 280                 285

Thr Lys His Lys Leu Asp Phe Thr Pro Ile Gly Cys Asp Ala Lys Gly
    290                 295                 300

Arg Ile Val Leu Gly Tyr Thr Glu Ala Glu Leu Cys Thr Arg Gly Ser
305                 310                 315                 320

Gly Tyr Gln Phe Ile His Ala Ala Asp Met Leu Tyr Cys Ala Glu Ser
                325                 330                 335

His Ile Arg Met Ile Lys Thr Gly Glu Ser Gly Met Ile Val Phe Arg
            340                 345                 350

Leu Leu Thr Lys Asn Asn Arg Trp Thr Trp Val Gln Ser Asn Ala Arg
        355                 360                 365

Leu Leu Tyr Lys Asn Gly Arg Pro Asp Tyr Ile Ile Val Thr Gln Arg
    370                 375                 380

Pro Leu Thr Asp Glu Glu Gly Thr Glu His Leu Arg Lys Arg Asn Thr
385                 390                 395                 400

Lys Leu Pro Phe Met Phe Thr Thr Gly Glu Ala Val Leu Tyr Glu Ala
                405                 410                 415

Thr Asn Pro Phe Pro Ala Ile Met Asp Pro Leu Pro Leu Arg Thr Lys
            420                 425                 430

Asn Gly Thr Ser Gly Lys Asp Ser Ala Thr Thr Ser Thr Leu Ser Lys
        435                 440                 445

Asp Ser Leu Asn Pro Ser Ser Leu Leu Ala Ala Met Met Gln Gln Asp
    450                 455                 460

Glu Ser Ile Tyr Leu Tyr Pro Ala Ser Ser Thr Ser Ser Thr Ala Pro
465                 470                 475                 480

Phe Glu Asn Asn Phe Phe Asn Glu Ser Met Asn Glu Cys Arg Asn Trp
                485                 490                 495

Gln Asp Asn Thr Ala Pro Met Gly Asn Asp Thr Ile Leu Lys His Glu
            500                 505                 510

Gln Ile Asp Gln Pro Gln Asp Val Asn Ser Phe Ala Gly Gly His Pro
        515                 520                 525

Gly Leu Phe Gln Asp Ser Lys Asn Ser Asp Leu Tyr Ser Ile Met Lys
    530                 535                 540

Asn Leu Gly Ile Asp Phe Glu Asp Ile Arg His Met Gln Asn Glu Lys
545                 550                 555                 560

Phe Phe Arg Asn Asp Phe Ser Gly Glu Val Asp Phe Arg Asp Ile Asp
                565                 570                 575

Leu Thr Asp Glu Ile Leu Thr Tyr Val Gln Asp Ser Leu Ser Lys Ser
            580                 585                 590

Pro Phe Ile Pro Ser Asp Tyr Gln Gln Gln Ser Leu Ala Leu Asn
        595                 600                 605

Ser Ser Cys Met Val Gln Glu His Leu His Leu Glu Gln Gln Gln Gln
```

-continued

```
               610                 615                 620
His His Gln Lys Gln Val Val Glu Pro Gln Gln Leu Cys Gln
625                 630                 635                 640

Lys Met Lys His Met Gln Val Asn Gly Met Phe Glu Asn Trp Asn Ser
                645                 650                 655

Asn Gln Phe Val Pro Phe Asn Cys Pro Gln Gln Asp Pro Gln Gln Tyr
                660                 665                 670

Asn Val Phe Thr Asp Leu His Gly Ile Ser Gln Glu Phe Pro Tyr Lys
                675                 680                 685

Ser Glu Met Asp Ser Met Pro Tyr Thr Gln Asn Phe Ile Ser Cys Asn
                690                 695                 700

Gln Pro Val Leu Pro Gln His Ser Lys Cys Thr Glu Leu Asp Tyr Pro
705                 710                 715                 720

Met Gly Ser Phe Glu Pro Ser Pro Tyr Pro Thr Thr Ser Ser Leu Glu
                725                 730                 735

Asp Phe Val Thr Cys Leu Gln Leu Pro Glu Asn Gln Lys His Gly Leu
                740                 745                 750

Asn Pro Gln Ser Ala Ile Ile Thr Pro Gln Thr Cys Tyr Ala Gly Ala
                755                 760                 765

Val Ser Met Tyr Gln Cys Gln Pro Glu Pro Gln His Thr His Val Gly
                770                 775                 780

Gln Met Gln Tyr Asn Pro Val Leu Pro Gly Gln Gln Ala Phe Leu Asn
785                 790                 795                 800

Lys Phe Gln Asn Gly Val Phe Lys
                805
```

<210> SEQ ID NO 13
<211> LENGTH: 10
<212> TYPE: DNA
<213> ORGANISM: Met-JHR cDNA

<400> SEQUENCE: 13
caaaatggca                                                          10

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: motif that
      interacts with co-activators of steroin receptors
<220> FEATURE:
<223> OTHER INFORMATION: Xaas may be any amino acid

<400> SEQUENCE: 14

Leu Xaa Xaa Leu Leu
 1               5

RECOMBINANT BHLH-PAS/JHR POLYPEPTIDE AND ITS USE TO SCREEN POTENTIAL INSECTICIDES

This application is a continuation-in-part of application Ser. No. 08/843,205, filed on Apr. 14, 1997, abandoned.

BACKGROUND OF THE INVENTION

The present invention relates to a cloned "basic helix loop helix -PER-ARNT-AhR-SIM" (bHLH-PAS) protein that is a juvenile hormone receptor (JHR), bHLH-PAS/JHR. In particular, this invention is directed to a bHLH-PAS/JHR gene isolated from Drosophila, termed the methoprene-tolerant (met) gene (Met-JHR). The present invention also is directed to in vitro and in vivo methods for screening insecticides using recombinant bHLH-PAS/JHRs. The present invention is further directed to methods for isolating polynucleotides encoding bHLH-PAS/JHRs from various insect species.

Worldwide insect damage to food and fiber costs billions of dollars annually. Although chemical insecticides are still the primary means of insect control, the use of chemicals has several drawbacks including high cost of discovery, potential environmental damage, and negative public opinion. One promising group of insecticides consists of analogues of insect hormones, such as juvenile hormone. Since vertebrates do not make juvenile hormone (JH), insecticides targeted to the JH system are highly toxic to certain insects, and have shown an extraordinary degree of environmental safety.

Juvenile hormones comprise a family of hormones that are secreted by the corpus allatum, and that play a role in a variety of critical functions in insects, including development, reproduction, and morphological differentiation. Riddiford, "Hormone Action at the Cellular Level," in COMPREHENSIVE INSECT PHYSIOLOGY, BIOCHEMISTRY AND PHARMACOLOGY, VOLUME 8, Kerkut et al. (eds.), pages 37–84 (Pergamon Press 1985); Nijhout et al., *Q. Rev. Biol.* 57:109 (1982). These hormones affect development in some insects by maintaining the larval stage and inhibiting metamorphosis. In adult insects, JH is involved in the regulation of reproductive physiology. Koeppe et al., "The Role of Juvenile Hormone in Reproduction," in COMPREHENSIVE INSECT PHYSIOLOGY, BIOCHEMISTRY AND PHARMACOLOGY, VOLUME 8, Kerkut et al. (eds.), pages 165–203 (Pergamon Press 1985).

The action of JH is mediated by at least several types of JH binding proteins: a hemolymph carrier protein, a cell membrane bound receptor, and an intracellular receptor. The transport of JH to target tissues is believed to be accomplished by proteins in the hemolymph which bind with the hormone. Hammock et al., *Pestic. Biochem. Physiol.* 7:517 (1977); Goodman et al., "Juvenile Hormone Cellular and Hemolymph Binding Proteins," in COMPREHENSIVE INSECT PHYSIOLOGY, BIOCHEMISTRY AND PHARMACOLOGY, VOLUME 7, Kerkut et al. (eds.), pages 491–510 (Pergamon Press 1985). These JH binding proteins are thought to play roles both in the transport of JH and in the protection of JH from hemolymph esterases. Goodman et al., *Am. Zool.* 14:1289 1974; Kramer et al., *J. Biol. Chem.* 251:4979 (1974). Membrane bound receptors are known to bind ligand extracellularly and transmit a signal intracellularly. Wyatt et al. *Adv. Insect Physiol.* 26:1 (1996).

Cytosolic proteins that bind JH have been identified in numerous JH target tissues from a variety of insects. Van Mellaert et al., *Insect Biochem.* 15:655 (1985); Klages et al., *Nature* 286:282 (1980); Engelmann et al., *Insect Biochem.* 17:1045 (1987); Wisniewski et al., *FEBS Lett.* 171:127 (1984). One of the inventors, Thomas G. Wilson, directed a research team that identified a cytosolic juvenile hormone-binding protein in *Drosophila melanogaster* that is characterized by saturable, high-affinity binding specific for JH III. Shemshedini et al., *J. Biol. Chem.* 265:1913 (1990). Shemshedini et al. also demonstrated for the first time in any insect a correlation between the binding of JH to the cytosolic protein and a biological response to the hormone. Interference with the binding of JH to cognate intracellular receptors, therefore, would inhibit physiological functions dependent upon the hormone.

Until recently, novel insecticides that interfere with JH action were primarily discovered by an almost random testing of thousands of chemical compounds for efficacy against insects. This bioassay approach is slow and expensive since a group of test insects would have to be treated with various doses of each test compound, and, typically, finding compounds that are effective is exceedingly rare.

Accordingly, a need exists for an efficient method for testing insecticides targeted for the JH system.

SUMMARY OF THE INVENTION

Accordingly, it is an object of the present invention to provide in vitro and in vivo assays for screening potential insecticides that are JH analogs and JH antagonists.

Another object of this invention is to provide methods for cloning bHLH-PAS/JHR genes from various insect species.

These and other objects are achieved, in accordance with one embodiment of the present invention by the provision of an isolated polynucleotide that comprises an insect bHLH-PAS/JHR gene, the Met-JHR gene. A "polynucleotide" includes DNA, RNA, mRNA, and cDNA molecules. A genomic polynucleotide comprising the Met gene is the St-H fragment in FIG. 1. This fragment is 6.234 Kb, and its sequence is shown in FIG. 2 (SEQ ID NO:1). Within this 6.234 Kb segment, there is a DNA sequence of 3.011 Kb, which includes an open reading frame that is divided by one intron of 69 nucleotides (bases 1520 to 1588). This 3.011 Kb sequence is the genomic Met-JHR DNA sequence. FIG. 3 (SEQ ID NO:2).

The Met-JHR open reading frame lacking the intron codes for a protein of 716 amino acids and a having a molecular weight of about 78,720 daltons.

The nucleotide sequences of the genomic and cDNA Met-JHR differ, reflecting polymorphism. In FIG. 3, SEQ ID NO:3 represents a Met-JHR cDNA sequence, which begins at nucleotide 4 of the genomic sequence. There is one "polymorphic" difference between the genomic and cDNA nucleotide sequences that results in a change at the amino acid level. The nucleotide at position 1043 (genomic)/1039 (cDNA) may be C or T, which results in different deduced amino acids, R and W, respectively.

In the sequence of the genomic DNA, there is one ambiguity that results in different deduced amino acids. Base number 875 in the genomic DNA is designated "R," which signifies that the nucleotide may be the purine C or G. This results in two possible corresponding deduced amino acid sequences, G (Gly) or R (Arg) respectively. In the sequence of the cDNA, there is one ambiguity that results in a different deduced amino acids. Base number 526 in the genomic DNA is designated "M," which signifies that the nucleotide may be the purine A or C. This results in two possible corresponding deduced amino acid sequences, T (Thr) or P (Pro) respectively.

As used herein, the term "juvenile hormone receptor" (JHR) is used to mean a polypeptide that is involved in binding JHIII. As used herein, a polypeptide that is "involved in binding" JHIII includes a polypeptide that directly binds JHIII, a polypeptide that is a partner to a polypeptide that directly binds JHIII, and a polypeptide that is a partner to a complex of polypeptides that bind JHIII. One or more of these polypeptides may be required for binding JHIII. The skilled artisan will recognize that heterodimeric receptors are known in the art, and that both polypeptide that form the heterodimer are required for hormone binding and activity in the target cell. For example, the ultraspiracle polypeptide is partner to the ecdysone receptor, which together bind the hormone ecdysone and mediate ecdysone activation of gene transcription. Yao, et al. *Cell* 71:63 (1992).

A multicomponent complex between bHLH-PAS polypeptide and steroid receptors has been documented. For example, a bHLH-PAS polypeptide that functions a co-activator during ligand induction of estrogen steroid receptor is amplified in breast cancer-1 (AIBC or ACTR). Anzick et al. *Science*, 277:956 (1997); Chen et al. *Cell* 90:569 (1997). The JHR may involve a number of polypeptides that together form a ligand binding unit or functional signal transducing complex.

Thus, a suitable insect JHR gene encodes a polypeptide that directly binds to JHIII. Another suitable insect JHR gene encodes a polypeptide that is a heteromultimeric partner to a polypeptide that directly binds JHIII. A further suitable insect JHR gene encodes a polypeptide that forms a homomultimeric complex that binds JHIII. A suitable JHR is a bHLH-PAS/JHR polypeptide, i.e., a bHLH-PAS polypeptide that is involved in binding juvenile hormone III. Such a bHLH-PAS/JHR polypeptide includes, but is not limited to, the Met-JHR polypeptide and the Met-JHR-erecta polypeptide.

As used herein, a "bHLH-PAS protein" is a member of a family of transcriptional activators known as the basic helix-loop-helix-Per-Arnt-Sim (bhlh-PAS) proteins. These proteins share homology in two domains. The first domain is located at the N-terminus of the protein and comprises a region of basic amino acids followed by a region of approximately 50 conserved amino acids that form two amphipathic $\alpha$ helices that are joined by a variable loop: the basic domain and the helix loop helix are collectively referred to as bHLH.

The second domain is located immediately C-terminal to the bHLH domain and consists of approximately 300 amino acids termed PAS homology domain (for their original observation in the Drosophila midline development protein single-minded (sim) and the *Drosophila circadian* oscillator Period (per)). The PAS domain contains two copies of an approximately 50-amino acid degenerate repeat, referred to as the PAS A and PAS B repeats.

Additionally, some members of the bHLH-PAS family have at their C-termini a transcriptional activator domain, also called transactivation domain (TAD), which has been divided into three distinct classes corresponding to amino acid composition: rich in glutamines (Q-rich); rich in acidic amino acids (i.e., aspartate and glutamate); or with a high concentration of prolines, serines, and/or threonines (P/S/T).

The basic region of a bHLH-PAS protein is associated with DNA binding, and the HLH and PAS domains are associated with DNA binding and dimerization functions. The founding member of this family is the aryl hydrocarbon nuclear receptor translation (ARNT), so named because it was considered to translocate the ligand-bound aryl hydrocarbon receptor (AhR) to the nucleus. AhR is the only member in the bHLH-PAS family known to bind a ligand.

The ARNT receptor which is not bound to ligand is associated with two proteins, the 90 kDa heat shock protein and an unidentified 43 kDA protein, and ligand binding is concomitant with dissociation of these proteins. Association with these proteins and binding of the ligands has been mapped to the same region, the middle third portion of the AhR protein, which includes the PAS B domain approximately in the middle.

The formation of a heterodimeric complex between the ligand-bound AhR and ARNT permits the complex to bind its enhancers, i.e., the dioxin or xenobiotic response elements (DRE or XRE, respectively) and induces transcription of specific genes.

Another family member, the hypoxia-inducible factor 1 alpha receptor (HIF-1$\alpha$), which appears to sense low oxygen levels in the cell (hypoxia), also forms heterodimeric complexes with ARNT. In the presence of low oxygen, the HIF-1$\alpha$/ARNT heterodimeric complex binds HIF-1$\alpha$ response elements (enhancers), and thereby induces gene transcription. sim also appears to heterodimerize with ARNT. The AhR/ARNT heterodimeric complex has been used as a model system to study the mechanism by which these family members transduce intracellular signals. Rowlands et al. *Critical Reviews in Toxicology*, 27: 109 (1997).

A suitable insect bHLH-PAS/JHR polynucleotide has a nucleotide sequence that encodes an amino acid sequence of SEQ ID NO:4 or SEQ ID NO:5. Other suitable bHLH-PAS/JHR polynucleotides comprise the nucleotide sequence of SEQ ID NO:2, SEQ ID NO:3, SEQ ID NO:6 and SEQ ID NO:7. The present invention also contemplates host cells comprising such polynucleotides, and methods of using such host cells to produce bHLH-PAS/JHR.

Thus, the present invention provides an isolated polynucleotide that encodes a bHLH-PAS polypeptide that is involved in binding JHIII, also designated bHLH-PAS/JHR. The invention also includes a polynucleotide that encodes a bHLH-PAS/JHR polypeptide that directly binds juvenile hormone III, and a bHLH4-PAS/JHR polypeptide that directly binds juvenile hormone III as a monomer. The invention also includes a polynucleotide that encodes a bHLH-PAS/JHR polypeptide that directly binds juvenile hormone III as a homomultimer. The invention further includes an isolated polynucleotide encoding a bHLH-PAS/JHR polypeptide, wherein said polynucleotide encodes a polypeptide that is a heteromultimeric partner of a polypeptide that directly binds juvenile hormone III.

The invention includes an isolated polynucleotide encoding an insect bHLH-PAS/JHR polypeptide, wherein the insect is selected from the group consisting of Coleoptera, Siphonoptera, Orthoptera, Thysanoptera, Lepidoptera, Hemiptera, and Diptera. Members of Diptera may be selected from the group consisting of horn fly, fruit fly, screwworm fly, blow fly, mosquito, mediterranean fruit fly, biting midge, black fly, horse fly, deer fly, stable fly, leaf miner, housefly, bot fly, warble fly, tiger mosquito, swamp marsh mosquito, *Culex pipieus, Aedes aegypti*, and *Anopheles albopictus*.

The invention includes an isolated polynucleotide that encodes a polypeptide having an amino acid sequence selected from the group consisting of SEQ ID NO:4 (FIG. 4) and SEQ ID NO:5 (FIG. 4). The invention further includes an isolated polynucleotide that comprises a nucleotide sequence selected from the group consisting of SEQ ID NO:2 and SEQ ID NO:3 (FIG. 3). The invention also includes an isolated polynucleotide that comprises the nucleotide sequence selected from the group consisting of SEQ ID NO:6 and SEQ ID NO:7 (FIG. 5).

The invention also includes an isolated polynucleotide which comprises the sequence of SEQ ID NO:1, an isolated polynucleotide which comprises the sequence of nucleotide 1 through nucleotide 1291 of SEQ ID NO:1, an isolated polynucleotide which comprises the sequence of nucleotide 1 through nucleotide 1513 of SEQ ID NO:1, an isolated polynucleotide which comprises the sequence of nucleotide 3733 through nucleotide 6235 of SEQ ID NO:1, and an isolated polynucleotide which comprises the sequence of nucleotide 4302 through nucleotide 6235 of SEQ ID NO:1.

The invention also includes an isolated polynucleotide comprising the nucleotide sequence of the St-H fragment in vector pSt-H, which was deposited at the American Type Culture Collection, in Bethesda, Md., on Nov. 13, 1997.

The invention further comprises an isolated polynucleotide comprising the nucleotide sequence of SEQ ID NO:7 (FIG. 5).

The invention includes an isolated polynucleotide that encodes a bHLH-PAS/JHR polypeptide that is involved in binding JHIII, and that hybridizes under stringent conditions with a polynucleotide having a nucleotide sequence selected from the group consisting of SEQ ID NO:1, SEQ ID NO:2, SEQ ID NO:3, and SEQ ID NO:6. The invention also includes an isolated polynucleotide that encodes a bHLH-PAS/JHR polypeptide that is involved in binding JHIII, and that hybridizes under stringent conditions with a polynucleotide having a nucleotide sequence of SEQ ID NO:7. The invention also includes an isolated polynucleotide that encodes a bHLH-PAS/JHR polypeptide that is involved in binding JHIII, and that hybridizes under stringent conditions with a polynucleotide that encodes a protein having the amino acid sequence selected from the group consisting of SEQ ID NO:4 and SEQ ID NO:5.

The invention also includes an isolated polynucleotide that encodes a bHLH-PAS/JHR polypeptide that is involved in binding JHIII and that hybridizes under stringent conditions with a riboprobe that is the reverse transcript of a polynucleotide having the sequence of nucleotide 1514 through 1845 of SEQ ID NO:1 (nucleotides 771 to 1102 of the Met-JHR open reading frame) The invention further includes an isolated polynucleotide that encodes a bHLH-PAS/JHR polypeptide that is involved in binding JHIII, and that hybridizes with a riboprobe that is the reverse transcript of a polynucleotide having the sequence of nucleotide 1514 through 1845 of SEQ ID NO:1 (nucleotides 771 to 1102 of the Met-JHR open reading frame), wherein said hybridization is carried out in 5×SSPE, 5×Denhardt's, 0.5% SDS, 50% formamide, and 100 μg/ml yeast tRNA for about 15 to about 17 hours at 68° C.

The invention includes an expression vector comprising an isolated polynucleotide encoding an insect bHLH-PAS/JHR polypeptide, and A cultured host cell comprising such an expression vector. The host cell is selected from the group consisting of bacterial cell, yeast cell, insect cell and mammalian cell.

The invention also includes a method of producing a polypeptide, said method comprising the steps of:
 (a) culturing a host cell comprising an expression vector that comprises a bHLH-PAS/JHR gene, wherein said cultured host cell expresses said bHLH-PAS/JHR gene, and
 (b) isolating said polypeptide from said cultured host cell.

The invention also includes an isolated polypeptide selected from the group consisting of:

(a) a conservative amino acid variant of SEQ ID NO:4,
 (b) a functional fragment of a polypeptide having the amino acid sequence of SEQ ID NO:4,
 (c) a polypeptide having an amino acid sequence of SEQ ID NO:4,
 (d) a conservative amino acid variant of SEQ ID NO:5,
 (e) a functional fragment of a polypeptide having the amino acid sequence of SEQ ID NO:5,
 (f) a polypeptide having an amino acid sequence of SEQ ID NO:5, and
 (g) a Met-JHR alternatively-spliced isoform.

The invention also includes the above-mentioned isolated polypeptides, wherein the conservative amino acid variant is a polypeptide having an amino acid sequence that differs from the amino acid sequence of SEQ ID NO:4 by containing at least one amino acid substitution selected from the group consisting of (1) the substitution of an alkyl amino acid for an alkyl amino acid in SEQ ID NO:4, (2) the substitution of an aromatic amino acid for an aromatic amino acid in SEQ ID NO:4, (3) the substitution of a sulfur-containing amino acid for a sulfur-containing amino acid in SEQ ID NO:4, (4) the substitution of a hydroxy-containing amino acid for a hydroxy-containing amino acid in SEQ ID NO:4, (5) the substitution of an acidic amino acid for an acidic amino acid in SEQ ID NO:4, (6) the substitution of a basic amino acid for a basic amino acid in SEQ ID NO:4, and (7) the substitution of a dibasic monocarboxylic amino acid for a dibasic monocarboxylic amino acid in SEQ ID NO:4.

The invention further includes the above-described isolated polypeptides, wherein the conservative amino acid variant is a polypeptide having an amino acid sequence that differs from the amino acid sequence of SEQ ID NO:5 by containing at least one amino acid substitution selected from the group consisting of (1) the substitution of an alkyl amino acid for an alkyl amino acid in SEQ ID NO:5, (2) the substitution of an aromatic amino acid for an aromatic amino acid in SEQ ID NO:5, (3) the substitution of a sulfur-containing amino acid for a sulfur-containing amino acid in SEQ ID NO:5, (4) the substitution of a hydroxy-containing amino acid for a hydroxy-containing amino acid in SEQ ID NO:5, (5) the substitution of an acidic amino acid for an acidic amino acid in SEQ ID NO:5, (6) the substitution of a basic amino acid for a basic amino acid in SEQ ID NO:5, and (7) the substitution of a dibasic monocarboxylic amino acid for a dibasic monocarboxylic amino acid in SEQ ID NO:5.

The invention further includes a method for screening compounds that specifically bind with a bHLH-PAS/JHR polypeptide, comprising:
 (a) incubating a test compound in a solution that comprises an isolated recombinant bHLH-PAS/JHR polypeptide, and
 (b) detecting the binding of said test compound with said polypeptide.

The invention includes a method for screening compounds that specifically bind with a complex comprising a bHLH-PAS/JHR polypeptide and a heteromultimeric partner of said polypeptide, comprising:
 (a) incubating a test compound in a solution that comprises an isolated bHLH-PAS/JHR polypeptide, and an isolated heteromultimeric partner of said polypeptide, and
 (b) detecting the binding of said test compound with said complex.

In such methods, the test compound may be detectably labeled. In addition, the binding of said test compound with said polypeptide may be detected in step (b) using a scintillation proximity assay. Furthermore, in such a method, the detectably labeled test compound may comprise a detectable label selected from the group consisting of radiolabel, fluorescent label, chemiluminescent label, and bioluminescent label.

Such binding methods also may further comprise the step of incubating the bHLH-PAS/JHR polypeptide with a detectably labeled ligand, wherein said detectably labeled ligand is added to said solution containing said receptor at a time selected from the group consisting of (i) prior to step (a), (ii) after step (a) and before step (b), and (iii) concomitantly with the addition of said test compound.

The detectably labeled ligand is these binding methods may be juvenile hormone or a juvenile hormone analog, and the detectable label may be selected from the group consisting of radiolabel, fluorescent label, chemiluminescent label, and bioluminescent label. Additionally, these methods may be carried out with [$^3$H]10R-juvenile hormone III or [$^3$H]methoprene.

These binding methods may also further comprise the step of incubating said bHLH-PAS/JHR polypeptide with a detectably labeled photoaffinity analog of juvenile hormone after step (a) and before step (b).

The binding methods of the invention may be carried out with a bHLH-PAS/JHR polypeptide selected from the group consisting of:

(a) a conservative amino acid variant of SEQ ID NO:4, (b) a functional fragment of a polypeptide having Ithe amino acid sequence of SEQ ID NO:4, (c) a polypeptide having an amino acid sequence of SEQ ID NO:4, (d) a conservative amino acid variant of SEQ ID NO:5, (e) a functional fragment of a polypeptide having the amino acid sequence of SEQ ID NO:5, (f) a polypeptide having an amino acid sequence of SEQ ID NO:5, and (g) a Met-JHR alternatively-spliced isoform.

The invention further comprises a nucleic acid probe for detecting RFLPs in an insect population, wherein said RFLPs discriminate between JH-sensitive and JH-resistant individuals, said probe comprising a genetic locus in a gene encoding a bHLH-PAS/JHR polypeptide that is associated with JH analog sensitivity and resistance traits.

The invention also encompasses a method for detecting JH-resistant individuals in an insect population, said method comprising:

(a) obtaining a representative biological sample of said population; and (b) detecting a nucleic acid sequence in said sample that corresponds to a predetermined sequence within a gene encoding a bHLH-PAS/JHR polypeptide that is altered in JH analog-resistant individuals.

The detection step (b) may method comprise:

(i) amplifying a nucleic acid sequence from said sample, wherein said sequence corresponds to a predetermined sequence within a gene sequence encoding a bHLH-PAS/JHR polypeptide and wherein said sequence comprises at least one RFLP characteristic of JH analog resistance;

(ii) incubating said amplified nucleic acid with at least one predetermined restriction endonuclease, to form fragments;

(iii) size-separating said fragments to form a detectable pattern; and (iv) comparing said pattern with a predetermined pattern obtained from JH analog-resistant individuals to detect the appearance of one or more RFLP characteristic of JH analog resistance.

The invention provides an in vivo method for screening compounds that specifically bind with a bHLH-PAS/JHR, comprising:

(a) providing a host cell comprising (1) DNA encoding a fusion polypeptide comprising a bHLH-PAS/JHR polypeptide and a second polypeptide comprising a DNA binding domain, and (2) a reporter gene under the control of a minimal promoter driven by the response element for said second polypeptide;

(b) incubating a test compound with said host cell; and (c) detecting the binding of the test compound to said bHLH-PAS/JHR by monitoring expression of the reporter gene.

The invention further provides an in vivo method for screening compounds that specifically bind with a bHLH-PAS/JHR, comprising the steps of:

(a) providing a host cell comprising (1) DNA encoding a fusion polypeptide comprising a bHLH-PAS/JHR polypeptide and a second polypeptide comprising a DNA binding domain; (2) a reporter gene under the control of a minimal promoter driven by the response element for said second polypeptide; and (3) DNA encoding a polypeptide that is a heterodimeric partner of said bHLH-PAS/JHR;

(b) incubating a test compound with said host cell; and (c) detecting the binding of the test compound to said bHLH-PAS/JHR by monitoring expression of the reporter gene.

The invention also provides an in vivo method for screening compounds that specifically bind to a multimeric complex comprising a bHLH-PAS/JHR polypeptide and the heteromultimeric partner of said polypeptide, comprising the steps of:

(a) providing a host cell comprising (1) DNA encoding a fusion polypeptide comprising bHLH-PAS/JHR polypeptide and the DNA binding domain of a second polypeptide, (2) DNA encoding a heteromultimeric partner of said bHLH-PAS/JHR polypeptide and the activation domain of said second polypeptide, and (3) a reporter gene under the control of a minimal promoter driven by the response element for said second polypeptide;

(b) incubating a test compound with said host cell; and (c) detecting the binding of the test compound to said complex by monitoring expression of the reporter gene.

The invention additionally provides an in vivo method for screening compounds that specifically bind to a multimeric complex comprising a bHLH-PAS/JHR polypeptide and the heteromultimeric partner of said polypeptide, comprising the steps of:

(a) providing a host cell comprising (1) DNA encoding a fusion polypeptide comprising bHLH-PAS/JHR polypeptide and the activation domain of a second polypeptide, (2) DNA encoding a heteromultimeric partner of said bHLH-PAS/JHR polypeptide and the DNA binding domain of said second polypeptide, and (3) a reporter gene under the control of a minimal promoter driven by the response element for said second polypeptide;

(b) incubating a test compound with said host cell; and (c) detecting the binding of the test compound to said complex by monitoring expression of the reporter gene.

The invention provides an in vivo method for screening compounds that specifically bind with a bHLH-PAS/JHR polypeptide, comprising:

(a) providing a host cell comprising (1) DNA encoding a fusion polypeptide comprising a bHLH-PAS/JHR polypeptide and the DNA binding region of a second polypeptide, (2) DNA encoding a bHLH-PAS/JHR polypeptide and the activation domain of said second polypeptide, and (3) a reporter gene under the control of a minimal promoter driven by the response element for said second polypeptide;

(b) incubating a test compound with said host cell; and (c) detecting the binding of the test compound with said bHLH-PAS/JHR polypeptide by monitoring expression of the reporter gene.

Any of the in vivo methods provided for by the invention may be employed using a host cell selected from the group of an insect cell, a yeast cell, and a mammalian cell.

BRIEF DESCRIPTION OF THE DRAWINGS

FIG. 2 (SEQ ID NO:1) shows the nucleotide sequence of the 6.234 Kb St-H segment shown in FIG. 1. Base number 1514, A, is underlined and designates the first base of the Met-JHR open reading frame. Base number 3732, G, is underlined and designates the last base of the Met-JHR open reading frame. Base number 1292, C, is underlined and is the first base in the genomic DNA sequence in FIG. 3. Base number 4301, T, is underlined and designates the last base in the genomic DNA sequence in FIG. 3. The intron is shown in lower case letters.

FIGS. 3A and 3B provide the nucleotide sequences for the Met-JHR genomic DNA ("MetGen"; SEQ ID NO:2) and cDNA (SEQ ID NO:3). Boxed residues are those in the cDNA that differ from the genomic DNA. Nucleotide 875 in the genomic DNA is designated as "R," indicating that a G or a C may be present in this position. If it is G, the corresponding amino acid is Gly (G) and if it is C, the corresponding amino acid is Arg (R). Nucleotide 526 in the cDNA is designated as "M," indicating that an A or a C may be present in this position. If the nucleotide is A, the corresponding amino acid is Thr (T), and if it is C, the corresponding amino acid is Pro (P).

FIG. 4 provides the amino acid sequences deduced from the Met-JHR genomic DNA (SEQ ID NO:4) and cDNA (SEQ ID NO:5). "X" at amino acid 103 deduced from cDNA means that this residue may be Gly or Arg. "X" at amino acid 218 deduced from the genomic DNA means that Thr or Pro.

FIG. 5 shows a comparison of a portion of the Met-JHR gene from D.melanogaster (sequence A) (SEQ ID NO:6) and a nucleotide sequence from the Met gene from D.erecta (sequence B) (SEQ ID NO:7). Dash symbols (-) indicate spaces in the printed sequence that were added to show alignment of the A and B sequences.

FIG. 6 provides a comparison of the amino acid sequence of the Met-JHR cDNA, Drosophila aromatic hydrocarbon receptor nuclear translocator protein (DARNT), human ARNT (HARNT) [Zelzer et al. Genes & Dev. 11:2079 (1997)], brain and muscle ARNT-like protein a (BmAll) [Ikeda et al. Biochem. Biophys. Res. Comm. 233:258 (1997)] and human aromatic hydrocarbon receptor (AhR-human). (SEQ ID NOS: 8–12). The motifs of bHLH-PAS proteins [Rowlands et al. Crit. Rev. Toxicol. 27:109 (1997)] that are functionally characterized for ARNT are included at the top of the alignments. The residues of Met-JHR are boxed, and the residues in the other four proteins that match Met-JHR also are boxed. When an amino acid residue from all five proteins match, they form a consensus sequence which is included at the top of the alignments. The skilled artisan will recognize that additional matches can be generated by moving amino acids one or two positions. The position of the "LXXLL" motif in the Met-JHR gene is also shown, above the appropriate sequence, LMQLL (amino acids 129–133).

DETAILED DESCRIPTION

1. Overview

Figure 1:
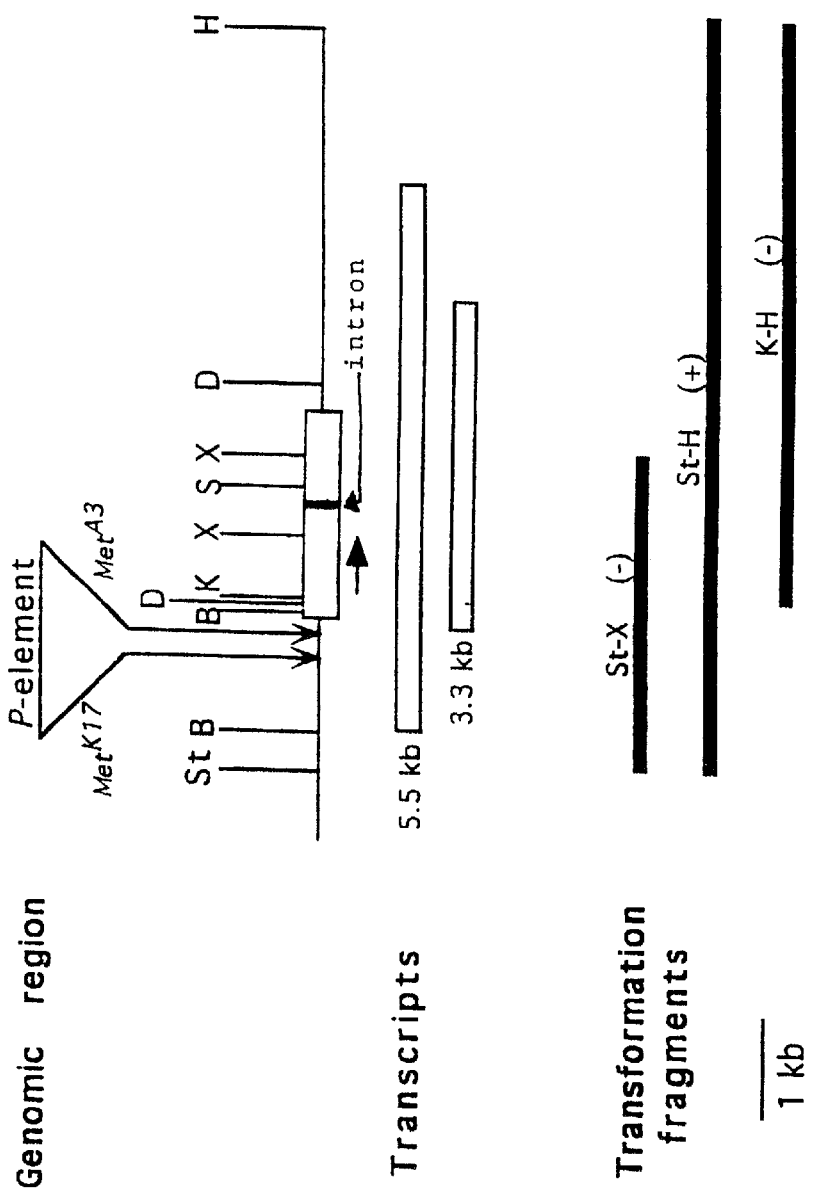
FIG. 1 illustrates the genomic region surrounding the P-element insertion sites in two mutant alleles, Met$^{A3}$ and Met$^{K17}$, the sequence which encodes bHLH-PAS/JHR, and the transcripts observed for this region. The figure also shows DNA fragments used in transformation studies to rescue the Met phenotype, demonstrating that fragment St-H carries a functional copy of the Met gene. P-element insertional sites in the Met$^{A3}$ and Met$^{K17}$ alleles are shown at the arrows. The locations of the transcripts as deduced from cDNA sequencing and RT-PCR analysis are noted below the map. The genomic transformation fragments are indicated. Those that did not rescue the resistance phenotype are noted (−) and the fragment that produced methoprene susceptibility in transformant flies is noted (+). D=Hind III; S=Sal I; K=Kpn I; St=Stu I; B=Dam HI; X=Xho I; H=Hpa I.

Attempts have been made to rationally design a potent JH analog, but the structure-activity relationship was found to be extremely complex, and varied from species to species. Retnakaran et al., "Insect Growth Regulators," in *COMPREHENSIVE INSECT PHYSIOLOGY AND PHARMACOLOGY*, Volume 12, Kerkut et al. (eds.) pages 530–601 (Pergamon Press 1985). In retrospect, the chemical structures of many JH analogs were found to be totally unrelated to the structures of endogenous juvenile hormone. See, for example, Sláma, "Pharmacology of Insect Juvenile Hormones," in *COMPREHENSIVE INSECT PHYSIOLOGY AND PHARMACOLOGY*, Volume 11, Kerkut et al. (eds.) pages 357–394 (Pergamon Press 1985). Accordingly, novel insecticides that interfere with JH action were primarily discovered by an almost random testing of thousands of chemical compounds for efficacy against insects in bioassays.

JH analogs will maintain insects in an immature state. Thus, JH analog insecticides will be most useful in combatting insects that do not have a destructive immature stage (e.g. a larval stage), that will damage crops. On the other hand, some insects have highly destructive larval stages, such as caterpillars. Thus, it is not desirable to maintain such insects in the immature state. JH antagonists will be useful as insecticides. A JH antagonist will be lethal during the larval phase, "tricking" into entering pupation which the larva is not equipped to handle.

As described herein, a novel bHLH-PAS protein has been isolated from Drosophila, and is called Met-JHR. It is expected that the Met-JHR gene encodes a JH receptor. Various features of the Met-JHR gene are consistent with all the features predicted by biochemical analysis of the JHR protein [Shemshedini et al. *J. Biol. Chem.* 265(4):1913 (1990)] and the Met-JHR gene product. The longest single open reading frame in the genomic Met-JHR sequence encodes a protein of 78,720 daltons and has the structure of a bHLH-PAS nuclear transcriptional protein.

The Met-JHR gene is used to express polypeptide useful for in vitro and in vivo screening of insecticides. The gene also is useful for isolating related bHLH-PAS/JHR genes from a variety of insects, which in turn, can be used for species-specific screening assays. Having such genes permits a more detailed analysis of the mechanisms of ligand binding, and hence rational design of insecticides. Such genes also will permit monitoring insects for JHIII and JHIII analog resistance.

2. Definitions

In the description that follows, a number of terms are utilized extensively. Definitions are herein provided to facilitate understanding of the invention.

Structural gene. A DNA sequence that is transcribed into messenger RNA (mRNA) which is then translated into a sequence of amino acids characteristic of a specific polypeptide (protein).

Promoter. A DNA sequence which directs the transcription of a structural gene to produce mRNA. Typically, a promoter is located in the 5' region of a gene, proximal to the start codon of a structural gene. If a promoter is an inducible promoter, then the rate of transcription increases in response to an inducing agent. In contrast, the rate of transcription is not regulated by an inducing agent if the promoter is a constitutive promoter.

Enhancer. A genetic element related to transcription. An enhancer can increase the efficiency with which a particular gene is transcribed into mRNA irrespective of the distance or orientation of the enhancer relative to the start site of transcription. The enhancer effect is mediated through sequence-specific DNA binding proteins. An enhancer is also referred to as a "response element."

Complementary DNA (cDNA). Complementary DNA is a single-stranded DNA molecule that can be formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule derived from a single mRNA molecule.

Genomic DNA. Chromosomal DNA, including introns. An intron is an intervening sequence. It is a non-coding sequence of DNA within a gene that is transcribed into hnRNA but is then removed by RNA splicing in the nucleus, leaving a mature mRNA which is then translated in the cytoplasm. The regions at the ends of an intron are self-complementary, allowing a hairpin structure to form naturally in the hnRNA.

Expression. Expression is the process by which a polypeptide is produced from a structural gene. The process involves transcription of the gene into mRNA and the translation of such mRNA into polypeptide(s).

Cloning vector. A DNA molecule, such as a plasmid, cosmid, phagemid, or bacteriophage or other virally-derived entity, which has the capability of replicating autonomously in a host cell and which is used to transform cells for gene manipulation. Cloning vectors typically contain one or a small number of restriction endonuclease recognition sites at which foreign DNA sequences may be inserted in a determinable fashion without loss of an essential biological function of the vector, as well as a marker gene which is suitable for use in the identification and selection of cells transformed with the cloning vector. Marker genes typically include genes that provide tetracycline resistance or ampicillin resistance.

Drosophila mutants. The mutant gene that is responsible for methoprene resistance is termed Methoprene-tolerant, symbolized as Met. Various mutant alleles are given superscripts; for example, $Met^{A3}$. Met implies $Met^1$, the original mutant allele recovered, when speaking of the mutant fly. The wild-type or normal gene is termed $Met^+$ and describes the genotype in flies that have a normally functioning bHLH-PAS/JHR protein.

Expression vector. A DNA molecule comprising a cloned structural gene encoding a foreign protein which provides the expression of the foreign protein in a recombinant host. Typically, the expression of the cloned gene is placed under the control of (i.e., operably linked to) certain regulatory sequences such as promoter and enhancer sequences. Promoter sequences may be either constitutive or inducible.

Recombinant Host. A recombinant host may be any prokaryotic or eukaryotic cell which contains either a cloning vector or expression vector. This term is also meant to include those prokaryotic or eukaryotic cells that have been genetically engineered to contain the cloned gene(s) in the chromosome or genome of the host cell. For examples of suitable hosts, see Sambrook et al., *MOLECULAR CLONING: A LABORATORY MANUAL*, Second Edition, Cold Spring Harbor Laboratory, Cold Spring Harbor, N.Y. (1989) ["Sambrook"].

As used herein, a "substantially pure protein" means that the desired purified protein is essentially free from contaminating cellular components, as evidenced by a single band following polyacrylamide-sodium dodecyl sulfate gel electrophoresis (SDS-PAGE).

The term "substantially pure" is further meant to describe a molecule which is homogeneous by one or more purity or homogeneity characteristics used by those of skill in the art. For example, a substantially pure bHLH-PAS/JHR will show constant and reproducible characteristics within standard experimental deviations for parameters such as the following: molecular weight, chromatographic migration, amino acid composition, amino acid sequence, blocked or unblocked N-terminus, HPLC elution profile, biological activity, and other such parameters. The term, however, is not meant to exclude artificial or synthetic mixtures of the molecule with other compounds. In addition, the term is not meant to exclude bHLH-PAS/JHR fusion proteins isolated from a recombinant host.

Juvenile Hormone. The members of the JH family are: JH I ([2R-[2α(2E,6E),3α]]-7-ethyl-9-(3-ethyl-3- methyloxiranyl)-3-methyl-2,6-nonadienoic acid methyl ester; methyl (2E,6E,10R,11S)-10,11-epoxy-7-ethyl-3,11-dimethyl-2,6-tridecadienoate; C-18 JH), JH II ([2R-[2α(2E,6E),3α]]-9-(3-ethyl-3-methyloxiranyl)-3,7-dimethyl-2,6-nonadienoic acid methyl ester; methyl (2E,6E,10R,11S)-10,11-epoxy-3,7,11-trimethyl-2,6-tridecadienoate; C-17 JH), and JH III ([R-(E,E)]-9-(3,3-dimethyloxiranyl)-3,7-dimethyl-2,6-nonadienoic acid methyl ester; methyl (2E,6E,10R)-10,11-epoxy-3,7,11-trimethyl-2,6-dodecadienoate; C-16 JH).

Juvenile Hormone Analog. A JH analog is a compound that is an agonist—it mimics LJH and usually has insecticidal properties resulting from this activity. Examples of JH analogs include: methoprene ([E,E]-11-methoxy-3,7,11-trimethyl-2,4-dodecadienoic acid 1-methylethyl ester) and pyriproxyfen (2-[1-methyl-2-(4-phenoxyphenoxy) ethoxylpyridine).

Juvenile Hormone Antagonist. A compound that will block the activity of JH and that can have insecticidal properties resulting from this activity. An antagonist prevents JH agonists from eliciting their effects.

3. Isolation of DNA Sequences that Encode the Met Juvenile Hormone Receptor

To study the role of juvenile hormone, a genetic approach was used to identify an insensitive JH mutant. These studies took advantage of the high toxicity of methoprene, a JH analog insecticide to Drosophila. Wilson and Fabian, *Dev. Biol.* 118:190 (1986); Riddiford and Ashburner, *Gen. Comp. Endocrinol.* 82:172 (1991). Reasoning that the phenotype "resistance to methoprene" would produce a mutant that also would be resistant to JH, and that the primary lesion potentially could be in a JHR, progeny of Drosophila males that had been mutagenized by ethyl methanesulfonate (a chemical mutagen) or X-rays were screened on a dose of methoprene that is toxic to susceptible flies. Wilson and Fabian, "Selection of methoprene-resistant mutants of *Drosophila melanogaster*," in Law (ed.), *MOLECULAR ENDOCRINOLOGY. UCLA SYMPOSIA ON MOLECULAR AND CELLULAR BIOLOGY, NEW SERIES*, Volume 49, pages 179–188 (1987). A total of eight dominant Drosophila lines with high resistance to methoprene were recovered, all of which proved to be alleles at a locus designated as Methoprene-tolerant (Met). Wilson and Fabian, (1986, 1987).

The mutant Met phenotype has been genetically characterized as follows: (1) Met results in as much as 100-fold resistance to both the toxic and morphogenetic effects of methoprene; (2) Met maps by recombination to 35.4 on the X-chromosome and by deficiency mapping to polytene chromosome bands 10C5-D2; (3) loss of wild-type Met gene function is expressed as a semidominant mutation; resistance is present in heterozygotes at a level intermediate between that in homozygotes and in wild-type; and (4) the Met gene mutation results in resistance to topical application of both the natural hormones, JH III and JH bisepoxide, as well as to two additional JH analogs, fenoxycarb and pyriproxyfen. Mutant Met flies are not resistant to other classes of insecticides that have different modes of action. The Met phenotype was also found to be expressed autonomously in genetic mosaics. This observation ruled out a circulating factor as the basis of Met resistance. Wilson and Fabian (1986).

The biochemistry of Met resistance has been studied extensively. Biochemical analysis of Met resistance has eliminated four, and identified one, possible mechanisms for resistance. Enhanced secretion or metabolism, tissue sequestration, and reduced cuticular penetration of JH were ruled out by direct experimentation. Shemshedini and Wilson, *Proc. Nat'l Acad. Sci. USA* 87:2072 (1990). However, when binding of JH to a target tissue was examined, Met flies were found to possess a JH cytosolic binding protein that has an apparent 10-fold lower binding affinity for JH III than that from $Met^+$ flies. Similar results with lowered affinity JH binding proteins were obtained upon examination of two additional Met alleles. Shemshedini and Wilson, *Proc. Nat'l Acad. Sci. USA* 87:2072 (1990).

An initial experiment was designed to clone the Met gene by transposon tagging with P-element transposable genetic elements. Bingham et al., *Cell* 25:693 (1981). This method required a P-element insertion either in or near the $Met^+$ (wild type) gene. A screen was devised to recover P-element insertional Met alleles following P-element-mediated mutagenesis, and four alleles were recovered. Two of these, designated $Met^{A3}$ and $Met^{K17}$, were shown to be P-element insertions by both genetic reversion experiments and in situ hybridization of a P-element DNA probe to the expected cytogenetic region of Met at 1OC expected for the $Met^+$ gene. Wilson et al., "Molecular analysis of Methoprene-tolerant, a gene in Drosophila involved in resistance to JH analog insect growth regulators," in *MOLECULAR MECHANISMS OF INSECTICIDE RESISTANCE: DIVERSITY AMONG INSECTS. AMERICANL SOCIETY SYMPOSIUM SERIES*, Volume 505, Mullin et al. (eds), pages 99–112 (1992); Wilson, *J. Econ. Entomol.* 86:645 (1993). Each of the $Met^{A3}$ and $Met^{K17}$ alleles conferred resistance to both the toxic and morphogenetic effects JH and methoprene, and susceptible revertants could be recovered by genetic means. Wilson, et al. *Mol. Mech. of Insecticide Resistance* (Am. Chem. Soc. Symp.) 505:99 (1993); Wilson, T. G. *J. Econ. Entomol.* 86:645 (1993).

In a follow-up study, genomic libraries were constructed from these alleles to isolate a large region that likely contains the Met gene. Turner and Wilson, *Arch. Insect Biochem. Physiol.* 30:133 (1995). cDNA molecules from a late-larval cDNA library were also obtained from this region. One transcriptional unit was found to be located very close to the P-element insertion site.

As described herein, cDNA molecules encoding the Met JHR gene were isolated from a Drosophila ovary cDNA library. The genomic DNA for the Met gene was found in a 6.234 Kb St-H fragment, which is shown in FIG. 2 (SEQ ID NO:1).

Figure 3A:
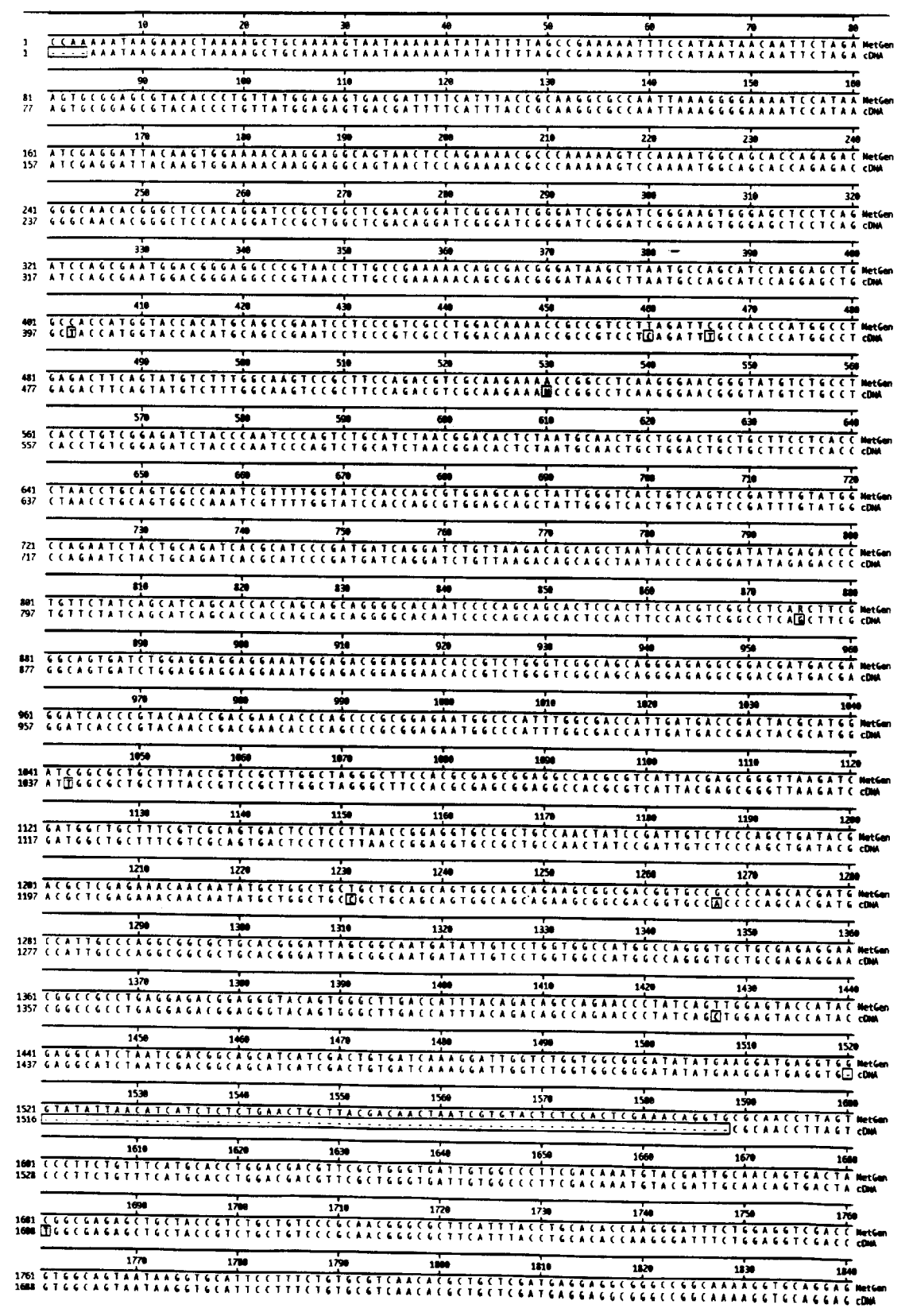
Figure 3B:
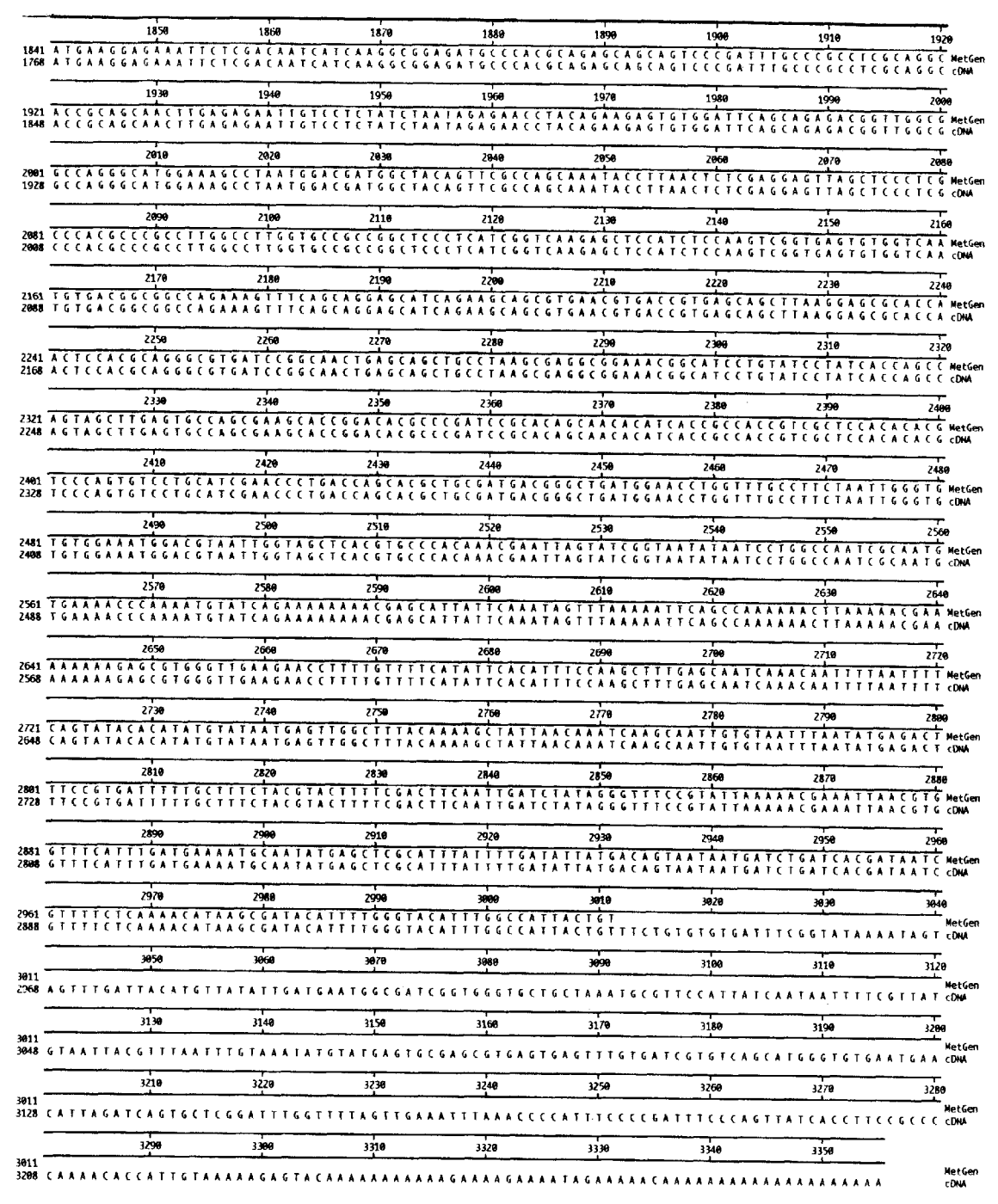
Figure 7:
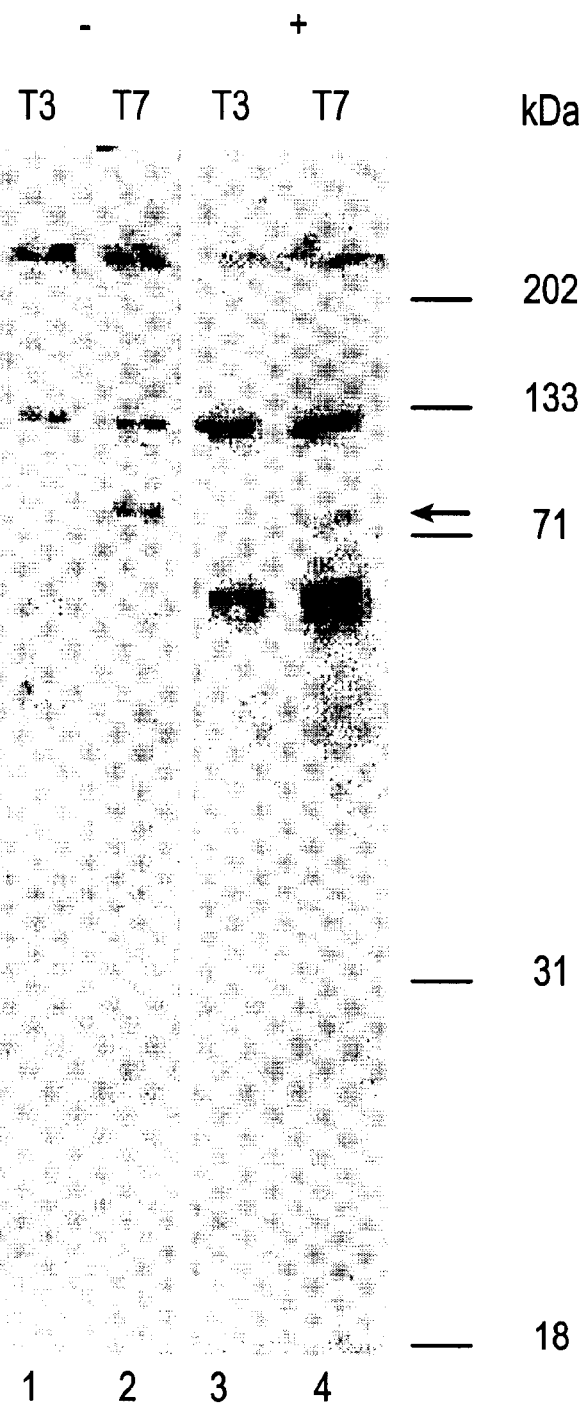
FIG. 7 shows in vitro transcription and translation of the Met-JHR cDNA to produce a protein band that migrates at about 78,000 daltons. The reaction uses T3 or T7 polymerase, in the presence (+) or absence (−) of microsomal membranes. The Met-JHR gene is transcribed only by the T7 polymerase (lanes 2 and 4) and it does not appear to be post-translationally modified (proteolytically processed or glycosylated) by the microsomal membranes (lane 2 vs. lane 4).

By comparing the genomic DNA with a cDNA of 3.282 Kb, it was deduced that the genomic DNA sequence includes a 2.22 Kb open reading frame that is divided by one intron of 69 nucleotides (bases 1520 to 1588). SEQ ID NO:2. A 3.282 kB sequence that contains a Met JHR gene cDNA is shown in FIG. 3 (SEQ ID NO:3). The cDNA was used to transcribe and translate a protein that approximates the predicted size of the Met cDNA open reading frame, as shown in FIG. 7.

The 6.234 Kb segment comprises the intron (lower case letters; bases 2809–2878) and the Met-JHR open reading frame (base no. 1514 to base no. 3732). Also shown in FIG. 1 are the first (no. 1292) and last (no. 4301) bases of the genomic Met-JHR sequence in FIG. 3. The invention thus comprises isolated polynucleotides comprising a DNA sequence from base no. 1 though base no. 1291 of SEQ ID NO:1, or a DNA sequence from base no. 1 though base no. 1513 of SEQ ID NO:1, or a DNA sequence from base no. 3733 through base no. 6235 of SEQ ID NO:1, or a DNA sequence from base no. 4302 through base no. 6235 of SEQ ID NO:1.

Polynucleotides encoding the Met-JHR protein are obtained by screening cDNA or genomic libraries with polynucleotide probes having nucleotide sequences based upon SEQ ID NO:1 or SEQ ID NO:2. *Drosophila melanogaster* cDNA and genomic libraries are constructed according to standard methods. Optionally, libraries are obtained from commercial sources, such as the American Type Culture Collection (e.g., ATCC 37332 is a *D. melanogaster* genomic library).

Alternatively, the Met JHR gene is obtained by synthesizing polynucleotides using mutually priming long oligonucleotides. See, for example, Ausubel et al., (eds.), *CURRENT PROTOCOLS IN MOLECULAR BIOLOGY*, pages 8.2.8 to 8.2.13 (1990) ["Ausubel"]. Also, see Wosnick et al., *Gene* 60:115 (1987); and Ausubel et al. (eds.), *SHORT PROTOCOLS IN MOLECULAR BIOLOGY*, 3rd Edition, pages 8-8 to 8-9 (John Wiley & Sons, Inc. 1995). Established techniques using the polymerase chain reaction provide the ability to synthesize polynucleotides at least 2 kilobases in length. Adang et al., *Plant Molec. Biol.* 21:1131 (1993); Bambot et al., *PCR Methods and Applications* 2:266 (1993); Dillon et al., "Use of the Polymerase Chain Reaction for the Rapid Construction of Synthetic Genes," in *METHODS IN MOLECULAR BIOLOGY, Vol. 15: PCR PROTOCOLS: CURRENT METHODS AND APPLICATIONS*, White (ed.), pages 263–268, (Humana Press, Inc. 1993); Holowachuk et al., *PCP Methods Appl.* 4:299 (1995).

The invention further comprise nucleotide sequences that hybridize with a Met-JHR polynucleotide of the invention under stringent conditions. Suitable hybridization conditions are discussed below.

"Hybridization" is used here to denote the pairing of complementary nucleotide sequences to produce a DNA—DNA hybrid or a DNA-RNA hybrid. Complementary base sequences are those sequences that are related by the base-pairing rules. In DNA, A pairs with T and C pairs with G. In RNA U pairs with A and C pairs with G.

Typically, nucleotide sequences to be compared by means of hybridization are analyzed using dot blotting, slot blotting, Northern or Southern blotting. Southern blotting is used to determine the complementarity of DNA sequences. Northern blotting determines complementarity of DNA and RNA sequences. Dot and Slot blotting can be used to analyze DNA/DNA or DNA/RNA complementarity.

These techniques are well known by those of skill in the art. Typical procedures are described in *CURRENT PROTOCOLS IN MOLECULAR BIOLOGY* (Ausubel, et al., eds.) (John Wiley & Sons, Inc. 1995) at pages 2.9.1 through 2.9.20.

A probe is a biochemical labeled with a radioactive isotope or tagged in other ways for ease in identification. A probe is used to identify a gene, a gene product or a protein. Thus a polynucleotide probe can be used to identify complementary nucleotide sequences. An mRNA probe will hybridize with its corresponding DNA gene. An antisense "riboprobe" also will hybridize to is corresponding DNA gene.

Typically, the following general procedure is used to determine hybridization under stringent conditions. A Met-JHR polynucleotide according to the invention is immobilized on a membrane. A sample polynucleotide will be labeled and used as a "probe." Using procedures well known to those skilled in the art for blotting described above, the ability of the probe to hybridize with a nucleotide sequence according to the invention can be analyzed. Conversely, the sample polynucleotide is immobilized and a Met-JHR polynucleotide is used as a probe.

One of skill in the art will recognize that various factors can influence the amount and detectability of the probe bound to the immobilized DNA. The specific activity of the probe must be sufficiently high to permit detection. Typically, a specific activity of at least $10^8$ dpm/ug is necessary to avoid weak or undetectable hybridization signals when using a radioactive hybridization probe. A probe with a specific activity of $10^8$ to $10^9$ dpm/ug can detect approximately 0.5 pg of DNA. It is well known in the art that sufficient DNA must be immobilized on the membrane to permit detection. It is desirable to have excess immobilized DNA and spotting 10 ug of DNA is generally an acceptable amount that will permit optimum detection in most circumstances. Adding an inert polymer such as 10% (w/v) dextran sulfate (mol. wt. 500,000) or PEG 6000 to the hybridization solution can also increase the sensitivity of the hybridization. Adding these polymers has been known to increase the hybridization signal. See Ausubel, supra, at p 2.10.10.

To achieve meaningful results from hybridization between a first nucleotide sequence immobilized on a membrane and a second nucleotide sequence to be used as a hybridization probe, (1) sufficient probe must bind to the immobilized DNA to produce a detectable signal (sensitivity) and (2) following the washing procedure, the probe must be attached only to those immobilized sequences with the desired degree of complementarity to the probe sequence (specificity).

"Stringency," as used in this specification, means the condition with regard to temperature, ionic strength and the presence of certain organic solvents, under which nucleic acid hybridizations are carried out. The higher the stringency used, the higher degree of complementarity between the probe and the immobilized DNA.

"Stringent conditions" designates those conditions under which only polynucleotides that have a high frequency of complementary base sequences will hybridize with each other.

Exemplary stringent conditions are (1) 0.75 M dibasic sodium phosphate/0.5 M monobasic sodium phosphate/1 mM disodium EDTA/1% sarkosyl at about 42° C. for at least about 30 minutes, (2) 6.0M urea/0.4% sodium laurel sulfate/0.1% SSX at about 42° C. for at least about 30 minutes, (3) 0.1×SSC/0.1% SDS at about 68° C. for at least about 20 minutes, (4) 1×SSC/0.1% SDS at about 55° C. for about one hour, (5) 1×SSC/0.1% SDS at about 62° C. for about one hour, (6) 1×SSC/0.1% SDS at about 68° C. for about one hour, (7) 0.2×SSC/0.1% SDS at about 55° C. for about one hour, (8) 0.2×SSC/0.1% SDS at about 62° C. for about one hour, and (9) 0.2×SSC/0.1% SDS at about 68° C. for about one hour. See, e.g. *CURRENT PROTOCOLS IN MOLECULAR BIOLOGY* (Ausubel, et al., eds.) (John Wiley & Sons, Inc. 1995), pages 2.10.1–2.10.16 of which are hereby incorporated by reference and Sambrook, et al., *MOLECULAR CLONING. A LABORATORY MANUAL* (Cold Spring Harbor Press, 1989) at §§1.101–1.104.

While stringent washes are typically carried out at temperatures from about 42° C. to about 68° C., one of skill in the art will appreciate that other temperatures may be suitable for stringent conditions. Maximum hybridization typically occurs at about 20 to about 25° C. below the $T_m$ for DNA—DNA hybrids. It is well known in the art that $T_m$ is the melting temperature, or temperature at which two nucleotide sequences dissociate. Methods for estimating $T_m$ are well known in the art. See, e.g. Ausubel, supra, at page 2.10.8. Maximum hybridization typically occurs at about 10 to about 15° C. below the $T_m$ for DNA-RNA hybrids.

Naturally occurring variants of the Met-JHR gene and protein are included in the present invention. For example, variants of the Met-JHR gene are the result of naturally-occurring polymorphisms. For example, the genomic and cDNA for the Met-JHR differ by one amino acid residue due to polymorphism. Amino acid No. 274 is R in the genomic DNA and the corresponding amino acid in the cDNA is W. Other nucleotide differences between the genomic and cDNA are boxed in FIG. 3.

Sequence ambiguities also give rise to variants of the Met-JHR. In this regard, amino acid no. 103 deduced from the Met-JHR cDNA can be T or P. In the corresponding genomic DNA, amino acid no. 218 can be G or R. In addition, variants of the Met gene result from intron diversity. As used herein, "a Met-JHR alternatively-spliced isoform" is used to designate an isoform of the Met-JHR gene that results from alternate splicing due to the presence of an intron in this gene. In one isoform, there is no splicing and there is read through to the first stop codon, to produce a 1320 nucleotide-long sequence. This encodes a 439 amino acid protein (439 amino acids+TAA stop codon).

The skilled artisan will recognize that potential introns can be identified using various computer programs. Using one system, potential donor sites were recognized at nucleotides 549, 1517, 1586, and 2147 of the Met-JHR genomic DNA (3011 nucleotides). Acceptor sites were recognized at positions 260, 278, 651, 875, 1071, and 1192. Using a second system, donor sites in the Met-JHR open reading frame were identified at positions 320–334, 1288–1302, 1357–1371, 1431–1445, 1546–1560, and 1918–1932. Acceptor sites were identified at 274–314, 436–476, 494–534, 829–869, 950–990, 1676–1716, 1716–1756, 2009–2049 and 2076–2116. Using data such as this, potential alternatively spliced isoforms of the Met-JHR gene can be identified using routine optimization.

Additionally, variants of the Met-JHR can be produced ilthat contain conservative amino acid changes, compared with the parent receptor molecule. That is, variants can obtained that contain one or more amino acid substitutions of SEQ ID NO:4 or SEQ ID NO:5, in which an alkyl amino acid is substituted for an alkyl amino acid in the Met JHR amino acid sequence, an aromatic amino acid is substituted for an aromatic amino acid in the Met JHR amino acid sequence, a sulfur-containing amino acid is substituted for a sulfur-containing amino acid in the Met JHR amino acid sequence, a hydroxy-containing amino acid is substituted for a hydroxy-containing amino acid in the Met JHR amino acid sequence, an acidic amino acid is substituted for an acidic amino acid in the Met JHR amino acid sequence, a basic amino acid is substituted for a basic amino acid in the Met JHR amino acid sequence, or a dibasic monocarboxylic amino acid is substituted for a dibasic monocarboxylic amino acid in the Met JHR amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) cysteine and methionine, (4) serine and threonine, (5) aspartate and glutamate, (6) glutamine and asparagine, and (7) lysine, arginine and histidine. Of course other amino acid substitutions can be undertaken.

Conservative amino acid changes in the Met JHR can be introduced by substituting nucleotides for the nucleotides recited in SEQ ID NO:2 or SEQ ID NO:3. Such "conservative amino acid" variants can be obtained, for example, by oligonucleotide-directedmutagenesis, linker-scanning mutagenesis, mutagenesis using the polymerase chain reaction, and the like. Ausubel et al., supra, at pages 8.0.3–8.5.9; Ausubel et al. (eds.), *SHORT PROTOCOLS IN MOLECULAR BIOLOGY*, 3rd Edition, pages 8-10 to 8-22 (John Wiley & Sons, Inc. 1995). Also see generally, McPherson (ed.), *DIRECTED MUTAGENESIS: A PRACTICAL APPROACH*, IRL Press (1991). The ability of such variants to bind JH or an analog can be determined using any of the standard binding assays described herein.

In addition, routine deletion analyses can be performed to obtain "functional fragments" of the Met JHR. As an illustration, polynucleotides having the nucleotide sequence of SEQ ID NO:2 or 3 can be digested with Bal31 nuclease to obtain a series of nested deletions. The fragments are then inserted into expression vectors in proper reading frame, and the expressed polypeptide are isolated and tested for the ability to bind JH or an analog using a standard assay. One alternative to exonuclease digestion is to use oligonucleotide-directed mutagenesis to introduce deletions or stop codons to specify production of a desired fragment. Alternatively, particular fragments of a bHLH-PAS/JHR gene can be synthesized using the polymerase chain reaction. Standard techniques for functional analysis of proteins are described by, for example, Treuter et al., *Molec. Gen. Genet.* 240:113 (1993); Content et al., "Expression and preliminary deletion analysis of the 42 kDa 2–5A synthetase induced by human interferon," in *BIOLOGICAL INTERFERON SYSTEMS, PROCEEDINGS OF ISIR-TNO MEETING ON INTERFERON SYSTEMS*, Cantell (ed.), pages 65–72 (Nijhoff 1987); Herschman, "The EGF Receptor," in *CONTROL OF ANIMAL CELL PROLIFERATION*, Vol. 1, Boynton et al., (eds.) pages 169–199 (Academic Press 1985); Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995); and Meisel et al., *Plant Molec. Biol.* 30:1 (1996).

The skilled artisan will recognize that it is a matter of routine optimization to perform deletion analysis of the Met-JHR gene to ascertain the functions that are associated with certain domains, and to obtain corresponding functional fragments. One way to identify such fragments is to create chimeric proteins by swapping functional domains between bHLH-PAS/JHR and other members of the bHLH-PAS family. As explained in Example 2, the Met-JHR gene contains structures (sequences) that are associated with conserved functions in other proteins. For example, the bHLH region is involved in DNA binding and heterodimerization. The P/S/T region is involved in transactivation. Other regions are described in Example 2. Thus, the invention encompasses fragments of the Met-JHR gene that encode proteins that have one or more of these functions.

The present invention also contemplates functional fragments of Met gene that have conservative amino acid changes.

4. Expression of the Cloned Met Juvenile Hormone Receptor

To express the polypeptide encoded by the Met JHR gene, the DNA sequence must be operably linked to regulatory sequences controlling transcriptional expression in an expression vector and then, introduced into either a prokaryotic or eukaryotic host cell. In addition to transcriptional regulatory sequences, such as promoters and enhancers, expression vectors include translational regulatory sequences and a marker gene which is suitable for selection of cells that carry the expression vector.

Suitable promoters for expression in a prokaryotic host can be repressible, constitutive, or inducible. Suitable promoters are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacλpr, phoA, and lacZ promoters of *E. coli*, the α-amylase and the $\sigma^{28}$-specific promoters of *B. subtilis*, the promoters of the bacteriophages of Bacillus, Streptomyces promoters, the int promoter of bacteriophage lambda, the bla promoter of the β-lactamase gene of pBR322, and the CAT promoter of the chloramphenicol acetyl transferase gene. Prokaryotic promoters are reviewed by Glick, *J. Ind. Microbiol.* 1:277 (1987); Watson et al., *MOLECULAR BIOLOGY OF THE GENE*, 4th Ed., Benjamin Cummins (1987); Ausubel et al., supra, and Sambrook et al., supra.

A preferred prokaryotic host is *E. coli*. Suitable strains of *E. coli* include DH1, DH4α, DH5, DH5α, DH5αF', DH5αMCR, DH10B, DH10B/p3, DH11S, C600, HB101, JM101, JM105, JM109, JM110, K38, RR1, Y1088, Y1089, CSH18, ER1451, and ER1647 (see, for example, Brown (Ed.), *MOLECULAR BIOLOGY LABFAX*, Academic Press (1991)). An alternative preferred host is *Bacillus subtilus*, including such strains as BR151, YB886, MI119, MI120, and B170. See, for example, Hardy, "Bacillus Cloning Methods," in *DNA CLONING: A PRACTICAL APPROACH*, Glover (Ed.), IRL Press (1985).

Methods for expressing proteins in prokaryotic hosts are well-known to those of skill in the art. See, for example, Williams et al., "Expression of foreign proteins in *E. coli* using plasmid vectors and purification of specific polyclonal antibodies," in *DNA CLONING 2: EXPRESSION SYSTEMS*, 2nd Edition, Glover et al. (eds.), pages 15–58 (Oxford University Press 1995). Also see, Ward et al., "Genetic Manipulation and Expression of Antibodies," in *MONOCLONAL ANTIBODIES: PRINCIPLES AND APPLICATIONS*, pages 137–185 (Wiley-Liss, Inc. 1995); and Georgiou, "Expression of Proteins in Bacteria," in *PROTEIN ENGINEERING: PRINCIPLES AND PRACTICE*, Cleland et al. (eds.), pages 101–127 (John Wiley & Sons, Inc. 1996).

Expression vectors that are suitable for production of bHLH-PAS/JHR protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence.

A bHLH-PAS/JHR protein of the present invention can be expressed in insect, mammalian, and yeast cells. Preferably, receptor protein is produced in insect cells using a baculovirus system. Recombinant proteins expressed by baculoviruses in insect cells undergo correct posttranslational modification, including glycosylation, phosphorylation, palmitylation, myristylation, signal peptide cleavage, and intracellular transport. Suitable expression vectors are based upon the *Autographa californica* multiple nuclear polyhedrosis virus (AcMNPV), and contain well-known promoters such as Drosophila heat shock protein (hsp) 70 promoter, *Autographa californica* nuclear polyhedrosis virus immediate-early gene promoter (ie-7) and the delayed early 39K promoter, baculovirus p10 promoter, baculovirus polyhedrin promoter, and the *Drosophila metallothionein* promoter. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Tricoplusia ni* 5B14 cells, and Drosophila Schneider-2 cells. Established techniques for producing recombinant proteins in baculovirus systems are provided by Bailey et al., "Manipulation of Baculovirus Vectors," in *METHODS IN MOLECULAR BIOLOGY, Volume 7: GENE TRANSFER AND EXPRESSION PROTOCOLS*, Murray (ed.), pages 147–168 (The Humana Press, Inc. 1991), by Patel et al., "The baculovirus expression system," in *DNA CLONING 2: EXPRESSION SYSTEMS*, 2nd Edition, Glover et al. (eds.), pages 205–244 (Oxford University Press 1995), by Ausubel et al. (eds.), *SHORT PROTOCOLS IN MOLECULAR BIOLOGY*, 3rd Edition, pages 16–37 to 16–57 (John Wiley & Sons, Inc. 1995), by Richardson (ed.), *BACULOVIRUS EXPRESSION PROTOCOLS* (The Humana Press, Inc. 1995), and by Lucknow, "Insect Cell Expression Technology," in *PROTEIN ENGINEERING: PRINCIPLES AND PRACTICE*, Cleland et al. (eds.), pages 183–218 (John Wiley & Sons, Inc. 1996).

Suitable yeast expression vectors include, but are not limited to, YEp and YIp vectors. Hill et al. *Yeast* 2:163 (1986). Any suitable recombinant cloning vectors may be used for introducing foreign DNA sequences into yeast. Such vectors may include one or more replication systems for cloning or expression, one or more markers for selection in the host (e.g., prototrophy or antibiotic resistance) and one or more expression cassettes. Examples of yeast promoters include, but are not limited to, the metallothionein promoter (CUP1), triosephosphate dehydrogenase promoter (TDH3), 3-phosphoglycerate kinase promoter (PGK), glyceraldehyde-3-phosphate dehydrogenase (GAPDH) promoter, galactokinase (GALI) promoter, galactoepimerase promoter and alcohol dehydrogenase (ADH) promoter.

Yeast host cells may be transformed using any suitable method, including, but not limited to, methods that employ calcium phosphate, lithium salts, electroporation, and spheroplast formation. Sherman et al, *Methods in Yeast Genetics*, Cold Spring Harbor Laboratory (1982). Suitable host cells include, but are not limited to, *Saccharomyces cerevisiae* and *Schizosaccharomyces pombe*.

Examples of mammalian host cells include human 1 embryonic kidney cells (293-HEK; ATCC CRL 1573), baby hamster kidney cells (BHK-21; ATCC CRL 8544), canine kidney cells (MDCK; ATCC CCL 34), Chinese hamster ovary cells (CHO-K1; ATCC CCL61), rat pituitary cells (GH$_1$; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene [Hamer et al., *J. Molec. Appl. Genet.* 1:273 (1982)], the TK promoter of Herpes virus [McKnight, *Cell* 31:355 (1982)], the SV40 early promoter [Benoist et al., *Nature* 290:304 (1981)], the *Rous sarcoma* virus promoter [Gorman et al., *Proc. Nat'l Acad. Sci. USA* 79:6777 (1982), the cytomegalovirus promoter [Foecking et al., *Gene* 45:101 (1980)], and the mouse mammary tumor virus promoter. See, generally, Etcheverry, "Expression of Engineered Proteins in Mammalian Cell Culture," in *PRO-*

TEIN ENGINEERING: PRINCIPLES AND PRACTICE, Cleland et al. (eds.), pages 163–181 (John Wiley & Sons, Inc. 1996).

Alternatively, a prokaryotic promoter, such as the bacteriophage T3 RNA polymerase promoter, can be used to control fusion gene expression if the prokaryotic promoter is regulated by a eukaryotic promoter. Zhou et al., *Mol. Cell. Biol.* 10:4529 (1990) Kaufman et al., *Nucl. Acids Res.* 19:4485 (1991).

An expression vector can be introduced into host cells using a variety of techniques including calcium phosphate transfection, liposome-mediated transfection, electroporation, and the like. Preferably, transfected cells are selected and propagated wherein the expression vector is stably integrated in the host cell genome to produce stable transformants. Techniques for introducing vectors into eukaryotic cells and techniques for selecting stable transformants using a dominant selectable marker are described, for example, by Ausubel and by Murray (ed.), *GENE TRANSFER AND EXPRESSION PROTOCOLS* (Humana Press 1991).

5. Isolation of the Cloned Met Juvenile Hormone Receptor and Production of Anti-Receptor Antibodies (a) Isolation of Recombinant Receptor Protein General methods for recovering protein produced by a bacterial system is provided by, for example, Grisshammer et al., "Purification of over-produced proteins from *E. coli* cells," in *DNA CLONING 2: EXPRESSION SYSTEMS*, 2nd Edition, Glover et al. (eds.), pages 59–92 (Oxford University Press 1995). Established techniques for isolating recombinant proteins from a baculovirus system are described by Richardson (ed.) *BACULOVIRUS EXPRESSION PROTOCOLS* (The Humana Press, Inc. 1995).

bHLH-PAS/JHR proteins can be purified using. standard methods that have been used to purify JH binding proteins, including gel filtration, ion exchange chromatography, isoelectric focusing, hydroxylapatite chromatography, and affinity chromatography. See, for example, Goodman et al., "Development of Affinity Chromatography for Juvenile Hormone Binding Proteins," in *JUVENILE HORMONE BIOCHEMISTRY*, Pratt et al. (eds.), pages 365–374 (Elsevier/North-Holland Biomedical Press 1981); Goodman et al., "Juvenile Hormone Cellular and Hemolymph Binding Proteins," in *COMPREHENSIVE INSECT PHYSIOLOGY AND PHARMACOLOGY*, Volume 7, Kerkut et al. (eds.) pages 491–510 (Pergamon Press 1985). Moreover, general affinity chromatography techniques are provided by, for example, Dean et al., *AFFINITY CHROMATOGRAPHY: A PRACTICAL APPROACH* (IRL Press 1985).

As an alternative, anti-Met JHR antibodies, obtained as described below, can be used to isolate large quantities of Met JHR by immunoaffinity purification.

(b) Preparation of Anti-Met Juvenile Hormone Receptor Antibodies and Fragments Thereof Antibodies to Met JHR can be obtained using the product of an expression vector as an antigen. Polyclonal antibodies to such receptor protein can be prepared using methods well-known to those of skill in the art. See, for example, Green et al., "Production of Polyclonal Antisera," in *IMMUNOCHEMICAL PROTOCOLS* (Manson, ed.), pages 1–5 (Humana Press 1992). Also see, Williams et al., "Expression of foreign proteins in *E. coli* using plasmid vectors and purification of specific polyclonal antibodies," in *DNA CLONING 2: EXPRESSION SYSTEMS*, 2nd Edition, Glover et al. (eds.), pages 15–58 (Oxford University Press 1995).

Alternatively, an anti-Met JHR antibody can be derived from a rodent monoclonal antibody (MAb). Rodent monoclonal antibodies to specific antigens may be obtained by methods known to those skilled in the art. See, for example, Kohler et al., *Nature* 256:495 (1975), and Coligan et al. (eds.), *CURRENT PROTOCOLS IN IMMUNOLOGY, VOL.* 1, pages 2.5.1–2.6.7 (John Wiley & Sons 1991) ["Coligan"]. Also see, Picksley et al., "Production of monoclonal antibodies against proteins expressed in *E. coli*," in *DNA CLONING 2: EXPRESSION SYSTEMS*, 2nd Edition, Glover et al. (eds.), pages 93–122 (Oxford University Press 1995).

Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1–2.7.12 and pages 2.9.1–2.9.3. Also, see Baines et al., "Purification of Immunoglobulin G (IgG)," in *METHODS IN MOLECULAR BIOLOGY, VOL.* 10, pages 79–104 (The Humana Press, Inc. 1992).

For particular uses, it may be desirable to prepare fragments of anti-Met JHR antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. Nos. 4,036,945 and 4,331,647 and references contained therein. Also, see Nisonoff et al., *Arch Biochem. Biophys.* 89:230 (1960); Porter, *Biochem. J.* 73:119 (1959), Edelman et al., in *METHODS IN ENZYMOLOGY VOL.* 1, page 422 (Academic Press 1967), and Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described in Inbar et al., *Proc. Nat'l Acad. Sci. USA* 69:2659 (1972). Alternatively, the variable chains can be linked by an intermolecular disulfide bond or cross-linked by chemicals such as glutaraldehyde. See, for example, Sandhu, *Crit. Rev. Biotech.* 12:437 (1992).

Preferably, the Fv fragments comprise $V_H$ and $V_L$ chains which are connected by a peptide linker. These single-chain antigen binding proteins (sFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology* 2:97 (1991). Also see Bird et al., *Science* 242:423 (1988), Ladner et al., U.S. Pat. No. 4,946,778, Pack et al., *Bio/Technology* 11:1271 (1993), and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2:106 (1991); Courtenay-Luck, "Genetic Manipulation of Monoclonal Antibodies," in *MONOCLONAL ANTIBODIES: PRODUCTION, ENGINEERING AND CLINICAL APPLICATION*, Ritter et al. (eds.), pages 166–179 (Cambridge University Press 1995); and Ward et al., "Genetic Manipulation and Expression of Antibodies," in *MONOCLONAL ANTIBODIES: PRINCIPLES AND APPLICATIONS*, Birch et al., (eds.), pages 137–185 (Wiley-Liss, Inc. 1995).

Researchers have found that an anti-receptor monoclonal antibody can mimic the cognate ligand by binding with the ligand-binding domain of the receptor. For example, ligand-mimicking antibodies have been made that bind with a granulocyte-macrophage colony-stimulating factor receptor, a very low-density lipoprotein receptor, and a receptor encoded by the c-erbB-2 gene. Von Feldt et al., *Immunol. Res.* 13:96 (1994); Shawver et al., *Cancer Res.* 54:1367 (1994); Pfistermueller et al., *FEBS Lett.* 396:14 (1996). Antibodies that mimic JH can be screened, for example, using a competition assay with radiolabeled ligand, such as juvenile hormone, and JHR, as described below.

6. Use of a bHLH-PAS/JHR Protein to Screen for Juvenile Hormone Analogs and Antagonists a. In vitro Binding Assays Potential insecticides can be tested in vitro by determining the ability of a test compound to displace detectably-labeled JH (or labeled JH analog) from a lrecombinant bHLH-PAS/JHR. Assays designed to measure the binding of a ligand to a JH binding protein are well-established. See, for example, Ozyhar et al., *Experientia* 42:1276 (1986); Shemshedini and Wilson, *Insect Biochem.* 18:681 (1988); Shemshedini et al. , *J. Biol. Chem.* 265:1913 (1990); Shemshedini and Wilson, *Proc. Nat'l Acad. Sci. USA* 87:2072 (1990); Chang et al., *Comp. Biochem. Physiol.* 99C:15 (1991); Glinka et al., *Insect Biochem. Molec. Biol.* 25:775 (1995). However, the insecticide screening assay described herein uses a recombinantly-produced bHLH-PAS/JHR protein to test binding.

In one form of assay, a recombinant bHLH-PAS/JHR is incubated with labeled ligand, and a potential juvenile hormone-type insecticide is tested by measuring the ability of the compound to displace the labeled ligand bound to the recombinant receptor protein. Ligands, such as JH III or an analog, can be detectably labeled with a radiolabel, fluorescent label, a chemiluminescent label, or a bioluminescent label. Examples of suitable radioligands include ligands having one or more atoms enriched in a radioisotope, and ligands that are covalently coupled to a radioisotope label. Examples of radioisotopes that can be used to enrich ligands include $^3$H and $^{14}$C. Examples of radioisotopes that may be used to covalently label ligands include $^{125}$I, $^{131}$I, $^{32}$P, $^{35}$S, $^{51}$Cr, $^{36}$Cl, $^{57}$Co, $^{58}$Co, $^{59}$Fe, and $^{58}$Se.

Suitable radiolabeled ligands include [$^3$H]10R-JH III and [$^3$H]methoprene. Radiolabeled JH III is commercially available. Radiolabeled ligands can also be obtained by chemical synthesis or biosynthesis, as described by Jennings et al., "Labeled Compounds in Juvenile Hormone Research," in *JUVENILE HORMONE BIOCHEMISTRY*, Pratt et al. (eds.) pages 375–380 (Elsevier/North-Holland Biomedical Press 1981).

As an illustration, an insecticide screening assay is performed in a physiologically-compatible buffer such as 10 mM Tris-HCl (pH 8.0), 100 mM KCl, 1 mM EDTA, 10% glycerol and 100 µg/ml bovine serum albumin. The test compound and labeled ligand (i.e., JH or an analog) is dissolved in an alcohol, such as methanol, or in dimethyl-sulfoxide and diluted with assay buffer.

Recombinant bHLH-PAS/JHR is diluted with the assay buffer and incubated with [$^3$H]10R-JH III at room temperature for about thirty minutes. Two hundred microliters 200 µl of assay buffer is added to test tubes, followed by 100 µl of solution containing recombinant bHLH-PAS/JHR bound with the radiolabeled ligand (about 12,000 dpm per tube or 0.03 pmol). As a control, aliquots of JH III, about 0.023 pmol to about 3 pmol, are added to parallel series of tubes. After mixing the solutions, the tubes are allowed to incubate for thirty minutes at room temperature. The skilled artisan will recognize that this assay also may be carried out with JHI, JHII and methoprene as binding competitors, at concentrations of 0.023 pmol to 30 pmol. This serves as a measure of the specificity and apparent affinity of the bHLH-PAS/JHR for binding JHIII.

Hydroxyapatite (HAP) is used to separate bound radiolabeled ligand from free radiolabeled ligand, according to the procedure of Roberts et al., *Molec. Cell. Endocrinol.* 31:53 (1983), or a modification of the Roberts procedure. Briefly, 0.5 ml of 5% HAP (DNA-Grade HTP; Bio-Rad) suspension in HAP buffer (10 mM Tris-HCl [pH 8.0], 10 mM KH$_2$PO$_4$, 1 mM EDTA) was added. After gently vortexing the tubes, the solutions are incubated at 30 minutes at room temperature, and then filtered through glass fiber filters (e.g. , Whatman 934-AH). The filters are rinsed four times with HAP buffer, placed in vials, and dried at 100° C. for about ten minutes. Scintillation fluid is then added to the tubes and allowed to incubate overnight before counting. Nonspecific binding is measured in the presence of 100-fold excess of unlabeled ligand (i.e., JH III in this example). The results of the competition binding assay are analyzed using established methods, such as Scatchard analysis. Scatchard, *Ann. N.Y. Acad Sci.* 51:660 (1949)

Although the insecticide screening assay has been described in considerable detail, it will be obvious to the practitioner in the art that modifications can be practiced within the scope of this invention. For example, the pH and the solution components can be modified, the time and temperature values may be varied, and modifications can be made in the form and material (e.g., glass, plastic, etc.) of vessels used to perform the assay. Moreover, receptor-ligand complexes can be separated from unbound ligand by using centrifugation instead of filtering, or by using a suspension of charcoal-dextran instead of HAP. Alternatively, a "scintillation proximity assay" (SPA) can be used for screening insecticides. This technique provides sensitivity and minimal manipulation. The SPA involves the use of solid scintillant beads that emit photons when in proximity to a radioligand. Bosworth et al. *Nature* 341:167 (1989). Attachment of binding protein to the beads obviates the need for separating bound from free radioligand because the signal emitted by the free radioligand is quenched by aqueous surroundings. Only radioligand that is bound to its receptor will generate a signal. Amersham sells a variety of beads, such as beads coated with lectins (e.g., ConA, wheat germ agglutinin, and lecithin) that will bind receptor protein.

In one variation of the insecticide screening assay, recombinant bHLH-PAS/JHR protein is preincubated with test compound, and then incubated with a labeled photoaffinity analog of juvenile hormone, such as epoxy farnesyl diazoacetate. In this assay, a test compound that binds with the bHLH-PAS/JHR protein will protect the protein from the photoaffinity label. Techniques for photoaffinity labeling of JH binding proteins are described, for example, by Shemshedini et al., *J. Biol. Chem.* 265:1913 (1990), and by Prestwich et al., "Hot JH: Using Radioligands and Photoaffinity Labels to Decipher the Molecular Action of Juvenile Hormone," in *INSECT JUVENILE HORMONE RESEARCH: FUNDAMENTAL AND APPLIED APPROACHES*, pages 247–256 (INRA 1992).

In a second variation of the insecticide screening assay, recombinant bHLH-PAS/JHR protein is incubated with a detectably labeled test compound, such as a radiolabeled test compound. The objective of this assay is to measure the binding of the test compound to the bHLH-PAS/JHR.

In a third variation of the insecticide screening assay, a first recombinant bHLH-PAS/JHR protein and a second heterodimeric partner of bHLH-PAS/JHR are incubated with a labeled test compound. The objective of this assay is to measure the binding of the test compound to the bHLH-PAS/JHR—heterodimeric partner complex.

According to another approach to insecticide screening, antibodies or antibody fragments are used that mimic JH by binding to the ligand-binding domain of the bHLH-PAS/JHR. Competition assays can be performed in which either the antibody (or antibody fragment) or the test compound is detectably labeled. The production of such antibody ligand mimics is discussed above.

The skilled artisan will recognize that compounds that bind a bHLH-PAS/JHR protein, identified with the above-described in vitro assays, may be agonists or antagonists. The characterization of a compound as agonist or antagonist is carried out using the in vivo assays described below.

b. In vivo Binding Assays

In addition to such in vitro assays, recombinant bHLH-PAS/JHRs can be used to screen insecticides in in vivo systems. As an illustration, Arnold et al., *Environ. Health Perspect.* 104:544 (1996), describe a screening assay for xenoestrogens, such as o,p'-DDT, in which transfected yeast cells express the human estrogen receptor and contain a LacZ gene under the control of two estrogen response elements.

A suitable in vivo assay for screening insecticides comprised incubating test compounds with yeast strains engineered to contain a functionally expressed Met-JHR. Functional expression can be achieved by using a one-hybrid or two-hybrid system. Luban et al. *Curr. Opin. Biotechnol.*, 6:59 (1995); Rowlands et al. *Pharmacol. & Toxicol.* 76:328 (1995); Yamaguchi et al. *Biochem. Pharmacol.* 50(8):1295 (1995).

Suitable vectors for in vivo assays include, but are not limited to, yeast, mammalian, and insect expression vectors. See, for example, Mak et al. *J. Biol. Chem.* 264:21653 (1989) and McDonnell et al. *Mol Cell. Biol.* 9:3519 (1989). In yeast, recombinant protein is expressed as an in-frame fusion to ubiquitin and an endogenous yeast ubiquitinase cleaves the fusion protein to release mature recombinant protein. Promoter such as TDH (constitutive) and CUP1 (copper inducible) may be used. In mammalian cells, a two-hybrid system has been used to test candidate transcriptional activators. Boudjelal et al. *Genes & Dev.* 11:2502 (1997). Boudjelal expressed fusions of the GAL4 amino terminus (147 aa encode DNA BD, dimerization domain, and nuclear localization signal) or the estrogen receptor DNA BD, and candidate TADs. These constructs were expressed in COS cells containing a reporter construct.

Two-Hybrid Assays—Luban et al. *Curr. Opin. Biotechnol.*, 6:59 (1995) describes a two hybrid system. Any pair of proteins that interact with each other can be used to bring together separate DNA-binding (DNA BD) and trans-activation domains (TAD) to reconstitute a transcriptional activator. The two-hybrid system is used to study protein-protein interactions. Thus, in a typical application, two DNA constructs are used: (1) encodes protein X fused to a DNA BD (e.g., from GAL4) (hybrid #1) and (2) encodes protein Y is fused to an AD (e.g., from GAL4) (hybrid #2). A third construct is included which comprises a reporter gene under the control of a corresponding response element (e.g., from GAL4). If proteins X and Y functionally interact, they will then bind to the GAL4 response element and stimulate expression of the reporter gene, by interacting with the GAL4 response element. If the reporter gene is not expressed, then a third (heteromultimeric partner) may be required.

In one version of a two-hybrid system, (1) Met-JHR is fused to one of the two-hybrid system proteins (DNA BP or a ADP) and (2) the heterodimeric partner of Met-JHR (which can be identified by a two-hybrid screen) is fused to the other protein of the two-hybrid system. Expression of the reporter gene, fused to the corresponding response element, will be effected if JH or a JH analog promotes the association between the Met-JHR protein and its heterodimeric receptor. See Ozenberger et al. *Molecular Endocrinology*, 9: 1321 (1995) and Lao et al. *Mol. Endocrin.* 11:366 (1997).

In another two hybrid system, a bHLH-PAS/JHR is expressed as a fusion protein with a DNA BP, a second plasmid expresses the bHLH-PAS/JHR protein as a fusion protein with an AD, and an appropriate reporter gene is also transfected into the cell. Treatment with JH would brings the two monomers to form an active homodimeric complex.

One-Hybrid Assays—In a one-hybrid system, there is only one hybrid protein comprising a candidate binding protein and all or part of a protein having a DNA BD and an AD. One variation of the 1-hybrid system involves the use of a small molecular weight molecule, such as Dioxin. Dioxin binds the AhR (also called the dioxin receptor) and will activate a GAL4-AhR construct. See Rowlands et al. *Pharmacol. & Toxicol.* 76:328 (1995). Rowlands' GAL4-AhR construct was "constitutively" active in yeast cells. In other words, the construct expressed a protein that turned on transcription of a LacZ reporter gene (LacZ fused to a GAL4 response element) in the absence of ligand. However, the addition of dioxin enhanced transactivation. Additionally, Whitelaw fused the DNA BD of the glucocorticoid receptor to the AhR and transformed CHO mammalian cells with this construct. *Mol. Cell. Biol.* 14:8343 (1991). The addition of dioxin to these cells induced expression of a reporter gene linked to a glucocorticoid response element. If a recombinant protein X comprises a TAD, then fusing X to a DNA BD may produce a constitutively active construct (e.g., GAL4 DNA BD/X-AD). Such a construct can be used to screen for antagonists. The addition of an antagonist will inhibit expression of a reporter gene linked to a GAL4 response element.

In another assay, the GAL4 DNA BD/X-AD is trascriptionally silent unless it is activated by another component. In a one-hybrid system, the heteromultimeric partner is consitutively expressed from another plasmid. A reporter plasmid contains a GAL4 response element linked to a reporter gene. Antagonists are screened for their ability to inhibit expression of the reporter gene.

Thus in another embodiment of the one-hybrid system, a bHLH-PAS/JHR is fused to the GAL4 DNA BD and an appropriate reporter plasmid is also transfected into the cell (e.g., GAL4 response element fused to a reporter gene). Treatment of the cell with JH results in induction of reporter gene expression if JH specifically binds bHLH-PAS/JHR.

If a heterodimeric partner is necessary for activation, it is expressed from a separate plasmid. The bHLH-PAS/JHR-GAL4 DNA BD fusion protein forms a heterodimer with the partner and upon addition of JH, the complex would activate transcription.

One- and Two-hybrid System Components—Truncated forms of Met-JHR and chimeras of Met-JHR with other bHLH-PAS proteins can be made and expressed in the one- or two-hybrid system. For example, removal of the bHLH domains before making the fusions may be desirable. The skilled artisan will recognize that functional fragments, as described above, are suitable for use in the in vivo assays. For example, a DNA BD of a bHLH-PAS/JHR protein may be fused to the AD of a second protein. This allows screening compounds that interfere with DNA binding by a bHLH-PAS/JHR protein. Furthermore, truncated forms of heterodimeric partners may also be suitable for use in the above-described assays.

Suitable heterodimeric partners for a bHLH-PAS/JHR include, but are not limited to, DARNT (a bHLH-PAS protein) and ultraspiracle, a nuclear orphan/steroid receptor. Drosophila has at least three bHLH-PAS proteins, Sim, Trh, and DARNT. Zelzer et al. presented evidence that Sim and Trh each form heterodimenrs with DARNT. *Genes & Dev.* 11:2079 (1997).

Suitable reporter polypeptide for use in the above-described assays include, but are not limited to, β-galactosidase derived from *E. coli* (LacZ); genes conferring sensitivity to a chemical such as CYH2, cycloheximide sensitivity, and CAN1, canavanine sensitivity, arginine permease derived from *S. cerevisiae* (CAN1). The expression of these reporter genes in the presence of the toxic substrate (cycloheximide, etc.) results in the suppression of cell growth. This is convenient for looking for antagonist compounds, i.e., compounds that permit cell growth. This is referred to as a "rescue screen." Other suitable reporter polypeptide include those involved in nucleoside and amino acid metabolism, such as the products of the URA3, LEU2, LYS2, HIS3, HIS4, TRP1, and ARG4 gene; polypeptide that confer resistance to drugs such as hygromycin, tunicamycin, cyclohexamide, and neomycin; and green fluroescence protein (GFP). Guthrie et al. *Meth. Enzymol.* vol. 194 (1991); Prasher, *Trends Gen.* 11:320 (1995). Detection of reporter gene expression is achieved using methods that are well-known to the skilled artisan.

Suitable transcription activation proteins include, but are not limited to, Gal4, Gcn4, Hap1, Ard1, Swi5, Ste12, Mem1, Yap1, Ace1, Ppr1, Arg81, Lac9, Qa1F, VP16, LexA, non-mammalian nuclear receptors (e.g., ecdysone) or mammalian nuclear receptors (e.g., estrogen, androgen, glucocorticoids, mineralocorticoids, retinoic acid and progesterone. See also Picard et al. *Gene* 86:257 (1990)

Suitable TADs include, but are not limited to, those from GAL4, Gcn4 or Adr1. A DNA binding protein domain can be substituted for the DNA binding domain of the transactivational activation protein, if the recognition sequences operatively associated with the reporter gene are correspondingly engineered. For example, non-yeast DNA binding proteins are mammalian steroid receptors and bacterial LexA. See Wilson et al. *Science* 252:1296 (1990).

7. Isolation of Additional Juvenile Hormone Receptor Genes

The nucleotide sequences of the Met JHR gene and antibodies to the receptor provide a means to isolate additional bHLH-PAS/JHR genes from other insects. Such genes can encode receptors specific for JH molecules of various species, including insects of the orders Coleoptera (e.g.,root worm, cigarette beetle, potato beetle, cotton boll weevil, and grain pests) Siphonaptera (fleas), Orthoptera (roaches), Isoptera (termites), Thysanoptera (thrips), Lepidoptera (butterflies and moths), Hemiptera (junebugs), Hymenoptera (ants), and Diptera (flies). In regard to the order Hemiptera, insects of the suborders Heteroptera (e.g., true bugs, stink bugs, and tarnished plant bug) and Homoptera (e.g., aphids, white flies, scale insects, and leaf hoppers) are of particular interest. Examples of suitable insects in the order Lepidoptera include species in the genera Spodoptera (e.g. *S. lieeralis, S. exigua,* and *S. frugiperta*), Mamestra (e.g., *M. brassica,* the cabbage moth), Plutella (e.g., *P. xylostella,* the diamondback moth), Pieris (e.g., *P. rapae,* the cabbage butterfly), Heliothis (e.g., *H. zea,* the corn earworm, as well as the bollworm and tobacco budworm). Suitable insects of the order Diptera include flies, such as horn fly, fruit fly, screwworm fly, blow fly, mosquito, Mediterranean fruit fly, biting midge, black fly, horse fly, deer fly, leaf miner, housefly, bot fly and warble fly.

For example, bHLH-PAS/JHR genes can be isolated from agricultural pests, including insects of the genera Ceroplastes (e.g., *Ceroplastes floridensis,* Florida wax scale), Saissetia (e.g., *Saissetia oleae,* black scale), Aonidiella (e.g., *Aonidiella aurantii,* California red scale), Chrysomphalus (e.g., *Chrysomphalus aonidum,* Florida red scale), Dacus (e.g., *Dacus oleae,* olive fruit fly), Megaselia (e.g., *Megaselia alterata,* mushroom hump-backed fly), Lycoriella (e.g., *Lycoriella auripila,* mushroom fungus gnat), Schistocerca (e.g., *Schistocerca gregaria,* desert locust), Diatraea (e.g., *Diatraea grandiosella,* Southwestern corn borer), Achoea (e.g., *Achoea janata,* castor semi-looper), Spodoptera (e.g., *Spodoptera littoralis,* Egyptian cotton leaf worm), and Mamestra (e.g., *Mamestra brassicae,* cabbage armyworm) bHLH-PAS/JHR genes can also be isolated from stored product pests, including insects of the genera Tribolium (e.g., *T. castaneum* [red flour beetle], *T. confusum* [confused flour beetle]), Tenebrio (e.g., *Tenebrio molitor,* yellow mealworm), Rhyzopertha (e.g., *Ryzopertha dominica,* lesser grain borer), Sitophilus (e.g., *Sitophilus oryzae,* rice weevil), Oryzaephilus (e.g., *Oryzaephilus surinamensis,* saw-toothed grain beetle) Plodia (e.g., *Plodia interpunctella,* Indian meal moth), and Sitotroga (e.g., *Sitotroga cerealella,* angoumois grain moth). Suitable sources for bHLH-PAS/JHR genes also include forest insect pests, such as Choristoneura (e.g., *Lamentria dispar* (Gypsy moth), *C. fumiferana* [Eastern spruce budworm], *C. occidentalis* [Western spruce budworm]), Lambdina (e.g., *Lambdina fiscellaria,* Eastern hemlock looper), and Dendroctonus (e.g., *D. pseudotsugae* [Douglas fir beetle], *D. frontalis* [Southern pine beetle]).

bHLH-PAS/JHR genes can also be isolated from insects considered to be of public and veterinary significance, as well as insects simply considered as a nuisance. Examples include mosquito species (e.g., *Culex pipiens, Aedes aegypti, Anopheles albimanus*, as well as *A. albopictus* (tiger mosquito) and *C. tarsalis* (swamp marsh mosquito)), blackfly species (e.g., *Simulium venustum, Prosimulium mixtum*), dog ticks (e.g., *Ctenocephalides canis* and *Dermacentor andersoni*), cattle ticks (e.g., *Boophilus microplus*), lice (insects of the orders Mallophaga or Anoplura), as well as insects of the genera Haematobia (e.g., *Haematobia irritans*, horn fly), Musca (e.g., *M. autumnalis* [face fly], *M. domestica* [house fly]), Glossina (e.g., *G. palpalis, G. morsitanstsete* [tsetse fly]), Melophagus (e.g., *Melophagus ovinus*, sheep ked), Monomorium (e.g., *Monomorium pharaonis*, Pharaoh's ant), Solenopsis (e.g., *Solenopsis invicta*, imported fire ant), an Reticulitermes (e.g., *Reticulitermes flavipes*, Eastern subterranean termite).

Lepidopteran species of interest include, but are not limited to: other Heliothia species, such as the American bollworm, *H. armigera* and the bollworm, *H. punctigera*; lepidopteran species of the genus Spodoptera, e.g., the Egyptian cotton leafworm, *S. litteralia*, the best armyworm, *S. exiga*; the fall armyworm, *S. fruciperda*; the cutworm, *B. litura*, the rice swarming caterpillar, *S. muritania* and the southern armyworm, *S. eridania*; and other miscellaneous lepidopterans, e.g., the pink bollworm, *Pectinophora gossypiella*; the spiny bollworm, *Barius insulana*, the cotton leafworm, *Alabama argillacea*; the leaf perforator, *Bucculatris thurberiella*; the tomato fruitworm, *Helicoverpa sea*; the diamondback moth, *Plutella xylostella*; the cabbage looper, *Trichoplasia ni*; the imported cabbageworms *Hellula undalis* and *Hellula rogatalis*; the black cutworm, *Agrotis ipsilon*; the corn earworm, *Ostrinia nubalis*; the tomato pinworm, *Keiferea lycopersicella*; the tomato hornworm, *Manduca sexta* and *Manduca guinquemaculata*; the velvet bean caterpillar, *Anticarsia gemmatalis*; the green oliveworm, *Plathypena scabra*; the soybean looper, *Pseudoplusia includens*; the saltmarsh caterpillar, *Estigmene acrea*; the leaf miner, *Epinotia meritana*; the codling moth, *Cydia pomonella*; the oblique banded leafroller, *Choristoneura rosaceana*; grape berry moth, *Lobesia botrans*; currant tortrix, *Pandemis cerasana*; spotted tentiform leafminer, *Phyllonocytes blancardella*; grape leafroller spargano-this pilleriana; tufted bud apple moth, *Platynota idacusalis*; red banded leafroller, *Argyrotaenea velutinana*; oriental fruit moth, *Grapholitha molesta*; Southwestern corn borer, *Diatrea grandiosella*; rice leafrollers, *Chaphalocrocis medinalis, Marasmia exiqua* and *Marasmia patnalis*; striped borer, *Chilo suppressalis*; dark headed stem-borer, *Chilo polychrysis*; yellow stem borer, *Scirophaga incatulae*; white stem borer, *Scirophaga innotata*; and pink stem borer, *Sesamia inferens*.

Non-lepidopteran species include the Colorado potato beetle *Leptinotarsa decimlineator*, the boll weevil, *Anthonomus grandis*; the Southern corn rootworm, *Diabrotica undecimpunctata*; the Japanese beetle, *Popillia japonica*; plum curculio, *Conotrachelus nenuphar*; brown planthopper, *Nilaparvata lugens*; green leafhopper, *Naphotettix virescens*; potato leafhopper, *Empoasca abruta*; cotton aphid, *Aphis gossypii*; green peach aphid, *Myzus persicae*; sweetpotato whitefly, *Bemisia tabaci*; imported fireant, *Solenopsis invicta*; thrips, e.g., *Thrips palini*; pear psylla, *Psylla pyri*; two-spotted spider mite, *Tetranychus urticae*; carmine mite. *Tetranychus cinnabarinus*; citrus rus mite, *Phyllocoptruta oleivora*; German cockroach, *Blatella germanica*; cat flea, *Ctenocephatides felia*; yellow fever mosquito, *Aedes aegypti*; and salt marsh mosquito, *Aedes sollioitans*.

In one screening approach, polynucleotide molecules having nucleotide sequences disclosed herein can be used to screen genomic or cDNA libraries. Screening can be performed with Met gene polynucleotides that are either DNA or RNA molecules, using standard techniques. See, for example, Ausubel et al. (eds.), *SHORT PROTOCOLS IN MOLECULAR BIOLOGY*, pages 6-1 to 6-11 (John Wiley & Sons, Inc. 1995). Insect genomic and cDNA libraries can be prepared using well-known methods. See, for example, Ausubel et al. (eds.), *SHORT PROTOCOLS IN MOLECULAR BIOLOGY*, pages 5-1 to 5-6 (John Wiley & Sons, Inc. 1995).

Additional bHLH-PAS/JHR genes can also be obtained using the polymerase chain reaction (PCR) with oligonucleotide primers having nucleotide sequences that are based upon the Met JHR nucleotide sequences described herein. General methods for screening libraries with PCR are provided by, for example, Yu et al., "Use of the Polymerase Chain Reaction to Screen Phage Libraries," in *METHODS IN MOLECULAR BIOLOGY*, Vol. 15: *PCR PROTOCOLS: CURRENT METHODS AND APPLICATIONS*, White (ed.), pages 211–215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in *METHODS IN MOLECULAR BIOLOGY*, Vol. 15: *PCR PROTOCOLS: CURRENT METHODS AND APPLICATIONS*, White (ed.), pages 317–337 (Humana Press, Inc. 1993).

Anti-Met JHR antibodies can also be used to isolate DNA sequences that encode bHLH-PAS/JHRs from cDNA libraries. For example, the antibodies can be used to screen λgt11 expression libraries, or the antibodies can be used for immunoscreening following hybrid selection and translation. See, for example, Ausubel et al. (eds.), *SHORT PROTOCOLS IN MOLECULAR BIOLOGY*, 3rd Edition, pages 6-12 to 6-16 (John Wiley & Sons, Inc. 1995); and Margolis et al., "Screening λ expression libraries with antibody and protein probes," in *DNA CLONING 2: EXPRESSION SYSTEMS*, 2nd Edition, Glover et al. (eds.), pages 1–14 (Oxford University Press 1995).

8. RFLP Analysis—Screening Populations for Resistance

Polynucleotides that encode bHLH-PAS/JHRs can be used to monitor an insect population for resistance to JH analog insecticides. For example, polynucleotides encoding Drosophila bHLH-PAS/JHRs from methoprene-sensitive and methoprene-resistant insects can be used to screen a pest insect population for an increase in methoprene resistance by restriction fragment length polymorphism (RFLP) analysis. Similarly, Dong et al. *Insect Biochem. Mol. Biol.* 24:647 (1994), have used RFLP analysis to examine the presence of knockdown resistance to pyrethroid insecticides in cockroach populations, Williamson et al., *Mol. Gen. Genet.* 240:17 (1993), identified RFLPs associated with resistance to DDT and pyrethroid insecticides in the housefly, while Severini et al., *J. Med. Entomol.* 31:496 (1994), used RFLP analysis to examine a possible increase in the frequency of an insecticide resistance gene (esterase B) in populations of the disease-bearing mosquito, *Culex pipiens*. RFLP analysis has also been used to examine populations of various mosquito species and screwworms. Severson et al., *Am. J. Trop. Hyg.* 50:425 (1994); Taylor et al., *Med. Vet. Entomol.* 10:63 (1996).

In an analogous approach, researchers have used RFLP analysis to differentiate between non-aggressive and aggressive strains of fungi and bacteria that are plant pathogens.

Koch et al., *Mol. Plant-Microbe Inter*. 4:341 (1991); Graham et al., *PhytoPathology* 80: 829 (1990). Also, see generally, Miller et al., "Diagnostic Techniques for Plant Pathogens," in *BIOTECHNOLOGY IN PLANT DISEASE CONTROL*, Chet (ed.), pages 321–339 (Wiley-Liss, Inc. 1993), Zilberstein et al., "Application of DNA Fingerprinting for Detecting Genetical Variation Among Isolates of the Wheat Pathogen *Mycosphaerella graminicola*," in *BIOTECHNOLOGY IN PLANT DISEASE CONTROL*, Chet (ed.), pages 341–353 (Wiley-Liss, Inc. 1993), and Honeycutt et al., "Application of the Polymerase Chain Reaction to the Detection of Plant Pathogens," in *THE IMPACT OF PLANT MOLECULAR GENETICS*, Sobral (ed.), pages 187–201 (Birkäuser 1996).

The identification of a genetic variant associated with juvenile hormone analog resistance (e.g., methoprene resistance) provides several avenues for testing to monitor the occurrence and frequency of insecticide resistance in a population at a very early stage when the frequency may be very low and/or difficult to detect by standard bioassays. This early detection facilitates informed judgments in the application of the relevant insecticide. For example, the gene Met encoding the juvenile hormone receptor (e.g., Met$^{A3}$) provides the basis for RFLP analysis of an insect population to identify the presence of the resistance trait in a given population. T. Wilson J. Econ. Ent. 86: 645–651 (1993).

Detection of the unique DNA associated with a resistance allele is diagnostic for the appearance of the resistance trait in the population sampled. This is determined by digesting genomic DNA collected from individuals of the target population in question with selected restriction enzyme(s) followed by probing a Southern blot with a detectably labelled DNA sequence that identifies a particular resistant trait, or a diagnostic portion thereof. By "diagnostic portion" thereof is meant any fragment of DNA from a bHLH-PAS JHR DNA sequence which differs sufficiently in sequence from the corresponding portion of the susceptible DNA sequence so as to be detectable in a Southern blot. A "diagnostic portion" may also be a unique DNA sequence genetically linked within one map unit of the trait that can be detected in a Southern blot analysis. DNA sequences flanking the resistance gene, as well as intervening sequences (introns) are particularly suited for identifying unique diagnostic RFLPs.

For example, the methoprene resistant alleles, Met$^{K17}$ and Met$^{A3}$, contain 1300 kb P-element insertions within the 1200 bp Bam H1 fragment immediately upstream from the Met$^+$ gene transcriptional start site. In this technique, DNA from several individuals in the target population is digested with an appropriate restriction enzyme, and size separated by gel electrophoresis. The gel, or a blot derived therefrom, is then probed with labelled DNA, using either the whole gene or a diagnostic fragment. If there are both resistant and sensitive alleles within an individual in the population, there will appear on the gel at least two different sized restriction fragments. Segments each fragment will hybridize with the bHLH-PAS/JHR gene probe.

In this manner, large numbers of individuals in the population can be sampled, and the relative abundance of an allele can be determined. Identification of the specific DNA fragment associated with resistance, whether by Southern or RFLP analysis, will always be diagnostic.

The present invention, thus generally described, will be understood more readily by reference to the following examples, which are provided by way of illustration and are not intended to be limiting of the present invention.

EXAMPLE 1

To isolate the Met JHR gene, genomic libraries were constructed from flies carrying either of two P-element alleles of Met, Met$^{A3}$ and Met$^{K17}$. These alleles were recovered in separate screens from methoprene-resistant flies. Wilson et al. *Molecular Mech. of Insecticide Resistance* (Am. Chem. Soc. Symp.) 505:99 (1992). Each allele conferred resistance to both the toxic and morphogenetic effects of JH and methoprene, and susceptible revertants could be recovered by standard genetic means. A 50 kilobase region surrounding the P-element insertion site was cloned from each library, as described by Turner and Wilson, *Arch. Insect Biochem. Biophys.* 30:133 (1995).

DNA sequencing and analysis of the genomic region located within one kilobase of the insertion sites revealed an open reading frame (ORF) located 273 base pairs from the insertion site in the Met$_{A3}$ allele and 424 base pairs in the Met$^{K17}$ allele. See FIG. 1. Transcription of this ORF occurs away from the P-element, suggesting possible interruption of transcription by the P-element, as has been found with other P-element mutations in Drosophila. Searles et al., *Mol. Cell Biol.* 6:3312 (1986); Kelley et al., *Mol. Cell. Biol.* 7:1545 (1987).

P-element mediated germline transformation was carried out with DNA fragments isolated from phage clones derived from a wild-type genomic library. Genomic fragments were isolated following restriction enzyme digestions of phage obtained from the iso-1 strain genomic library. (Tamkun et al. *Proc. Natl. Acad. Sci. USA* 81:5140 (1984)). The locations of the restriction sites for each fragment are shown in FIG. 1. Fragments were either subcloned into Bluescript (Stratagene Co., Ca.), then excised with an EcoRI-NotI double digest and subcloned into the pCaSpeR 4 transformation vector (Thummel et al. *Drosophila Inform. Serv.* 71:150 (1992)), or were subcloned directly into the pCaSpeR 4 vector. Purified plasmids together with pp25.1wc transformation "helper" DNA in a ratio of 2–3:1 were injected into dechorionated ywMet$^3$ embryos as described. (A. Spradling in *Drosophila—A Practical Approach* (D. B. Roberts, Ed. IRL, Oxford, 1986, page 175). Go progeny were individually crossed with ywMet$^3$, and transformants recognized by restoration of eye color ranging from light orange to red. For each DNA fragment, 3–5 transformants from separate Go females were recovered and their progeny tested for methoprene resistance.

Files carrying Met$^3$, a strong EMS-induced allele, were transformed with fragments shown in FIG. 1. Progeny of transformants were tested on three diagnostic amounts of methoprene as described in Wilson, *Arch. Insect Biochem. Physiol.* 32:641 (1996)). Resistant and susceptible animals were distinguished on the basis of survival as well as the presence of normal morphology of sternal bristle patterns and male genetalia.

When transformants with fragments St-X and K-H were tested for methoprene resistance, the level of resistance was undiminished compared with that of Met$^3$, indicating no rescue of the mutant phenotype. However, when Met$^3$ was transformed with the 6.234 Kb St-H fragment, resistance was lost, indicating that a functional Met sequence is contained in this sequence. The DNA region contained in fragment St-H corresponds well with the size and location of the transcripts.

The nucleotide sequence of the 6.234 Kb St-H fragment of FIG. 1 is shown in FIG. 2 (SEQ ID NO:1). The St-H fragment comprises an intron (lower case letters) and an open reading frame from base no. 1514 to base no. 3732.

Also shown in the Figure are the first (no. 1292) and last (no. 4301) bases of the genomic Met-JHR sequence in FIG. 3.

The St-H fragment was cloned into the SmaI site of the Bluescript(ks) vector, and is designated pSt-H. Vector pSt-H was deposited at the American Type Culture Collection, in Bethesda, Md., on Nov. 13, 1997. The present invention includes a polynucleotide having the nucleotide sequence of the St-H fragment in vector pSt-H.

EXAMPLE 2

A DNA probe to the ORF described above failed to identify any transcript(s) on a Northern blot of RNA from a methoprene-susceptible Oregon-RC late third-instar larvae, but a more sensitive RNA probe recognized a transcript of approximately 5.5 kilobases. Total RNA was isolated with TriReagent (Molecular Research Center, Inc., Ohio) from staged animals. Each lane was loaded with 40 mg of total RNA, subjected to denaturing gel electrophoresis on a formaldehyde-agarose gel, and blotted onto Hybond-N membrane. Following cross-linking, membranes were pre-hybridized in a solution containing 5×SSPE, 5×Denhardt's, 0.5% SDS, 50% formamide, and 100 µg/ml yeast tRNA for about 5 to about 7 hours at about 65° C.

Membranes were then hybridized in the same solution at about 68° C. for about 15 to about 17 hours with a [$^{32}$P]-UTP labeled riboprobe (Promega Co., Wis.) synthesized from a fragment of the Met-JHR gene. This fragment extended from nucleotide 771 through 1102 of the open reading frame, where nucleotide #1 is designated the base A in the ATG codon that begins the open reading frame. This corresponds to base no. 1514 through base no. 1845 in FIG. 2. The 771–1102 fragment was produced by PCR amplification from a genomic clone from the iso-1 phage containing the Met region. The amplified fragment was subcloned into a T-vector (Invitrogen, Ca.), linearized with SST II, and transcribed from the T7 promoter to produce a 331 bp antisense RNA molecule (the reverse transcript of the 771–1102 DNA fragment). The membranes were washed with 2×SSC+0.1% SDS at about 22° C. for about 20 minutes, followed by two washes with 0.1×SSC+0.1% SDS at about 65° for about 15 minutes each. Each membrane was placed against X-ray film and subjected to autoradiography at about −70° C. for 24 hours and developed. Control loading was evaluated by stripping the blot and reprobing with a [$^{32}$-P]-dCTP random-primed cDNA for the ribosomal protein-49 gene (Rp 49, O'Connell et al. *Nucl. Acid. Res.* 12:5495 (1984)).

Figure 8:
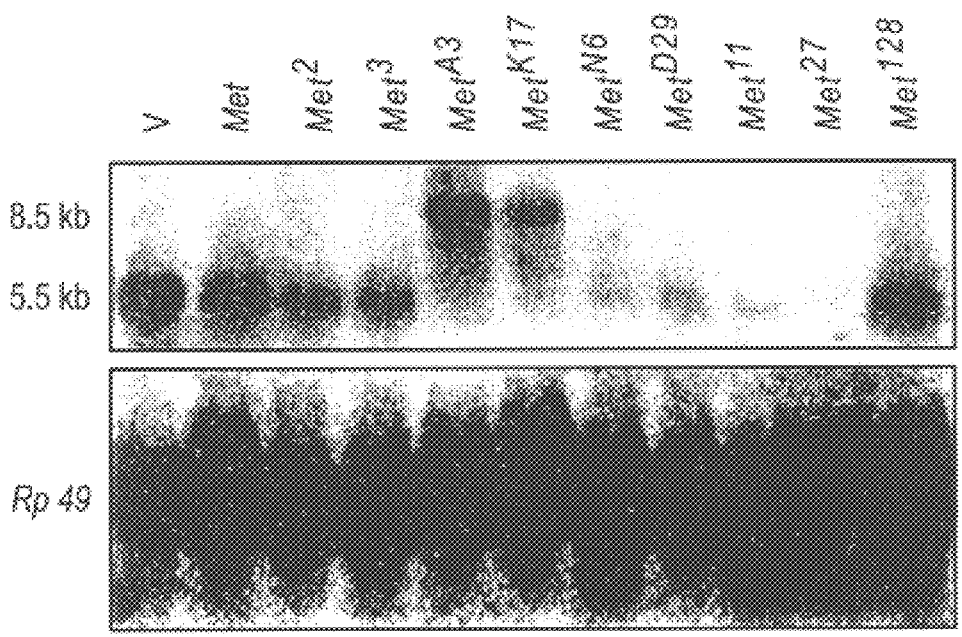
FIG. 8 shows the Northern blot of total RNA isolated from larvae homozygous for v or any of various other Met alleles, probed with a 331 bp riboprobe. Met, Met$^2$, Met$^3$ are EMS-induced alleles; Met$^{A3}$ and Met$^{K17}$ are P-element alleles, and the remaining alleles were X-ray induced from methoprene-susceptible vermillion (v) flies.

As shown in FIG. 8, the level of the 5.5 kb transcript was undiminished in three EMS-induced alleles of Met (Met, Met$^2$, and Met$^3$). The transcript was reduced in several alleles that were X-ray induced from methoprene-susceptible vermillion (v) flies (Met$^{N6}$, met$^{D29}$, Met$^{11}$, Met$^{27}$, Met$^{128}$), especially Met$^{27}$, which appears as a null allele. Met$^{43}$ and Met$^{K17}$ (P-element alleles) also showed a transcript that is approximately three kilobases larger than the 5.5 kilobase transcript, suggesting that transcriptional run-on of the 2.9 kilobase P-element is occurring in these flies. A similar transcriptional run-on observation has been seen with the P-element allele of yellow mutant.

The boundaries of the 5.5 kb transcript have not been precisely determined, but they have been inferred by RT-PCR to include a transcriptional start site about 1,100 bp upstream of the ATG site and an end site about 2,200 bp from the stop codon of the ORF. See FIG. 1.

Figure 9:
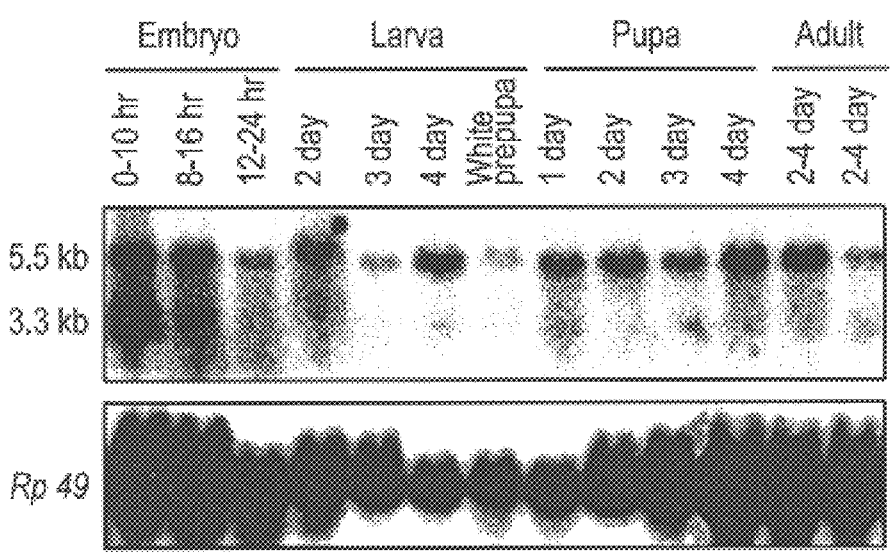
FIG. 9 shows a developmental Northern of total RNA isolated from the methoprene-susceptible Oregon-RC strain at various times in development, probed with the 331 bp riboprobe. The indicated times for larvae are +/−8 hours.

As shown in FIG. 9, a Northern analysis was carried out to determine the abundance and temporal appearance of Met-JHR transcripts. During the first half of embryonic development, a transcript of approximately 3.3 kilobases was detected in methoprene-susceptible Oregon-RC adult females. Total RNA was isolated from these females at various times during development. Each lane of the gel was loaded with with 40 mg of total RNA, and the blot was probed with the 331 bp Met-JHR riboprobe, followed by a DNA probe for the Rp49 gene, as described above. Embryos were collected from overnight cultures and either frozen in liquid nitrogen or maintained at 25° C. until the desired age (0–10 hours, 8–16 hours, 16–24 hours). Larvae were staged from timed embryo collections (2 days +/−8 hrs; 3 days +/−8 hrs; 4 days +/−8 hrs; white prepupa) Pupas were staged from the white prepupal stage, which lasts about one hour (1 day, 2 day, 3 day, and 4 day) Adult males consistently show only the 5.5 Kb transcript. Females show both the 3.3 kb and the 5.5 kb transcript, and when fully gravid, show increased levels of the 3.3 kb transcript. The 3.3 Kb transcript is present only in embryos and adult ovary tissue. Additionally, since methoprene-sensitivity in fly development is found only in late larval-early pupal stage, the appearance of the 3.3 Kb transcript is not correlated with methoprene resistance.

EXAMPLE 3 cDNA molecules corresponding to the region containing the Met-JHR ORF, as well as to the smaller (3.3 kb) transcript, were isolated as apparent full-length cDNAs from a Drosophila wild-type Canton-S ovary cDNA library and were sequenced to establish a relationship of the transcript with the genomic nucleotide sequence. The probable transcription start site for this transcript begins 220 bp upstream from the start codon and the probably transcript ends 912 bp from the stop codon.

A comparison of the cDNA to the genomic sequence showed that the genomic ORF is 2.22 Kb and the cDNA ORF is 2.151 Kb. The difference between the two sequences is a 69 nucleotide intron, which corresponds to 23 codons, and does not change the open reading frame of the genomic and cDNA. The presence of the intron provides evidence for the possibility of alternatively spliced variants of Met-JHR and hence multiple isoform proteins of Met-JHR.

The longest single open reading frame in the cDNA in FIG. 3 (SEQ ID NO:3) comprises a single open reading frame (ORF). The DNA sequence (CAAA<u>ATG</u>GCA) (SEQ ID NO:13) surrounding this ATG of the ORF is in good agreement with a Drosophila translation start site consensus sequence. *Cavener Nucl. Acid. Res.* 15:1353 (1987).

The first genomic exon is from position 224 to position 1543 (1296 bases). This is followed by a 69 bp intron, and a second exon, which extends from position 1589 to 2443 (855 bases). The remainder of the Met-JHR gene is from 2443 to 3011 (568 bases). The total length of the nucleotide sequence provided for the genomic DNA is 3011 nucleotides (SEQ ID NO:2), and that of the cDNA is 3282 nucleotides (SEQ ID NO:3).

Comparison of the Met-JHR ORF and with sequences deposited in the Genbank database showed three regions of homology to members of a family of transcriptional activators known as the basic helix-loop-helix-Per-Arnt-Sim (bhlh-PAS) proteins. See FIG. 6. Three vertebrate members of this family include the aromatic hydrocarbon receptor nuclear translocator (ARNT), muscle and brain ARNT-like protein 1 (BMAL-1), and the aromatic hydrocarbon receptor (AHR). Three Drosophila family members include ARNT (DARNT), Trachealess (Trh) and Single-minded (Sim).

Figure 6A:
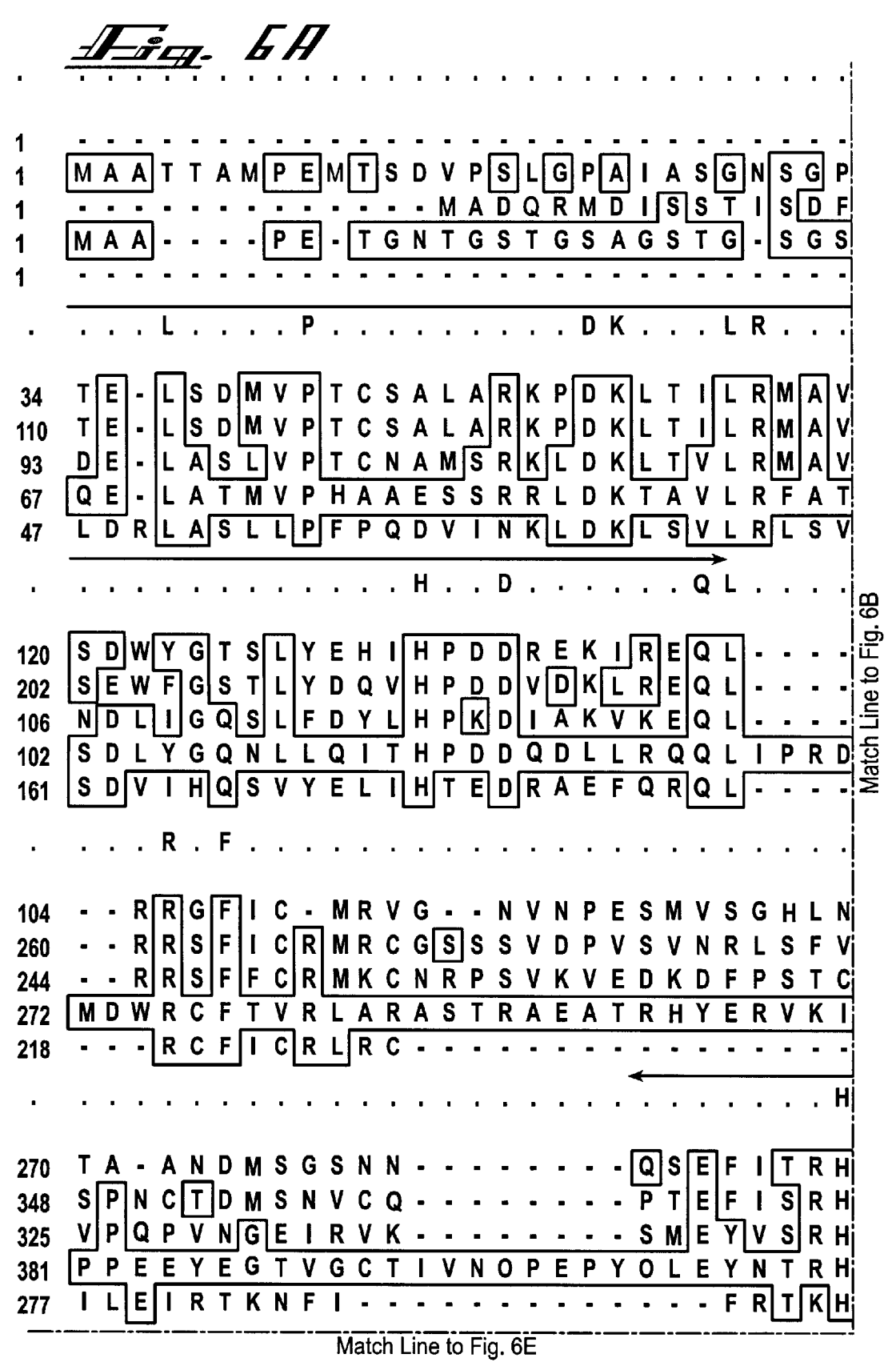
Figure 6B:
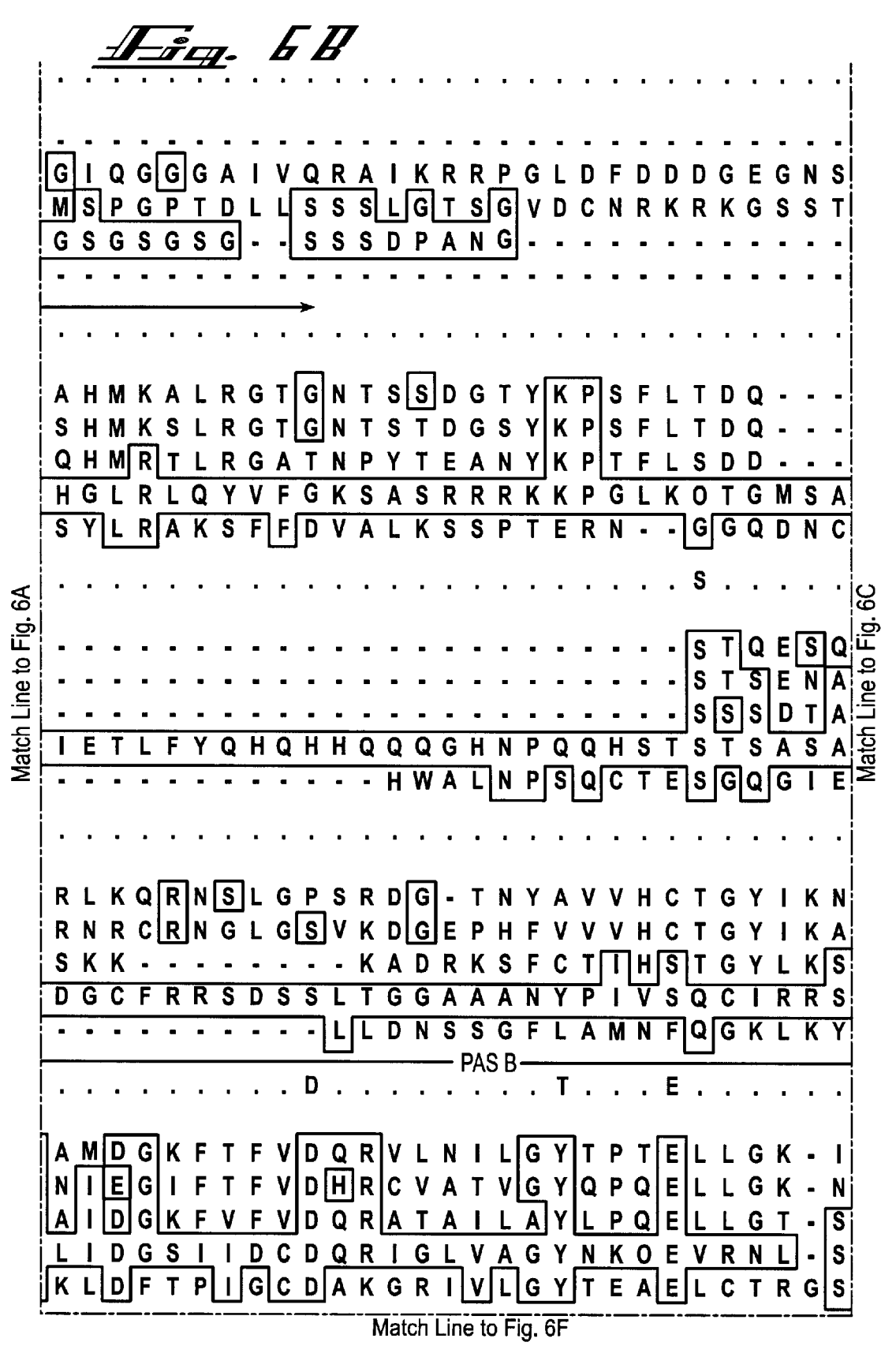
Figure 6C:
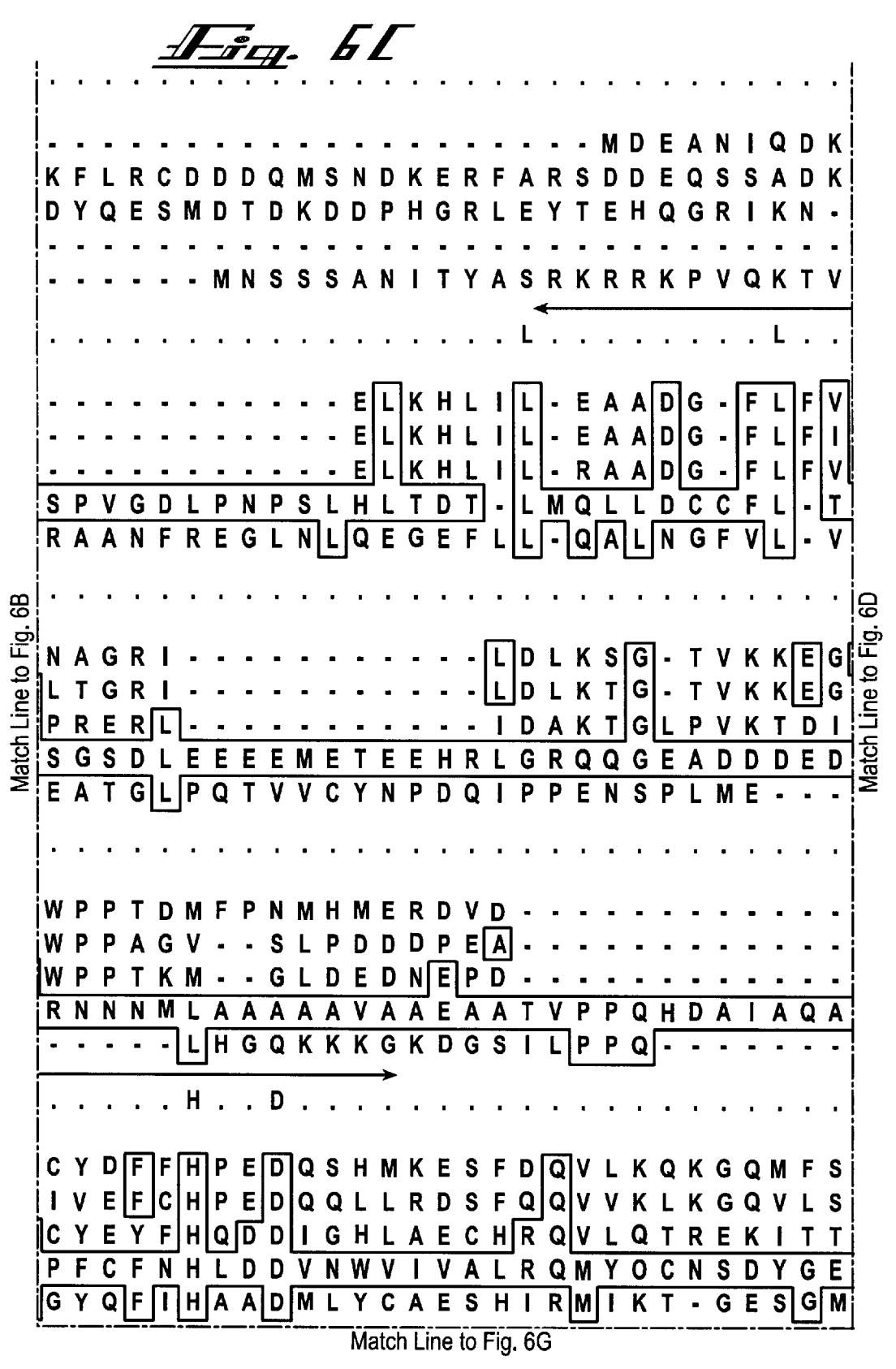

The ARNT and AHR proteins are involved as heterodimeric partners in binding a variety of environmental toxicants, including dioxin, and subsequently activating a variety of genes important in the degradation of these chemicals, such as the cytochrome P450 genes. FIG. 6 indicates that Met-JHR is neither DARNT nor AHR. However, Met-JHR shares considerable homology to human AHR in the ligand binding region of AHR, which is amino acids 200–400 of AHR. Rowlands et al. *Crit. Rev. Toxicol.* 27:109 (1997). Another feature apparent from visual inspection of the Met-JHR sequence is that Met-JHR, like human ARH (HARH), has a high concentration of serine and threonine residues at its carboxyl terminus. This is the motif of a S/P/T transactivation domain, as noted above. In ARH, this domain has been shown to be a functional TAD.

These features support the hypothesis that the mechanism of action of Met-JHR is similar to AHR, i.e., Met-JHR binds the JH ligand. In addition, the Met-JHR may heterodimerize to DARNT or a DARNT-like protein in order to bind a JH response element and mediate JH action. The bHLH domain has been shown to be involved in dimerization and DNA binding. Rowlands et al. *Critical Reviews in Toxicology*, 27: 109 (1997).

Met-JHR also contains the "LXXLL (SEQ ID NO:14)" motif which likens Met to steroid receptor co-activators. Although this motif is found in many proteins, it plays a significant role in proteins that interact with co-activators of steroid receptors. LXXLL (SEQ ID NO14) also has been found in a bHLH-PAS protein that is a cofactor (ACTR) [Chen et al. *Cell* 90:569 (1997)] that is amplified in breast cancer-1 (AIBC). Anzick et al. *Science* 277:965 (1977). This bHLH-PAS protein (ACTR/AIBC) interacts with a steroid receptor, and is part of the muti-protein complex that potentiates the signal from the steroid receptor ligand.

Met-JHR also has homology with Single Minded (Sim), a neurogenic transcriptional factor that has been identified as a Drosophila bHLH-PAS family member. However, Sim has not been identified as a ligand-binding protein.

EXAMPLE 4

A JHR Met nucleotide sequence was isolated from a cDNA library from *D. erecta*, Met-JHR-erecta. A reverse oligonucleotide primer was based on the 5' end of the PAS-A region of the Drosophila Met-JHR gene, TLMQLL. Using this primer, standard polymerase chain reaction is (PCR) techniques were used to amplify DNA sequences from *D. erecta*. The amplified DNA was subcloned into a plasmid and sequenced. The sequence obtained from *D. erecta* includes 232 nucleotides from the N-terminal portion of the Met-erecta-JHR ORF. As shown in FIG. 5, there is high homology between the two genes, suggesting that the Met$^+$ gene may be conserved throughout Drosophila and the order Diptera.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. An isolated polynucleotide which comprises the sequence of SEQ ID NO:6.

2. An isolated polynucleotide comprising the nucleotide sequence of the St-H fragment in vector pSt-H.

3. The vector pSt-H.

4. An isolated DNA molecule comprising a polynucleotide having the sequence of SEQ ID NO: 1.

5. An isolated DNA molecule comprising a polynucleotide having the sequence of SEQ ID NO: 2.

6. An isolated DNA molecule comprising a polynucleotide having the sequence of SEQ ID NO: 3.

7. An isolated DNA molecule consisting of a polzynucleotide having the sequence of SEQ ID) NO:7.

8. An isolated DNA molecule comprising a polynucleotide which is a functional variant of SEQ ID NO: 1.

9. An isolated DNA molecule comprising a polynucleotide which is a functional variant of SEQ ID NO: 2.

10. An isolated DNA molecule comprising a polynucleotide which is a functional variant of SEQ ID NO: 3.

11. An expression vector comprising a polynucleotide having the sequence of SEQ ID NO: 1.

12. An expression vector comprising a polynucleotide having the sequence of SEQ ID NO: 3.

13. An expression vector comprising a polynucleotide having the sequence of SEQ ID NO: 7.

14. A host cell comprising the expression vector of claim 11.

15. A method of producing a polypeptide expressed by an expression vector comprising the steps of:
(a) culturing a host cell comprising the expression vector of claim 11, and
(b) isolating said polypeptide from said cultured host cell.

16. A host cell comprising the expression vector of claim 12.

17. A method of producing a polypeptide expressed by an expression vector comprising the steps of:
(a) culturing a host cell comprising the expression vector of claim 12, and
(b) isolating said polypeptide from said cultured host cell.

18. A host cell comprising the expression vector of claim 13.

19. A method of producing a polypeptide expressed by an expression vector comprising the steps of:
(a) culturing a host cell comprising the expression vector of claim 13, and
(b) isolating said polypeptide from said cultured host cell.

20. The host cell of claim 14, wherein said host cell is selected from the group consisting of bacterial cell, yeast cell, insect cell and mammalian cell.

21. The host cell of claim 16, wherein said host cell is selected from the group consisting of bacterial cell, yeast cell, insect cell and mammalian cell.

22. The host cell of claim 18, wherein said host cell is selected from the group consisting of bacterial cell, yeast cell, insect cell and mammalian cell.

23. An isolated DNA molecule comprising a polynucleotide encoding a polypeptide having an amino acid sequence selected from the group consisting of SEQ ID NO:4 and SEQ ID NO:5.

24. An isolated DNA molecule consisting of a polynucleotide fragment of SEQ ID NO:1, wherein the fragment is selected from the group consisting of a polynucleotide fragment comprising nucleotides 1 through 1291, a polynucleotide fragment comprising nucleotides 1 through 1513, a polynucleotide fragment comprising nucleotides 3733 through 6235 and a polynucleotide fragment comprising nucleotides 4302 through 6235.

* * * * *